(12) United States Patent
Daub et al.

(10) Patent No.: US 8,959,984 B2
(45) Date of Patent: Feb. 24, 2015

(54) PROTEOME-WIDE QUANTIFICATION OF SMALL MOLECULE BINDING TO CELLULAR TARGET PROTEINS

(75) Inventors: Henrik Daub, München (DE); Michaela Bairlein, Berlin (DE); Kirti Sharma, New Dehli (IN); Klaus Godl, Krailling (DE); Andreas Tebbe, München (DE); Christoph Weber, München (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 922 days.

(21) Appl. No.: 12/681,468

(22) PCT Filed: Sep. 26, 2008

(86) PCT No.: PCT/EP2008/062979
§ 371 (c)(1),
(2), (4) Date: Jul. 15, 2010

(87) PCT Pub. No.: WO2009/043829
PCT Pub. Date: Apr. 9, 2009

(65) Prior Publication Data
US 2010/0279891 A1  Nov. 4, 2010

Related U.S. Application Data

(60) Provisional application No. 60/977,692, filed on Oct. 5, 2007.

(30) Foreign Application Priority Data

Oct. 5, 2007 (EP) .................................... 07117996

(51) Int. Cl.
*G01N 33/53* (2006.01)
*G01N 33/543* (2006.01)
(Continued)

(52) U.S. Cl.
CPC ...... *G01N 33/54306* (2013.01); *G01N 30/8675* (2013.01); *G01N 30/6043* (2013.01); *G01N 30/7233* (2013.01); *C12Q 1/485* (2013.01); *G01N 33/6851* (2013.01)
USPC ............ 73/61.52; 210/656; 422/70; 436/518; 436/525; 436/527

(58) Field of Classification Search
CPC .................. G01N 33/54306; G01N 33/54333; G01N 33/6851; G01N 33/6848; G01N 2458/15; C12Q 1/485
USPC ........................................................... 422/70
See application file for complete search history.

(56) References Cited

U.S. PATENT DOCUMENTS

| 5,324,633 A | 6/1994 | Fodor et al. |
| 2005/0009099 A1 | 1/2005 | Lockhart et al. |

(Continued)

FOREIGN PATENT DOCUMENTS

| JP | 2007-047024 | 2/2007 |
| WO | 90/10450 | 9/1990 |

(Continued)

OTHER PUBLICATIONS

Brehmer et al (Cancer Res. Jan. 15, 2005, 65(2), 379-382).*

(Continued)

*Primary Examiner* — Christopher M Babic
*Assistant Examiner* — Jeremy C Flinders
(74) *Attorney, Agent, or Firm* — MH2 Technology Law Group, LLP

(57) ABSTRACT

This invention relates to methods for the evaluation and/or quantification of the binding affinity of small molecules or other compounds to target components contained within an analyte, such as target proteins contained within the proteome of a cell or tissue.

39 Claims, 23 Drawing Sheets

(51) Int. Cl.
*G01N 33/551* (2006.01)
*C12Q 1/48* (2006.01)
*G01N 33/68* (2006.01)
*G01N 30/00* (2006.01)
*G01N 30/72* (2006.01)
*G01N 30/86* (2006.01)
*G01N 30/60* (2006.01)

(56) References Cited

U.S. PATENT DOCUMENTS

2007/0087348 A1 4/2007 Notcovich et al.
2007/0122913 A1 5/2007 Tanaka et al.

FOREIGN PATENT DOCUMENTS

WO 2006/134056 12/2006
WO 2007/104763 9/2007

OTHER PUBLICATIONS

Godl, Klaus et al, "An efficient proteomics method to identify the cellular targets of protein kinase inhibitors," Proceedings of the National Academy of Sciences of the United States of America (PNAS), Dec. 23, 2003, vol. 100, No. 26, pp. 15434-15439, XP002461718.
Annis, Allen D. et al., "Method for Quantitative Protein—Ligand Affinity Measurements in Compounds Mixtures," Analytical Chemistry, Jun. 15, 2007, vol. 79, No. 12, pp. 4538-4542, XP002461720.
Annis, Allen D. et al., "A General Technique to Rank Protein-Ligand Binding Affinities and Determine Allosteric versus Direct Binding Site Competition in Compounds Mixtures," Journal of the American Chemical Society, Dec. 1, 2004, vol. 126, No. 47, pp. 15495-15503.
Valsasina, Barbara et al., "Kinase selectivity profiling by inhibitor affinity chromatography," Expert Review of Proteomics, Oct. 2004, vol. 1, No. 3, pp. 303-315, XP008061618.
International Searching Authority, PCT Notification of Transmittal of the International Search Report and the Written Opinion of the International Searching Authority, or the Declaration, PCT International Application No. PCT/EP2008/062979, Jan. 15, 2009, pp. 1-14.
Bantscheff, Marcus et al., "Quantitative mass spectrometry in proteomics: a critical review," Anal Bioanal. Chem., Aug. 1, 2007, 389, pp. 1017-1031.
Third Party Observation for European Patent Application No. 08 804 842.6 dated Oct. 31, 2011, pp. 1-12.
Third Party Observation from European Patent Application No. 08 804 642.6 dated Aug. 3, 2012, pp. 1-13.
Preliminary Opinion (Nullity Action) of the Federal Patent Court dated Nov. 22, 2012, 2 Pages. (English Abstract).
Japanese Office Action dated Oct. 2, 2012 from Japanese Patent Application No. 2010-527423, 6 Pages (with English Translation).
Boyer, Philip M. et al, Effects of Ligand Concentration on Protein Adsorption in Dye-Ligand Adsorbents. Chemical Engineering Science, vol. 47, No. 1, 1992, pp. 241-251.
Boyer, Philip M. et al. Protein Purfication by Dey Ligand Chromatography. Advances in Biological Engineering Biotechnology, 1993, vol. 49, pp. 1-44.
Fabian, Miles A. et al. A small molecule-kinase interaction map for clinical kinase inhibitors. Nature Biotechnology, Mar. 2005, vol. 23, No. 3, pp. 329-336.
White, Forest M. On the iTRAQ of kinase inhibitors. Nature Biotechnology, Sep. 2007, vol. 25, No. 9, pp. 994-996.
Yamamoto, Kiyoshi et al. A versatile method of identifying specific binding proteins on affinity resins. Analytical Biochemistry, 2006, vol. 352, pp. 16-23.
Lolli, Graziano et al. Inhibitor affinity chromatography: Profiling the specific reactivity of the proteome with immobilized molecules Proteomics, 2003, vol. 3, pp. 1287-1298.
Schuck et al. Measuring Protein Interactions by Optical Biosensors. Current Protocols in Protein Science, Quantitation of Protein Interactions, Unit 20.2, Supplement 17, 1999, pp. 20.2.1-20.2.22.
Bantscheff, Marcus et al. Quantitative chemical proteomics reveals mechanisms of action of clinical ABL kinase inhibitors. Nature Biotechnology, Sep. 2007, vol. 25, No. 9, pp. 1035-1044.
Brehmer, Dirk et al. Proteome-wide Indentification of Cellular Targets Affected by Bisindolyimaleimide-type Protein Kinase C Inhibitors. Molecular & Cellular Proteomics 3.5, 2004, pp. 490-500.
Patent Examination Report No. 1 from Australian Patent Application 2008307000 dated Jul.. 3, 2013, pp. 1-11.
Mann, David A. et al. Probing Low Affinity and Multivalent Interactions with Surface Plasmon Resonance: Ligands for Concavalin A. Journal of the American Chemical Society, Oct. 21, 1998, vol. 120, No. 41, pp. 10575-10582.
Viht, Kaido et al. Surface-plasmon-resonance-based biosensor with immobilized bisubstrate analog inhibitor for the determination of affinities of ATP-and protein-competitive ligands of cAMP-dependent protein kinase. Analytical Biochemistry, Mar. 2007, vol. 362, pp. 268-277.
Communication Pursuant to Article 94(3) EPC from European Patent Application No. 08 804 842.6 dated Aug. 27, 2012, 7 Pages.
Communication Pursuant to Article 94(3) EPC from European Patent Application No. 08 804 842.6 dated Sep. 10, 2010, 5 Pages.
Communication Pursuant to Article 94(3) EPC from European Patent Application No. 08 804 842.6 dated Feb. 15, 2012, 6 Pages.

\* cited by examiner

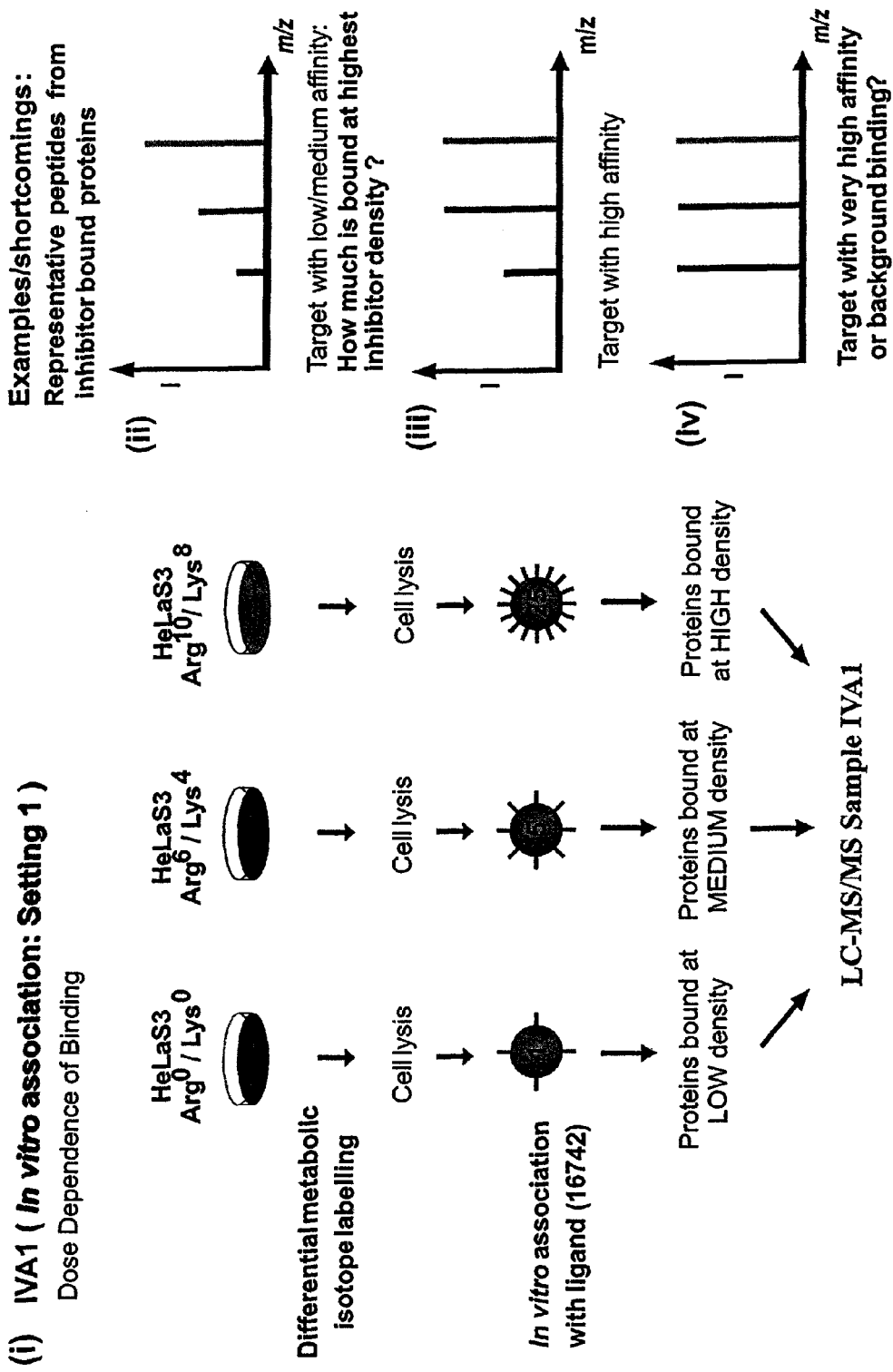

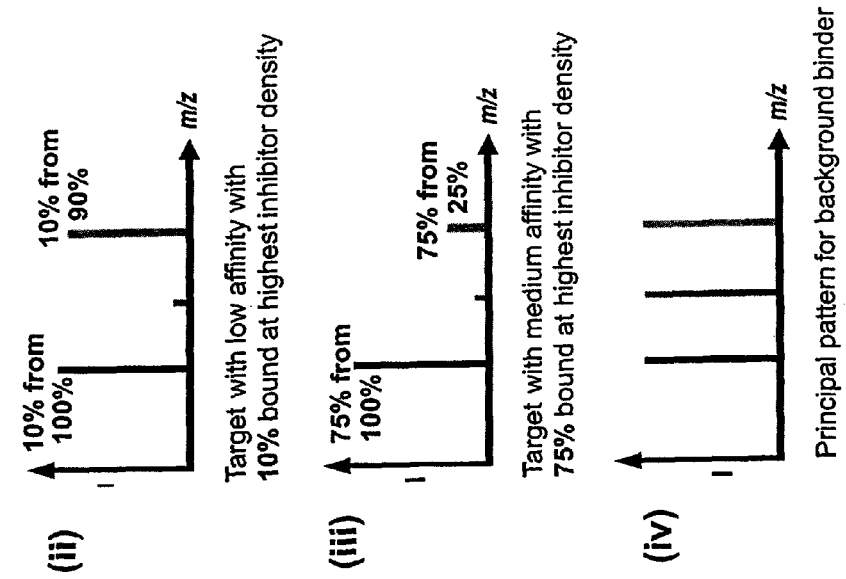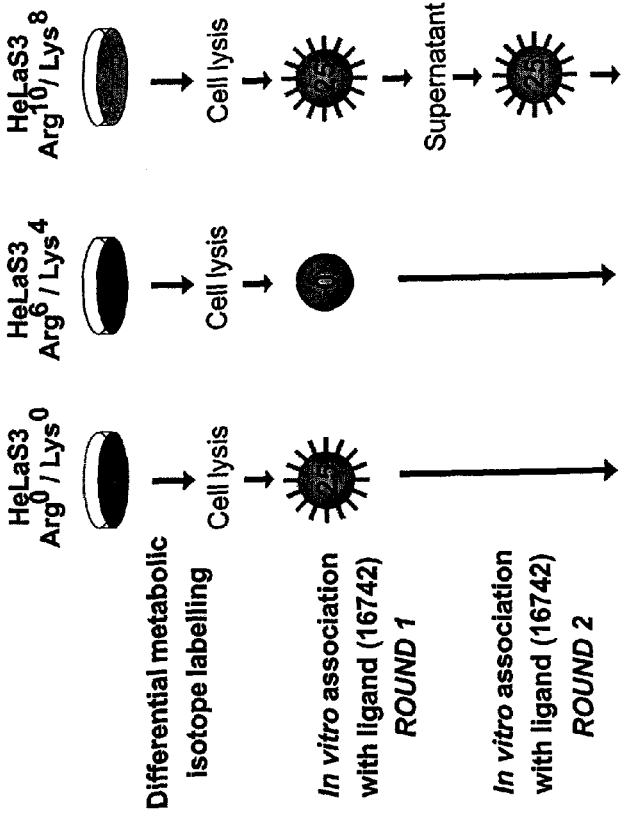
Figure 1b

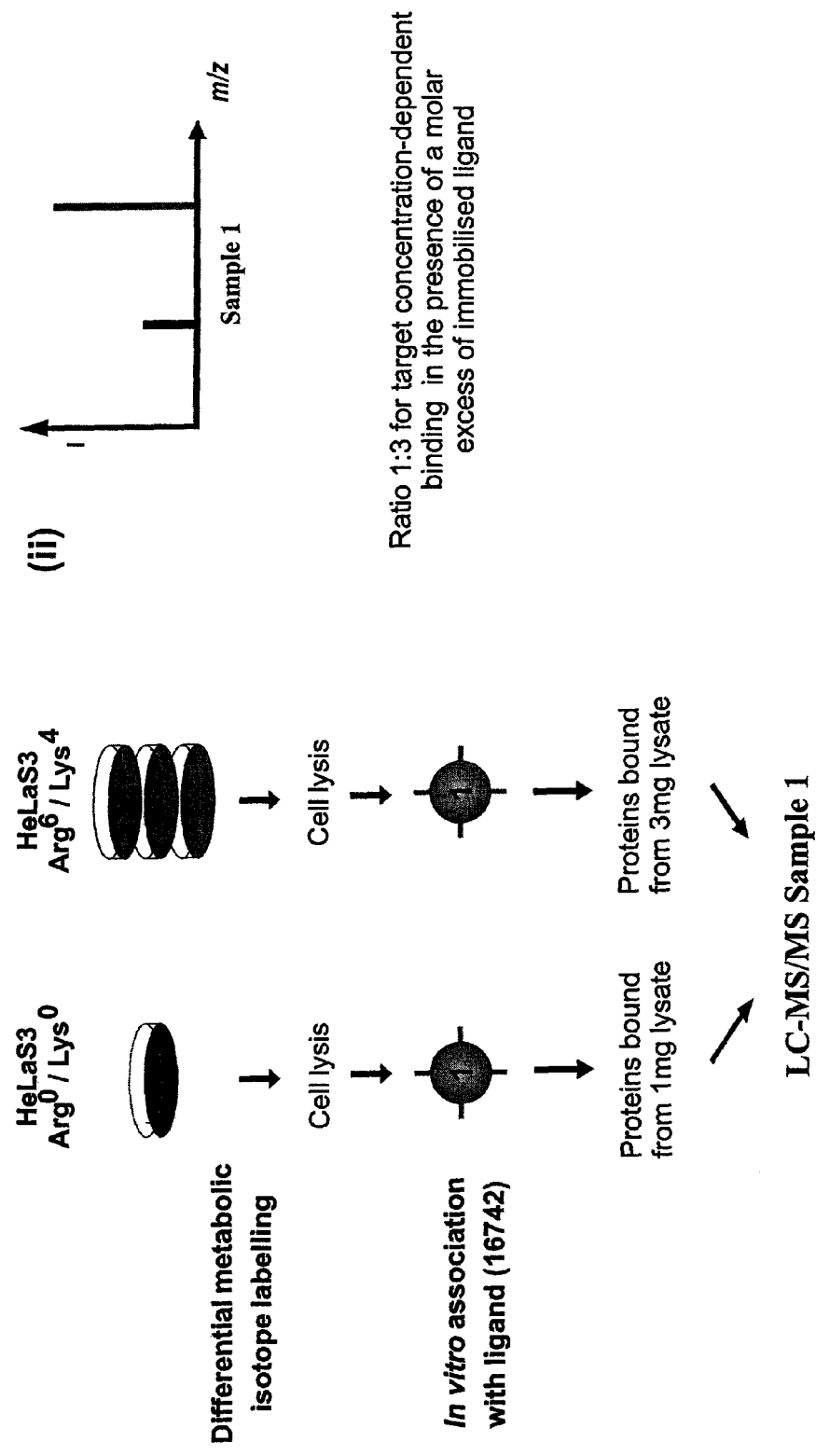

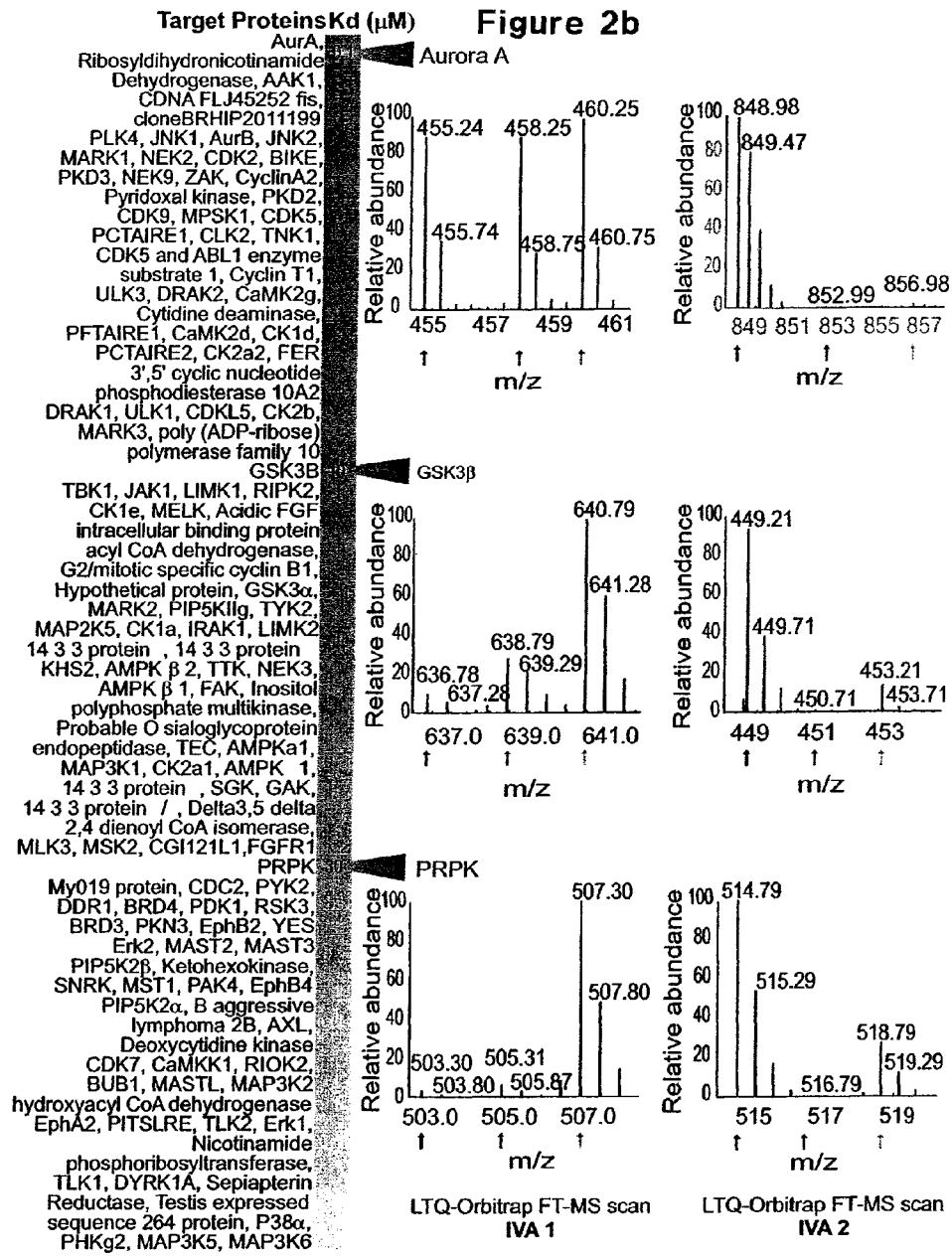

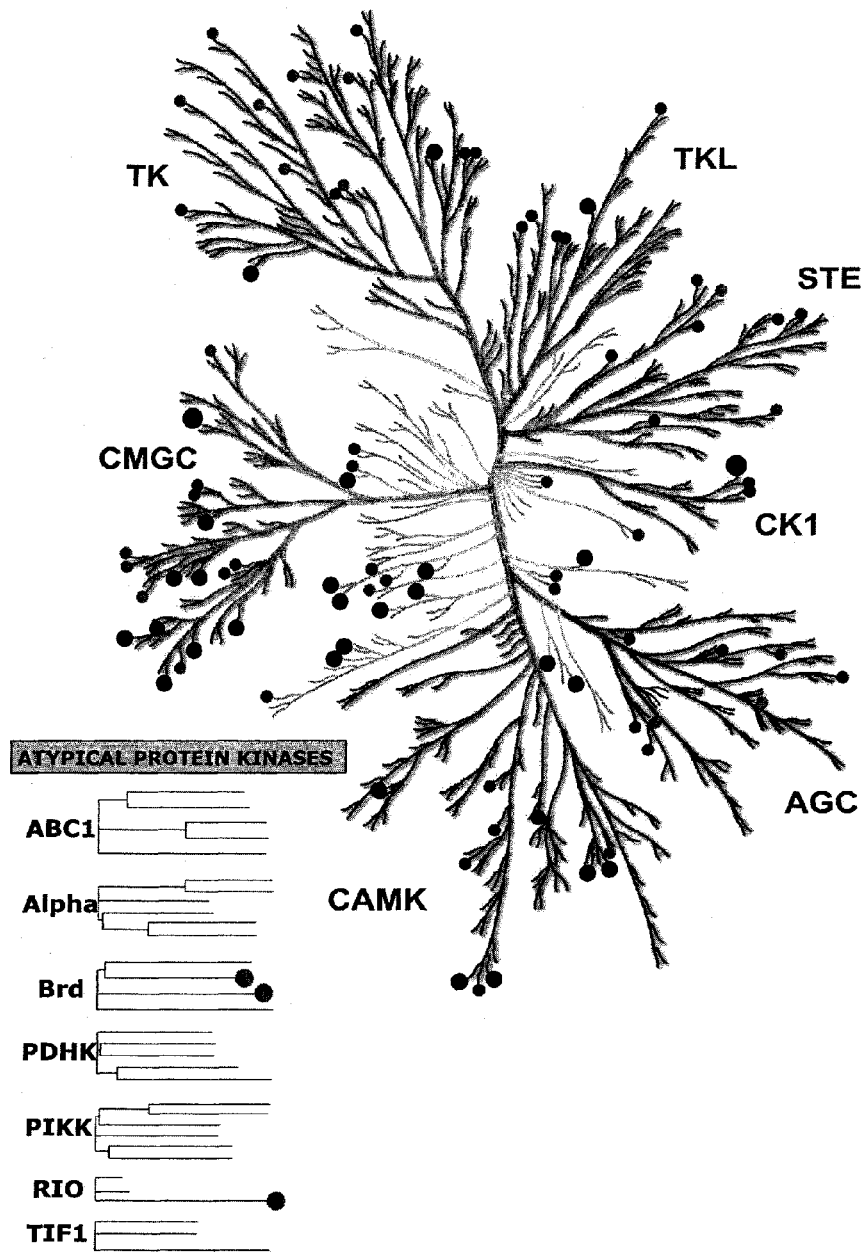

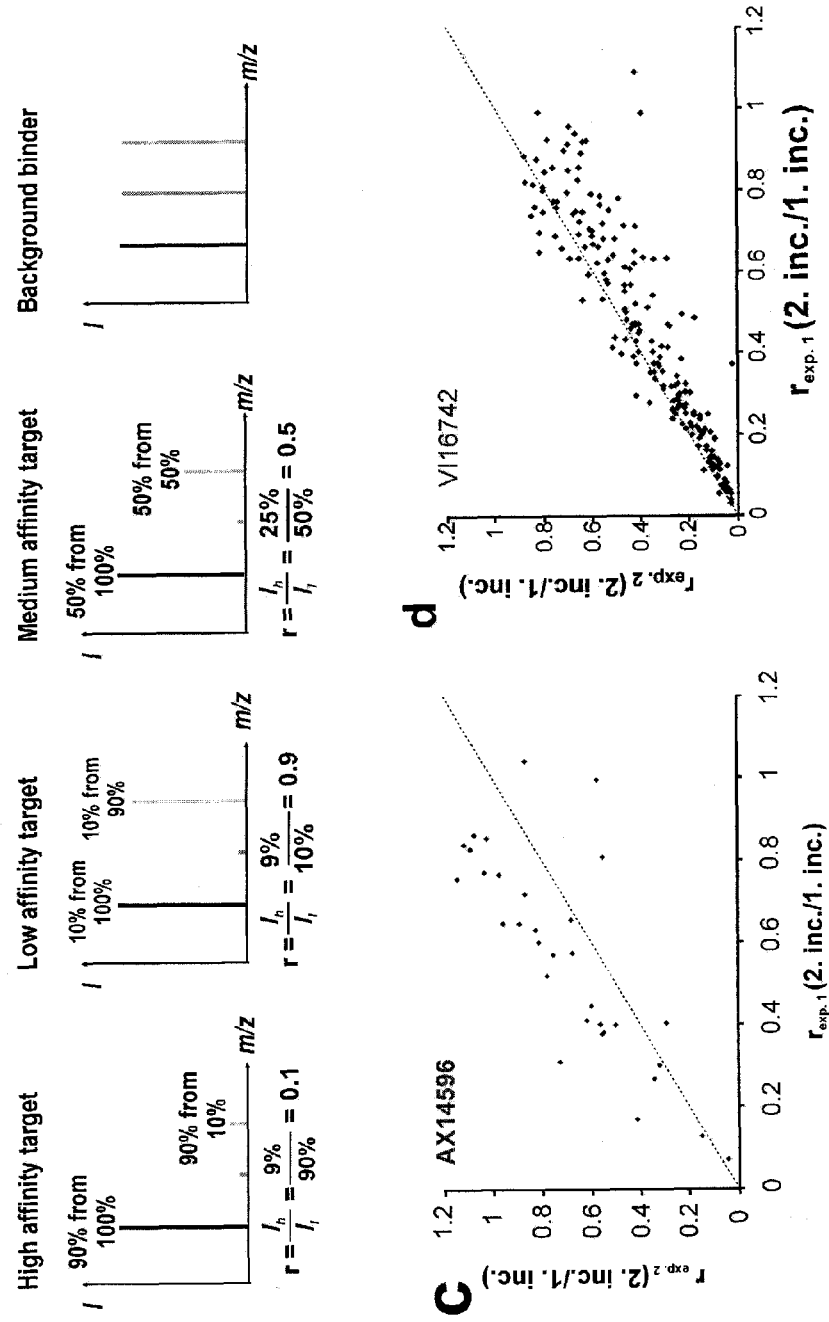
Figure 6b-d

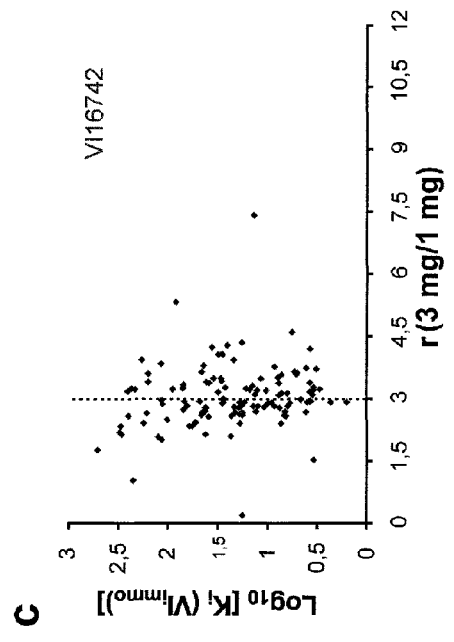
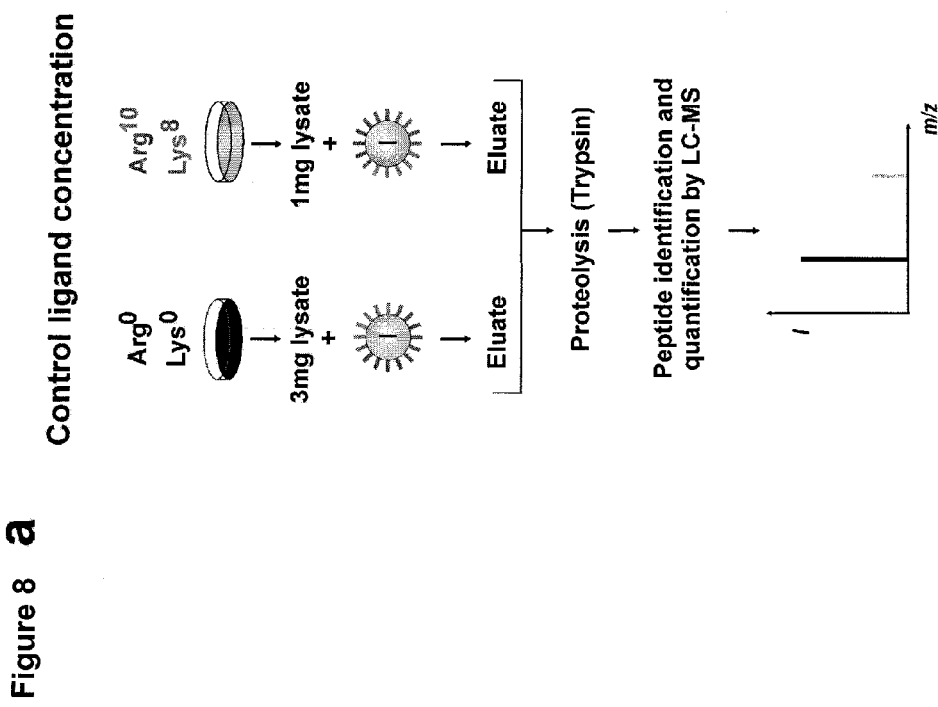
Figure 8

Figure 9
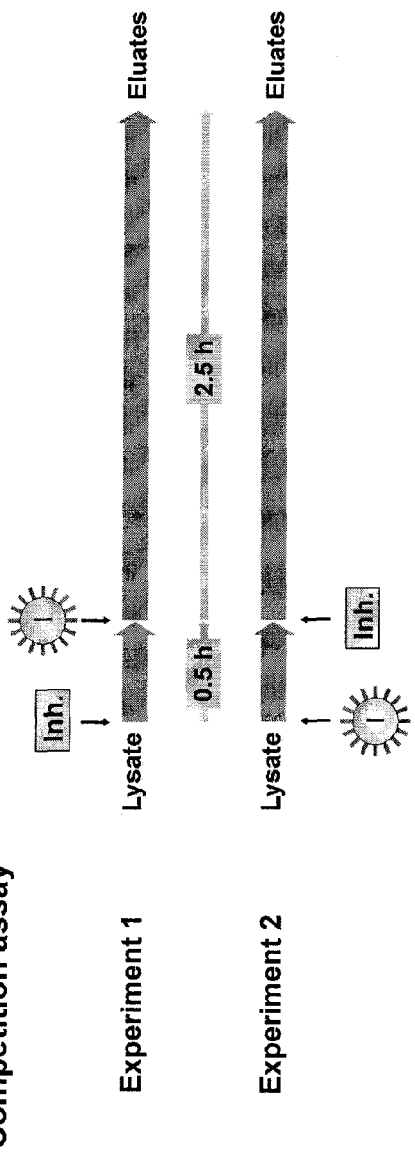
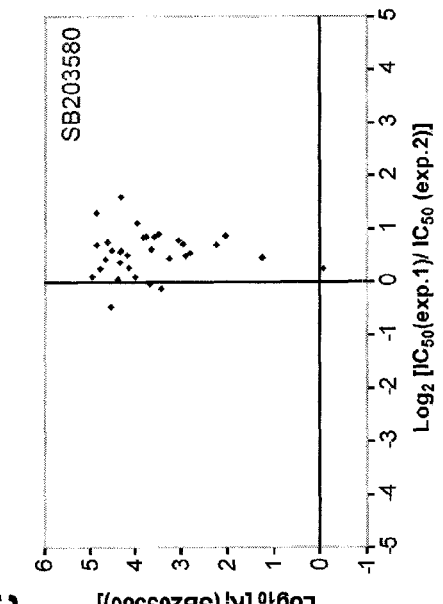
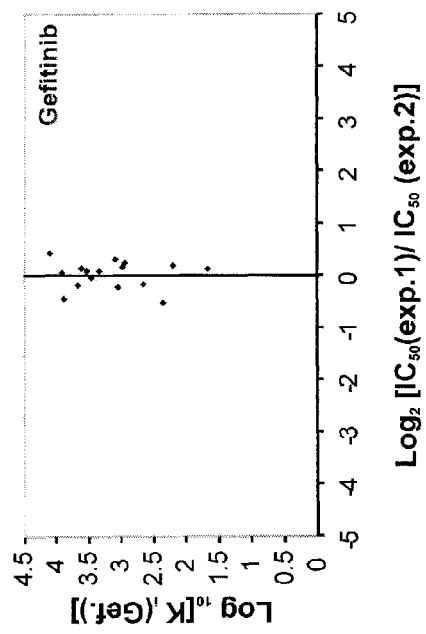

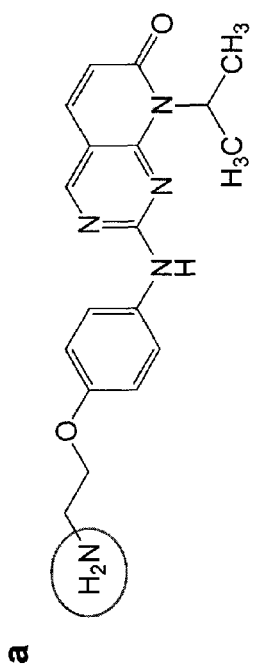
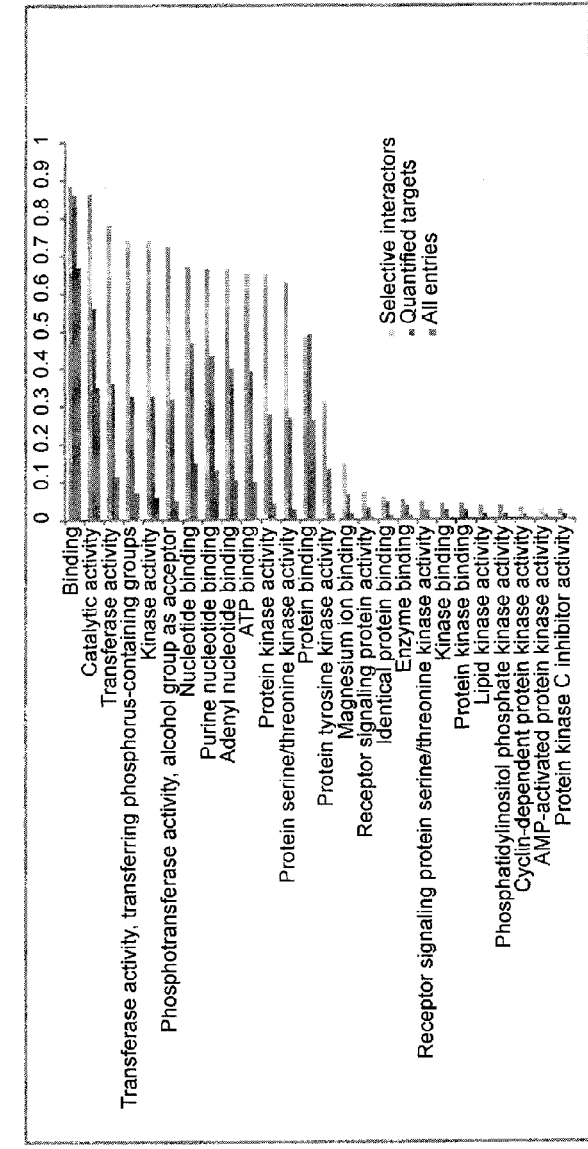
Figure 10

Figure 12: Structure of dasatinib and the corresponding immobilized dasatinib affinity resin.

| Protein Name | $K_{d, free}$ [µM] |
|---|---|
| Proto-oncogene tyrosine-protein kinase ABL1 (ABL1) | 0.0016 |
| Ephrin type-B receptor 4 precursor (EPHB4) | 0.0021 |
| Tyrosine-protein kinase ABL2 (ABL2) | 0.0028 |
| Tyrosine-protein kinase Lyn (LYN) | 0.0060 |
| Tyrosine-protein kinase FRK (FRK) | 0.0064 |
| Proto-oncogene tyrosine-protein kinase Src (SRC) | 0.0064 |
| Receptor-interacting serine/threonine-protein kinase 2 (RIPK2) | 0.0076 |
| Proto-oncogene tyrosine-protein kinase Yes (YES1) | 0.0080 |
| Tyrosine-protein kinase CSK (CSK) | 0.0088 |
| Activated CDC42 kinase 1 (TNK2) | 0.0089 |
| Mast/stem cell growth factor receptor precursor (KIT) | 0.0118 |
| Mitogen-activated protein kinase kinase kinase 4 (MAP3K4) | 0.0128 |
| Discoidin domain receptor family, member 1 (DDR1) | 0.0135 |
| Tyrosine-protein kinase BTK (BTK) | 0.0174 |
| Tyrosine-protein kinase Tec (TEC) | 0.0184 |
| Serine/threonine-protein kinase QSK (QSK) | 0.0225 |
| Cyclin G-associated kinase (GAK) | 0.0353 |
| Serine/threonine-protein kinase SNF1-like kinase 2 (SNF1LK2) | 0.1008 |
| Mitogen-activated protein kinase kinase kinase kinase 5 (MAP4K5) | 0.1347 |
| Mitogen-activated protein kinase 14 (MAPK14) | 0.1534 |
| Mitogen-activated protein kinase kinase kinase MLT (MLTK) | 0.1897 |
| Putative myosin light chain kinase 3 (MYLK3) | 0.1979 |
| Ras suppressor protein 1 (RSU1) | 0.2414 |
| Membrane-associated tyrosine- and threonine-specific cdc2-inhibitory kinase (PKMYT1) | 0.2445 |
| Integrin-linked protein kinase (ILK) | 0.2551 |
| LIM and senescent cell antigen-like-containing domain protein 1 (LIMS1) | 0.2562 |
| Uncharacterized protein PARVB (PARVB) | 0.2966 |
| LIM domain kinase 2 (LIMK2) | 0.4186 |
| STE20-related adapter protein (STRAD) | 0.5029 |
| Diphthine synthase (DPH5) | 0.6861 |
| Activin receptor type-1 precursor (ACVR1) | 1.2020 |
| Uncharacterized protein NUDT5 (NUDT5) | 1.3054 |
| Amidophosphoribosyltransferase precursor (PPAT) | 1.5677 |
| Adenosine kinase (ADK) | 2.1242 |
| Nuclear cap-binding protein subunit 1 (NCBP1) | 9.1232 |

Figure 14: Table of dasatinib target proteins determined from K562 cell extracts and their corresponding $K_d$ values.

PROTEOME-WIDE QUANTIFICATION OF SMALL MOLECULE BINDING TO CELLULAR TARGET PROTEINS

CROSS-REFERENCE TO RELATED APPLICATIONS

The present application is a U.S. National Stage application of PCT/EP2008/062979, filed 26 Sep. 2008, which claims the benefit of U.S. Provisional Application No. 60/977,692 filed 5 Oct. 2007, and European Application No. 07117996.4 filed 5 Oct. 2007, the entire disclosures of which are hereby incorporated herein by reference in their entirety.

FIELD OF THE INVENTION

This invention relates to methods for the evaluation and/or quantification of the binding affinity of small molecules or other compounds to target components contained within an analyte, such as target proteins contained within the proteome of a cell or tissue.

BACKGROUND OF THE INVENTION

The pharmaceutical industry today faces two fundamental challenges in its drug development to process, namely the identification of appropriate protein targets for disease intervention and the identification of high quality drug candidates which act specifically on these targets. These two challenges are of paramount importance in the design of successful medicines.

Intervention with low-molecular-weight compounds represents a fundamental therapeutic concept for the treatment of human disorders. Due to their key roles in signal transduction processes implicated in the onset and progression of severe diseases such as human cancers, various members of the protein kinase superfamily of enzymes have been extensively targeted by small molecules disrupting their catalytic functions. These drug development efforts have provided a plethora of tools for the dissection of cellular signalling by chemical genetic approaches. In contrast to classical genetic inactivation, small molecule inhibition can selectively modulate the catalytic activity of a protein kinase in a way that is rapid, tunable and, in most cases, reversible. Moreover, many protein-protein interactions formed by protein kinases are preserved in the presence of small molecule antagonists and can therefore be dissected from their catalytic functions.

Despite these obvious advantages, small molecule antagonists developed for kinase inhibition have the potential to inactivate several targets in intact cells, due to common structural features found in the catalytic domains of different protein kinases or even members from other enzyme families. The selectivity of kinase inhibitors can be assessed by parallel in vitro activity or binding assays for large numbers of recombinant protein kinases (Fabian, M. A. et al., Nat. Biotechnol. 23, 329-36 (2005); Davies, S. P. et al., Biochem. J. 351, 95-105 (2000)). This approach undoubtedly provides valuable and quantitative data about drug selectivity, but has two major limitations: First, in addition to a significant part of the protein kinase complement (=the kinome), potential targets from other enzyme classes are underrepresented or missing altogether in these screening formats. Secondly, and perhaps more importantly, the recombinant kinase collection included in a selectivity panel does not match the cellular profile of potential targets expressed in, for example, a cell system where the biological effects of a kinase inhibitor are investigated.

These shortcomings can be addressed with proteomic approaches, which employ immobilized compounds, e.g., kinase inhibitors, for the selective affinity purification of target proteins in combination with protein identification, e.g., by mass spectrometry (MS). This straightforward technique has been successfully used to identify the target components of various kinase inhibitors in cellular extracts. However, target component identification was limited in the sense that the affinities of the inhibitor towards its cellular binding partners could not be inferred from the MS data. For obtaining further quantitative information, it was necessary to resort to secondary, in vitro activity assays to identify those inhibitor targets, which were potently inhibited and therefore potentially relevant for the observed cellular drug actions. However, in practice, it is challenging to assess the whole target spectrum of a small molecule drug due to the fact that the required recombinant proteins are not all available or in vitro activity assays prove difficult to establish.

Comprehensive knowledge of the cellular proteins targeted by small molecule intervention is a pre-requisite to define chemical-biological interactions on the molecular level (Daub, H. et al., Assay Drug Dev. Technol. 2, 215-24 (2004); Fabian, M. A. et al., Nat. Biotechnol. 23, 329-36 (2005)). Although affinity purification techniques together with mass spectrometry (MS) have been successfully used to identify the interacting proteins of immobilized small molecule inhibitors, these previous proteomics approaches did not deliver information of cellular target affinities (Godl, K. et al., PNAS U.S.A., 100, 15434-9 (2003); Brehmer, D. et al., Cancer Res. 65, 379-82 (2005); Daub, H., Biochim. Biophys. Acta 1754, 183-90 (2005)).

There is therefore a need for methods of proteomics which permit the direct qualitative and/or quantitative evaluation or determination of compound-target component interactions, e.g., inhibitor-target protein interactions. There is also a need for methods of the afore-mentioned kind which can be adapted for high throughput applications.

SUMMARY OF THE INVENTION

The above objects are solved by the methods according to the present invention. By virtue of these methods, it is now possible to immediately determine the binding affinities of a target compound, such as an inhibitor, towards its cellular binding partners, either qualitatively or quantitatively, without having to resort to secondary in vitro binding or activity assays. The methods of the invention furthermore allow ranking a large number of cellular targets of an immobilized compound according to their affinities, and furthermore to assess their competitive binding properties with regard to a distinct inhibitor without further immobilization. This is exemplarily demonstrated herein on more than 100 cellular targets of kinase inhibitors. The new methods are broadly applicable and allow for the simple and rapid characterization of pharmacological and pharmacokinetic interactions and/or functions of any type of small molecules or other compound of interest in various biological systems.

Thus, in one aspect, the invention provides a method for evaluating the binding of a target component of an analyte to a compound comprising (a) contacting a first aliquot of the analyte with a solid support onto which the compound is immobilized; (b) contacting a second aliquot of the analyte with a solid support of the kind as used in step (a), subsequently separating the second aliquot of the analyte from said solid support; (c) re-contacting the separated analyte from step (b) with a solid support of the kind as used in step (a); (d) determining the amounts of the target component bound to the solid support in steps (a) and (c); and (e) comparing the amount of target component bound to the solid support in step (a) to the amount of target component bound to the solid support in step (c). Methods according to this aspect are also referred to herein as methods according to IVA2 (In Vitro Association: Setting 2).

Although not strictly mandatory, the above method may further comprise the step of contacting a third aliquot of said analyte with a solid support of the kind as used in step (a), which does not have, however, said compound immobilized onto it, and determining the amount of target component bound to said solid support. This step may serve as a negative control by which possibly unspecific binding of the target components of the analyte to the solid support as opposed to specific binding thereof to the immobilized compound of interest may be determined.

Accordingly, step (e) of the above method may further comprise comparing the amounts of target component bound to the solid support in steps (a) and (c) to the amount of target component bound to said solid support which does not have said compound immobilized onto it. Alternatively, step (e) may comprise comparing the amounts of target component bound to the solid support in steps (a) and (c) to an amount of target component unspecifically bound to the support material which amount has been previously determined or is yet to be determined in (an) independent experiment(s), or is determined by other means, such as calculation or extrapolation from preexisting data, e.g., data available from the literature, or from data yet to be obtained.

In a preferred embodiment, contacting steps (a) and (b), and preferably also the contacting step relating to the third aliquot of the above method are performed simultaneously. Alternatively, contacting step (a) and re-contacting step (c), and preferably also the contacting step relating to the third aliquot of the above method may be performed simultaneously.

In a further, related aspect, the invention provides a method for evaluating the binding of a target component of an analyte to a compound comprising (a) contacting a first aliquot of the analyte with a solid support onto which the compound is immobilized; (b) contacting a second aliquot of the analyte with a solid support of the kind as used in step (a) onto which said compound is, however, immobilized at a higher concentration than in (a); (c) contacting a third aliquot of the analyte with a solid support of the kind as used in step (a) onto which said compound is, however, immobilized at a higher concentration than in (b); (d) determining the amounts of target component bound to the solid support in steps (a), (b) and (c); and (e) comparing the amounts of target component bound to the solid support in steps (a), (b) and (c). Methods according to this aspect are also referred to herein as methods according to IVA1 (In Vitro Association: Setting 1).

It will be appreciated that step (c) of the above method is not strictly mandatory, since the method provides useful qualitative and also quantitative information on the binding affinity even in the absence of the optional step (c). In a preferred embodiment of the invention, the methods according to IVA1 do, however, contain a step (c) as defined above.

Also in respect of this aspect of the invention, it may be useful to additionally include a negative control, although this is again not strictly mandatory. Thus, the method may comprise the step of contacting a fourth aliquot of said analyte with a solid support of the kind as in step (a) which, however, does not have said compound immobilized onto it, and determining the amount of target component bound to said solid support. This allows to determine possibly unspecific binding of the target component to the solid support as opposed to specific binding of the target component to the compound of interest immobilized onto said support.

Accordingly, step (e) of the method according to IVA1 may additionally comprise comparing the amounts of target component bound to the solid support in steps (a), (b) and (c) to the amount of target component bound to said solid support which does not have said compound immobilized onto it. Alternatively, step (e) may comprise comparing the amounts of target component bound to the solid support in steps (a), (b) and (c) to an amount of target component unspecifically bound to the support material, wherein this amount has been previously determined or is yet to be determined in (an) independent experiment(s), or is determined by other means, such as calculation or extrapolation from preexisting data, e.g., data available from the literature, or from data yet to be obtained.

In a preferred embodiment of this aspect, the contacting steps (a), (b) and (c) and preferably also the contacting step relating to the fourth aliquot of the above method are performed simultaneously. Alternatively, contacting steps (a), (b) and (c) and preferably also the contacting step relating to the fourth aliquot of the above method may be performed consecutively.

It will be appreciated that the methods of the present invention according to IVA1 or IVA2 described and/or claimed herein may be combined. Specifically, the binding of a target component of an analyte to an immobilized compound may first be determined or evaluated by a method according to IVA1, and subsequently, it may additionally be evaluated by a method according to IVA2.

In yet a further, related aspect, the invention provides a method for evaluating the binding of a target component of an analyte to a competitor compound comprising (a) contacting a first aliquot of the analyte with a solid support onto which a compound is immobilized which binds to the target component with a given binding affinity, wherein the contacting is performed in the presence of said competitor compound; (b) contacting a second aliquot of the analyte with a solid support of the kind as used in step (a) in the presence of said competitor compound, wherein the concentration of said competitor compound is higher than in step (a); (c) contacting a third aliquot of the analyte with a solid support of the kind as used in step (a) in the presence of said competitor compound, wherein the concentration of said competitor compound is higher than in step (b); (d) determining the amounts of target component bound to the solid support in steps (a), (b) and (c); and (e) comparing the amounts of target component bound to the solid support in steps (a), (b) and (c). Methods according to this aspect are also referred to herein as IVA (In Vitro Association) competitor methods.

It will be appreciated that step (c) of the above method is not strictly mandatory, since the method provides useful qualitative and also quantitative information on the binding affinity even in the absence of the optional step (c). In a preferred embodiment of the invention, the IVA competitor methods do, however, contain a step (c) as defined above.

It will also be appreciated that according to this aspect of the invention, the given binding affinity with which the immobilized compound binds to the target component may be a predetermined binding affinity. In a preferred embodiment, the binding affinity, e.g., a $K_d$ value, is determined, or has been determined, by any of the methods of the present invention according to IVA1 and/or IVA2.

Alternatively, the given binding affinity with which the immobilized compound binds to the target component may also be a binding affinity which has been previously determined or is yet to be determined in (an) independent experiment(s), or is determined by other means, such as calculation or extrapolation from preexisting data, e.g., data available from the literature, or from data yet to be obtained.

An IVA competitor method of the invention may further comprise the step of contacting a fourth aliquot of said analyte with a solid support of the kind as used in step (a) onto which said compound with said given binding affinity is immobilized, wherein the contacting is, however, performed in the absence of said competitor compound. In this case, step (e) of the method preferably further comprises comparing the amounts of target component bound to the solid support in steps (a), (b) and (c) to the amount of target component bound to said solid support in the absence of said competitor compound.

According to any of the methods of the invention described herein, the target components in the analyte are preferably labelled with a detectable label. While the detectable label may be the same in each aliquot, the detectable label is preferably different in each aliquot, i.e., the target components in the first aliquot have a label which is different from the target components in the second aliquot and so on. This can be easily achieved by direct labelling of the aliquots with different detectable labels, or in the case of analytes, which are derived from tissue, tissue culture, cells, cell culture, or body fluids, by metabolic labelling in vivo or in culture using different detectable labels.

In case different detectable labels are used to label the target compounds in the different aliquots used in the methods of the invention, the determination of step (d) according to any of the methods of the invention is advantageously done by combining said bound target components into one sample and detecting the amounts of differently labelled target components in said sample. In this regard, it may be advantageous to elute the target components from the solid support prior to combining them into said sample.

It will be appreciated that the comparison according to step (e) of any of the methods of the invention may be used to qualitatively and/or quantitatively determine or calculate the binding affinity of the target component to the compound.

It will also be appreciated that by virtue of the methods according to the invention the binding of a multitude of target components found within an analyte to the immobilized compound and/or the competitor compound may be simultaneously evaluated and determined.

It will furthermore be appreciated that the methods according to the invention are particularly suited to be applied to high throughput screening approaches. Thus, in another embodiment of the invention the methods described and/or claimed herein are performed in whole or at least in part in a high throughput manner.

BRIEF DESCRIPTION OF THE DRAWINGS

FIG. 1: Schematic representation of preferred methods according to the invention.
(a) IVA1 (In vitro Association: Setting 1)—Quantification of dose-dependent binding of cellular target proteins to an immobilized small molecule inhibitor
(b) IVA2 (In vitro Association: Setting 2)—Certain shortcomings of IVA1 resolved by two parallel rounds of consecutive affinity purification at the highest ligand density and an additional incubation with control beads devoid of immobilized inhibitor.
(c) Control experiment to verify that the immobilised ligand is present in molar excess over its target proteins in the analysed biological extract.

(b) Lysates from SILAC-encoded cells were incubated with AX14596 beads in the presence of different gefitinib concentrations. Bound protein fractions were combined as indicated and quantitatively assessed in parallel LC-MS experiments. The $IC_{50}$ values for gefitinib-dependent protein displacement from the AX14596 resin were determined and then used to calculate target-specific dissociation constants for gefitinib.

Figure 4:
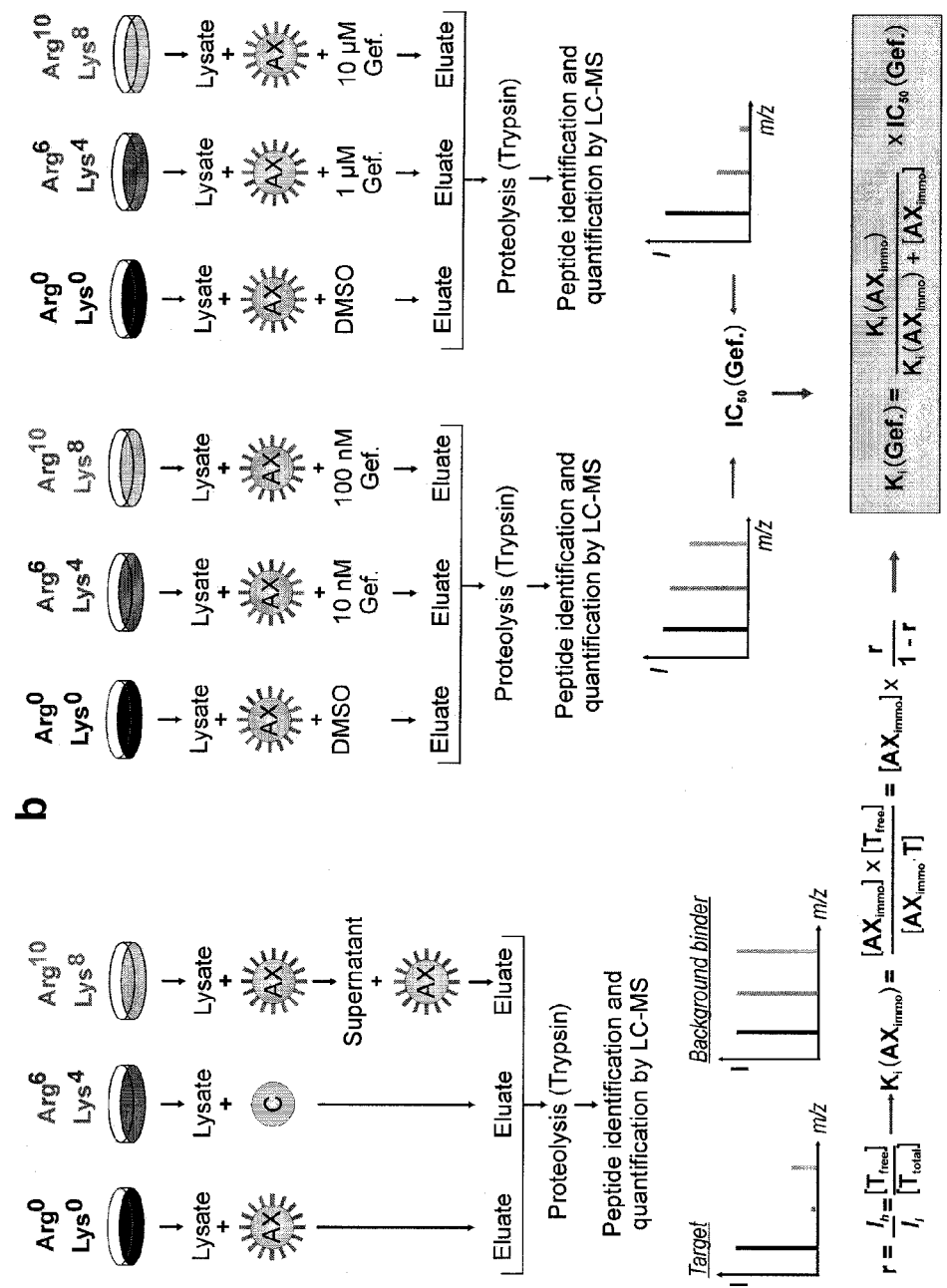
FIG. 4: Assessment of target-specific dissociation constants by quantitative chemical proteomics.
(a) HeLa cells were SILAC-encoded with normal or stable isotope-labeled arginine and lysine. Cell lysates were prepared and incubated with control resin (C) or subjected to either one or two in vitro associations with AX14596-containing beads (AX). The three elution fractions were pooled and analyzed by quantitative LC-MS to identify specific binders and to determine unbound (=r) and bound target (1-r) fractions. The ratios thereof multiplied with the concentration of AX14596 equals the target-specific dissociation constants (=Ki) for immobilized AX14596, as binding equilibria were reached in the presence of a molar excess of capture molecules and Mg2+-ATP complexes were disrupted due to the presence of chelating agents.

FIG. 5: Cellular kinase panel for quantitative inhibitor profiling.

a) The binding affinities of cellular target components for the immobilized, unselective kinase inhibitor VI16742 were determined according to the strategy outlined in FIG. 4. VI16742-interacting protein kinases from HeLa cells are marked in the dendrogram of the human kinome. The size of the red circles indicates the respective binding affinities. MS spectra of representative peptides and the determined Ki values are shown for several VI16742 kinase target components. The kinase dendrogram was adapted with permission from Cell Signaling Technology.

(b) Concentration-dependent inhibition of protein kinase binding to the VI16742 resin by SB203580. The $IC_{50}$ values determined in the competition experiments and the resulting Ki values are shown for cellular targets of SB203580.

FIG. 6: Correlation of quantitative target binding data for replicate analyses.

(a) Experimental outline. HeLa S3 cells were SILAC-encoded with normal arginine and lysine (Arg0/Lys0) or stable isotope-substituted variants (Arg6/Lys4, Arg10/Lys8) prior to cell lysis. In the normal labeling scheme, Arg0/Lys0-encoded protein extracts were subjected to one incubation step with the inhibitor beads (I), while Arg10/Lys8-labeled lysate underwent two consecutive in vitro associations. The Arg0/Lys0- and Arg10/Lys8-encoded lysates were switched in a cross-over experiment with an inverse labeling scheme. The cross-over experiment verified the reproducibility of the specific target binding and provided an effective means to eliminate false-positive target identification. The latter can be due to the presence of small amounts of contaminating protein species, which are not of cellular origin and are therefore only identified through Arg0 and/or Lys0 labeled peptide species. This is important, as specific targets of very high affinity would result in a similar SILAC pattern in the "normal" labeling scheme. To account for unspecific background binding, Arg6/Lys4-labeled cell lysates were incubated with control resin (C). After the in vitro association steps, resin-bound proteins were eluted and analyzed by quantitative LC-MS.

(b) Illustration depicting how in the normal labeling scheme peptide ion intensities specify the percentage of target protein retained by affinity purification with a kinase inhibitor resin. Considering, for example, a high-affinity target of which 90% is retained by the immobilized inhibitor and 10% remains unbound in the supernatant fraction, then 9% (90% of 10%) of the initial target population binds to the affinity resin when the supernatant is subjected to the same amount of immobilized inhibitor in a second in vitro association step. The resulting target ratio r=0.1, as determined by SILAC-enabled quantification of the relative abundances of target-derived peptides, indicates which fraction of the target is not retained by the affinity resin. Consequently, 1-r=0.9 represents a measure for the target fraction that binds to the inhibitor beads.

(c,d) Ratios of target protein amounts retained in the second versus the first round of binding to AX14596 (a) or VI16742 (b) beads are compared for the SILAC experiments done according to the inverse (x axis) and normal (y axis) labeling scheme. The dotted lines indicate maximum correlation between the replicate experiments.

Figure 7:
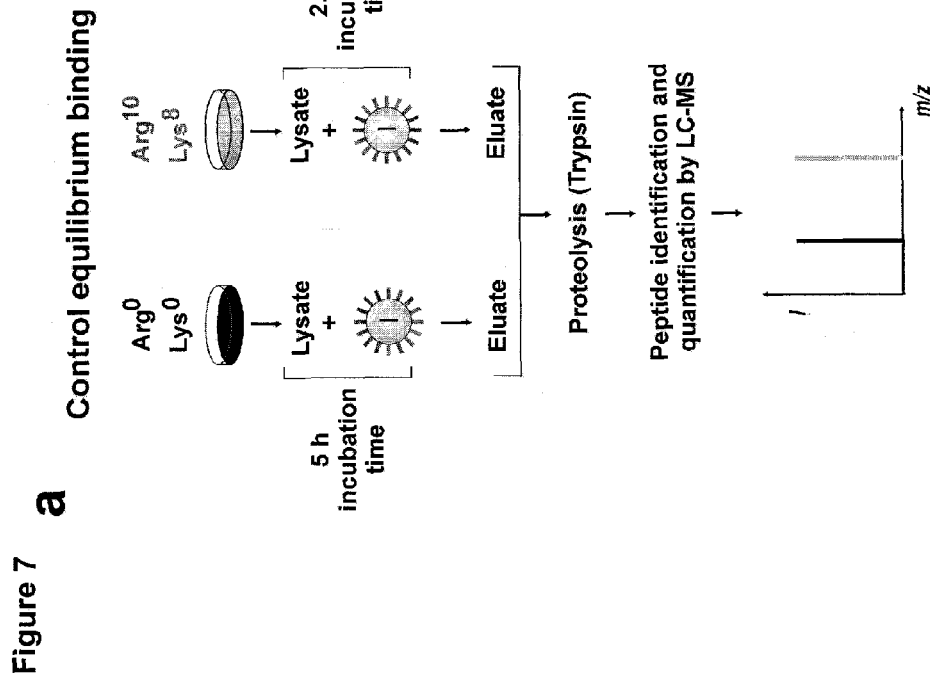

FIG. 7: Analysis of target protein binding over time.

(a) To verify that target binding reactions have reached equilibrium within the 2.5 hours of incubation used throughout this study, differentially SILAC-encoded lysates were subjected to either 5 hours or 2.5 hours of in vitro association in the presence of beads containing immobilized inhibitor. Elution fractions were combined and analyzed by quantitative LC-MS.

(b,c) The ratios of resin-bound target after 5 h versus 2.5 h were determined and plotted against the log 10 transformed values of the target dissociation constants for either immobilized AX14596 (b) or VI16742 (c). The majority of plotted values were close to a vertical line intersecting the x axis at a ratio of 1, indicating conditions close to equilibrium binding for the AX14596 (b) or VI16742 (c) resins.

FIG. 8: Control experiments to determine whether the concentration of immobilized inhibitor is present in molar excess over its cellular target proteins.

(a) SILAC experiments were performed in which either 3 mg or 1 mg of cellular protein was subjected to inhibitor affinity resin in the same incubation volume. Eluates from the two parallel incubation reactions were pooled and analyzed by quantitative LC-MS.

(b,c) Ratios of resin-associated target proteins bound from 3 mg compared to 1 mg of cell extracts were determined and plotted against the log 10 transformed values of the target dissociation constants for either immobilized AX14596 (b) or VI16742 (c). Protein ratios close to three indicated that the effective concentration of the immobilized kinase inhibitors was not a limiting factor in the binding assay.

FIG. 9: Correlation of target binding data in replicate analyses of competition experiments.

(a) Competition assays including inhibitor beads and different concentrations of "free" kinase inhibitors were done in replicate analyses, in which the free inhibitor was either added 30 min prior (experiment 1) to or 30 min after the addition (experiment 2) of inhibitor affinity beads. The second incubation step was performed for 2.5 h prior to target protein elution and quantitative LC-MS.

(b,c) The $IC_{50}$ values for the free inhibitor target components were determined separately based on the competition data from experiments 1 and 2. The ratio of these $IC_{50}$ values was $\log_2$ transformed and plotted against the $\log_{10}$ transformed ratios of the calculated target affinities ($K_i$ values) for either gefitinib (b, tested against the AX14596 resin) or SB203580 (c, tested against the VI16742 resin). Similar target component distributions between the stationary and soluble phase in experiments 1 and 2 were evident from $\log_2$ transformed $IC_{50}$ ratios being close to zero. Therefore, in addition to demonstrating the reproducibility of the competition assays, the reversibility of the target component—compound (inhibitor) interaction was verified indicating that binding equilibria have been reached in the competition assays.

FIG. 10: Chemical structure of VI16742 and Gene Ontology (GO) analysis of resin-bound proteins.
  (a) The functional group for covalent immobilization of VI16742 is encircled.
  (b) Significantly over-represented GO molecular function terms (P<0.001) for all quantified proteins retained by VI16742 affinity beads and the subset of proteins characterized as specific inhibitor target components. Over-representation of GO terms such as protein kinase and lipid kinase activity was far more pronounced in the specific target fraction compared to all inhibitor resin-bound proteins.

Figure 11:
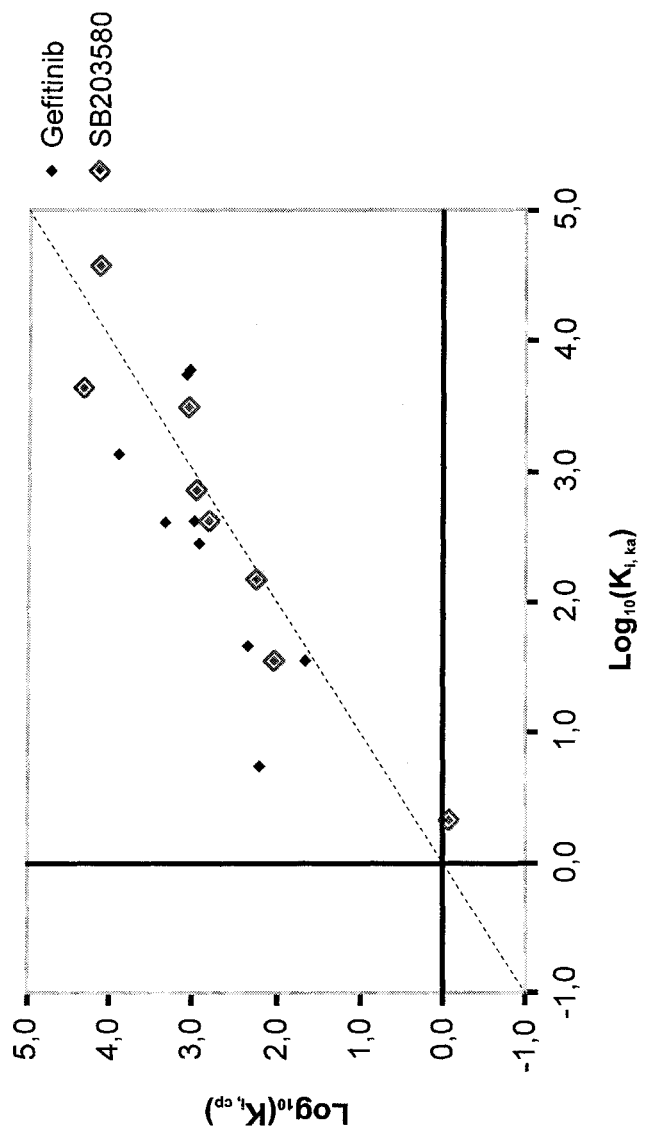

FIG. 11: Comparison of chemical proteomics data with results from in vitro kinase assays.
  The $K_i$ values determined for cellular gefitinib and SB203580 targets by chemical proteomics (Ki,cp) were log 10 transformed and plotted against the log 10 transformed $IC_{50}$ values for gefitinib (dark grey dots) and SB203580 (light grey dots) from in vitro inhibition assays with recombinant protein kinases (Ki,ka) (Table 6). Due to the use of sub-micromolar ATP concentrations, the $IC_{50}$ values from the enzymatic assays represented a close approximation of the actual $K_i$ values. These results indicate a better correlation of chemical proteomic analysis and enzymatic activity assays in comparison to the data reported for a previously published chemical proteomics approach (data not shown) (Bantscheff, M. et al. Quantitative chemical proteomics reveals mechanisms of action of clinical ABL kinase inhibitors. *Nat Biotechnol* 25, 1035-1044 (2007)).

Figure 12:
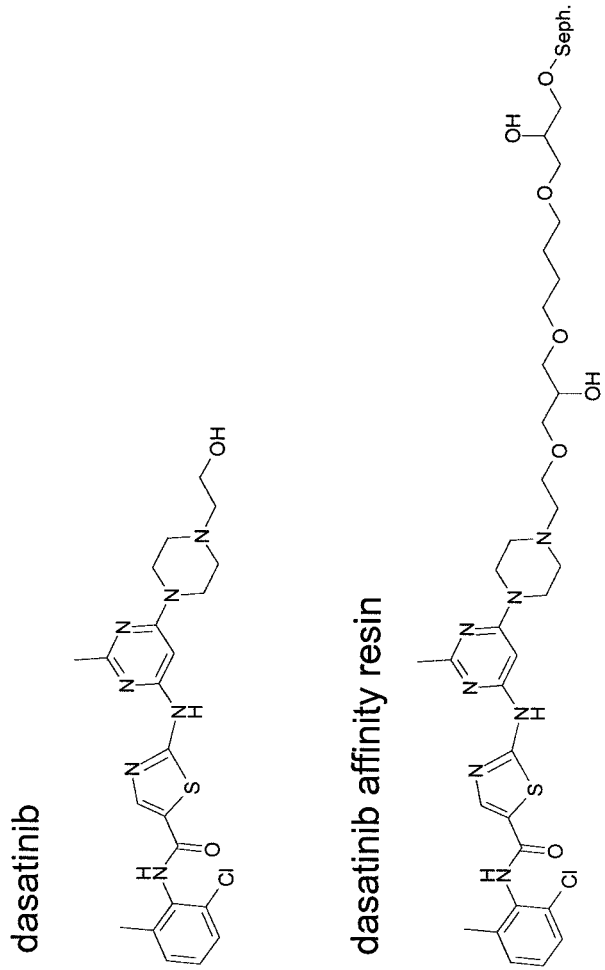

FIG. 12: Structure of dasatinib and the corresponding immobilized dasatinib affinity resin.

Figure 13:
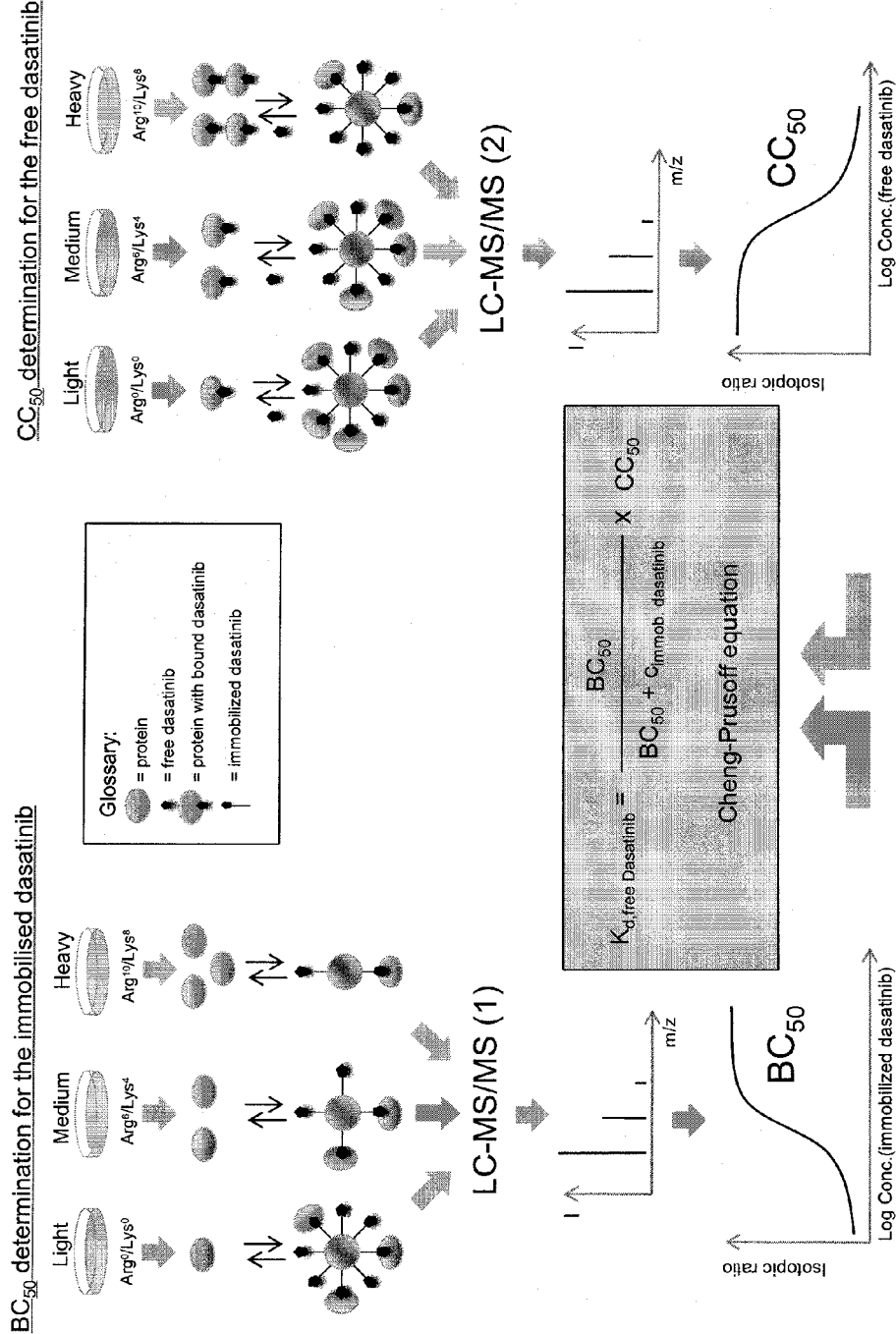

FIG. 13: Target affinities for free dasatinib in solution.
  Target affinities were determined for the free Dasatinib in solution. K562 cells were grown in the presence of normal and two different forms of stable isotope labelled amino acids (SILAC). Differentially labelled cell lysates were incubated (left side) with dasatinib affinity beads having different concentrations of covalently immobilized dasatinib and (right side) with dasatinib affinity beads having the highest ligand density in the presence of increasing concentrations of free dasatinib. Proteins bound to the immobilized dasatinib were eluted and analyzed by quantitative LC-MS/MS. Relative protein ratios determined for the various samples allowed the calculation of $K_d$ values for the free dasatinib ($K_{d, free\ dasatinib}$) using the Cheng-Prosoff equation.
  $BC_{50}$ indicates the concentration of immobilized dasatinib that allows 50% target protein binding. $CC_{50}$ indicates the concentration of free dasatinib that inhibits 50% target protein binding to the immobilized dasatinib. The term $c_{immob.\ dasatinib}$ represents the concentration of immobilized dasatinib used in the competition experiments for $CC_{50}$ determination.

FIG. 14: Table of dasatinib target proteins determined from K562 cell extracts and their corresponding Kd values.

DETAILED DESCRIPTION OF THE INVENTION

The term "analyte" as used herein may be a proteome, a mixture of different proteomes, a cell lysate or extract, a tissue lysate or extract, a cell culture supernatant, a tissue culture supernatant, or a body fluid, such as milk, liquor or lymph.

The term "proteome" as used herein refers to the specific protein composition of a cell, tissue or organism. Depending on the individual cells contained therein, a culture of a cell or a tissue could, theoretically, contain as many proteomes as there are cells contained therein. For convenience, the proteomes of one cell culture or one tissue is regarded as representing one proteome. The proteomes of one type of organism may differ from another depending on the status and genomic background of its cells.

For the purposes of the present invention, a variety of proteomes can be used as analytes. Such proteomes may be derived from single cells or cell cultures made from a homogeneous population of cells or from a mixture of cells. They may also be derived from a tissue, organ or organism. Moreover, the said single cell, cell culture or mixture of cells, tissue, organ or organism may be exposed to certain conditions, such as heat, stress, starvation, drugs, radioactivity, chemical agents, toxins, viral infection, antibiotics, and ageing. These conditions lead to different "sets" of proteomes that can also be used as analytes in the methods of the invention and compared to each other in terms of the binding of the target components contained therein to a given compound of interest. These proteomes thus reflect a situation that resembles the situation in vivo as closely as possible.

The proteomes to be used as analytes according to the invention may be derived from prokaryotic or eukaryotic cells, such as bacterial cells, pathogenic micro-organisms, fungal cells, yeast cells, plant cells, mammalian cells, fish cells, nematode cells, insect cells, and, in particular, stemcells, such as embryonic or adult stem cells, e.g., non-human embryonic or adult stem cells. Furthermore, the methods of the invention can be applied to a large variety of proteomes that are present in or derived from a tissue or organ, such as connective tissue, endothelial tissue, brain, bone, liver, heart, skeletal muscles, prostate, colon, kidney, glands, lymph nodes, pancreas, roots, leaves, and flowers. Finally, suitable proteomes can be those present in a non-human organism or derived from an organism, such as *E. coli, Drosophila melanogaster, Caenorhabditis elegans*, zebrafish, rat, hamster, mouse, goat, sheep, monkey, human, and jellyfish, or a plant organism such as rice, potato, *Arabidopsis*, wheat, oat, and tobacco.

As used herein, a "target component" may be any component within an analyte which is capable of interacting, e.g., binding, to the compound of interest. A target component could thus be, e.g., an oligo- or polysaccharide, a nucleic acid, a proteoglycan, a peptide, or a protein, which includes glycoproteins. In a preferred embodiment, the target component of the analyte according to the invention is a protein. Preferably, the protein is a kinase, and more preferably a protein kinase. In an equally preferred embodiment, the target component is a lipid kinase.

The compound immobilized onto the solid support or the competitor compound according to the present invention may be any compound of interest selected from enzymes, polypeptides, peptides, antibodies and fragments thereof, oligo- or polysaccharides, proteoglycans, chemical entities, small molecules, drugs, metabolites, or prodrugs. Preferably, the compound or competitor compound is an inhibitor of the target component in the analyte.

Preferred examples of such compounds or competitor compounds are synthetic and/or naturally occurring chemical compounds, small molecules, peptides, proteins, antibodies, and the like.

It will be understood that, in accordance with the present invention, the compound and the competitor compound may be the same or may be different from each other.

The term "small molecule" as used herein refers to molecules that exhibit a molecular weight of less than 5000 Da, more preferred less than 2000 Da, even more preferred less than 1000 Da and most preferred less than 500 Da. Such compounds can be suitable "leads" for further optimization.

Compounds or competitor compounds that are synthetic and/or naturally occurring "small molecule" compounds, e.g. drugs, metabolites, prodrugs, potential drugs, potential metabolites, potential prodrugs and the like, are preferred for use in the methods described and claimed herein. Preferably, said compounds or competitor compounds are selected from the group consisting of synthetic or naturally occurring chemical compounds or organic synthetic drugs, more preferably small molecules, organic drugs or natural small molecule compounds.

In a preferred embodiment of the methods of the invention, the target component is a kinase and the immobilized compound of interest, and the competitor compound, is a kinase inhibitor.

However, also comprised in the present invention is the use of compounds or competitor compounds that are nucleic acids, such as a DNA, RNA and/or PNA (protein nucleic acid). Such nucleic acids can be present in the form of oligonucleotides or polynucleotides, including nucleic acids comprising specific nucleotide sequences and/or motifs. Hybrids between the different forms of nucleic acids may also be used.

The term "solid support" as used herein relates to any undissolved support capable of immobilizing the above spectrum of compounds of interest on its surface. Materials that can be used as solid support are many, and include, but are not limited to, fused silica, quartz, silicon, plastics, glass, gold, metals, transparent electrodes (e.g., indium tin oxide or related materials), ceramics (e.g., metal oxides), paper, conductive carbon, conductive polymers, filters, glass slides, silicon surfaces, beads and a customized chemical microarray. Such suitable materials may take the form of small beads, pellets, disks, chips, dishes, multi-well plates, wafers or the like, although other forms may be used as well.

In a preferred embodiment of any of the methods of the present invention, the compounds are bound to beads, such as sepharose (e.g., NHS-activated sepharose) or agarose beads. In a particularly preferred embodiment, said beads are sepharose, optionally epoxy-activated or NHS-activated, or agarose beads. For example, an inhibitor compound (such as V16742, FIG. 2a) can be coupled to epoxy-activated Sepharose beads at three different concentrations and the relative concentration of covalently immobilized inhibitor on the distinct resins is determined by spectrophotometry (here 1-, 5- and 25-fold of the lowest concentration).

Suitable solid support material may also comprise or consist of ferro- or ferrimagnetic particles as known, e.g., from WO 01/71732, incorporated herein by reference as far as properties of ferro- or ferrimagnetic particles are concerned. The ferro- or ferrimagnetic particles may comprise glass or plastic. The ferro- or ferrimagnetic particles that can be used in the context of the present invention may be porous. The ferro- or ferrimagnetic glass particles may comprise about 30 to 50% by weight of $Fe_3O_4$ and about 50 to 70% by weight of $SiO_2$. Useful ferro- or ferrimagnetic particles preferably have an average size of about 5 to 25 µm in diameter, more preferably about 6 to 15, µm, and particularly about 7 to 10 µm. The total surface area of the ferro- or ferrimagnetic particles may be 190 g/m or greater, e.g., in the range of about 190 to 270 g/m (as determined according the Brunaur Emmet Teller (BET) method).

These magnetic particles facilitate purification, separation and/or assay of biomolecules, like protein kinases. Magnetic particles (or beads) that bind a molecule of interest can be collected or retrieved by applying an external magnetic field to a container comprising the particles.

Immobilization of the compounds onto the solid support material can be achieved by adsorption, absorption, ionic bonding, covalent bonding, an amino-group or carboxy-group or hydroxy-group, (strept)avidin-biotin, or thiol-gold interactions and any other method that can attach the materials at a controllable density or concentration.

The immobilized compound is preferably present in a defined concentration on the solid to support. Preferred concentrations or concentration ranges in this regard are concentrations from about 30 nM to about 10 mM, preferably from about 100 nM to about 10 mM, or from about 1 µM to about 5 mM.

In a preferred embodiment of any of the methods of the invention, the compound is covalently coupled to the solid support. Before coupling, the solid support material or matrix can contain active groups such as NHS, carbodimide etc. to enable the coupling reaction with compounds. The compounds can be coupled to the solid support by direct coupling (e.g. using functional groups such as amino-, sulfhydryl-, carboxyl-, hydroxyl-, aldehyde-, and ketone groups) and by indirect coupling, e.g., via biotin, biotin being covalently attached to the compound and non-covalent binding of biotin to streptavidin which is bound to solid support directly.

The biotin-avidin affinity pair is the single most exploited affinity sequestering and separating technique for biological applications. The system is based on immobilizing avidin, streptavidin or neutravidin on a solid support. A biotinylated bait molecule is mixed with a cell lysate. This mixture is then loaded on the avidin-based affinity column and washed to elute non-specific binding proteins. The desired protein can then be released by washing with several available reagents. A substantial amount of work indicates that monomeric neutravidin can be used to minimize nonspecific interactions with common proteins. Furthermore many chemical reagents are readily available which allow the biotinylation of small molecules having specific functional groups.

In a preferred embodiment of any of the methods of the invention, the compound is immobilized onto the solid support material, particularly beads, via an amino-group, a hydroxy-group or a carboxy-group.

While not mandatory, it may be useful to immobilize the compound onto the solid support material via a linker or spacer. For attaching compounds to the solid support several tethering systems can be used. For example, covalent linkers between compound and solid support can be employed. Combinatorial techniques may be used to optimize factors such as linker type, rigidity and length optimal for protein binding, whilst minimizing unwanted non-specific interactions. Suitable systems and techniques for optimizing them are known to those skilled in the art.

In the context of the present invention, the term "contacting" includes all measures or steps which allow interaction between the analyte and the solid support. The contacting is performed in a manner so that the target components in the analyte can interact or bind to the immobilized compound. The binding between target component and the compound will preferably be non-covalent, reversible binding, e.g., binding via salt bridges, hydrogen bonds, hydrophobic interactions or a combination thereof.

The methods of the present invention allow for direct qualitative and/or quantitative evaluation or determination of the interaction of a compound of interest with target components in an analyte, such as a cell or tissue lysate or extract.

In a first aspect of the invention, also referred to herein as method according to IVA1 (In Vitro Association, Setting 1), the immobilization of the compound of interest onto the solid support is done in different concentrations in combination with different parallel or consecutive affinity purification steps, such as contacting steps (a), (b), and (c) mentioned above, which allow to determine the affinity of the target component to said compound.

Various ratios of the concentrations in which the compound of interest is immobilized onto the solid support are suitable in the context of this aspect of the invention. Preferred ratios of the concentrations in the above-mentioned steps (a), (b) and (c) are selected from the ratios of about 1:5:25 or about 1:10:100. However, other ratios are likewise suitable, for example ratios of about 1:3:9, about 1:4:16, about 1:6:36, about 1:7:49, about 1:8:64 or about 1:9:81.

By determining the amount of target component bound to the solid support in steps (a), (b) and (c) and comparing the amounts of target component bound to the solid support in these steps, the method allows to qualitatively and, to a certain extent, to quantitatively determine the affinity of the binding of the target component in the analyte to the compound of interest.

In the methods according to IVA1, the amount of target component bound to the solid support is reflected, e.g., by the signal intensities determined in step (d), measured, e.g., by MS. Increasing amounts of target component bound to the compound in steps (a), (b) and (c), as reflected by increasing signal intensities, indicate that the target component may be one with only low or medium binding affinity for the compound bound to the solid support. Only small increases in the amounts of target component bound to the compound in steps (a), (b) and (c), as reflected by rather similar signal intensities, are indicative for target components with high binding affinity for the compound bound to the solid support. If the amounts of target component bound to the compound in steps (a), (b) and (c) are equal, which may be visualized by equal signal intensities, this may be indicative for either very strong binding to the compound bound to the solid support or unspecific binding to the solid material.

For accurate determination of Kd values with the methods according to IVA1, the concentration of the immobilized inhibitor should preferably be in molar excess of the concentration of its corresponding target component(s) in the analyte, preferably in at least two-fold molar excess. However, even under conditions in which the concentration of immobilized ligand is limiting, the assay will still rank different target components according to their affinities for the immobilized ligand. Therefore, a molar excess of ligand is desirable and an optional requirement, but not essential.

The above aspect of the invention is exemplarily demonstrated in FIG. 1a (IVA1, In vitro Association, Setting 1). A method according to this aspect is preferably performed by using cell lysates from three cultures of the same cells, which differ, however, in that they have been metabolically labeled with different isotope labelling. These differently labelled lysates are processed in the method as separate aliquots of the same analyte. Specifically, they are contacted with an inhibitor compound of interest (in the Figure V16742 is used) immobilised at different concentrations onto a solid support (in the Figure in a ratio of 1:5:25). After in vitro association with the ligand, the proteins of each aliquot bound to the solid support are combined and analyzed by LC-MS/MS. Subsequently, the relative abundance of interacting proteins may be quantified by determining the intensity ratios of the isotope labelled peptide ions derived from the three parallel incubations (FIG. 1a).

It will be appreciated that according to the above aspect of the invention, certain qualitative, but also quantitative determinations may be made regarding the affinity of the target component to the compound of interest.

As schematically shown in the Figure for a representative target component retained with low or medium affinity to V16742, the intensities reflect increased target component binding from lower to higher concentrations of the immobilized inhibitor compound (FIG. 1a-ii).

From this experiment, it cannot be deduced with certainty, however, what percentage of a cellular target component is retained at the highest concentration of the immobilized inhibitor compound and therefore it may be difficult to determine a $K_d$ value (dissociation constant) for the inhibitor-target component interaction (FIG. 1a-ii).

In case of target components with high affinity, which are already depleted from the analyte at medium inhibitor concentration, the intensity does not increase further with more inhibitor present on the affinity beads (FIG. 1a-iii). If signal intensities (representing relative target component amounts) are equal for all three in vitro associations, this could, however, either be due to target component binding with very high affinity or indicate "background" binding of a target component, which is retained through weak, unspecific interactions with the solid support material (FIG. 1a-iv).

In another aspect of the invention, also referred to herein as method according to IVA2 (In Vitro Association, Setting 2), a method is provided that allows distinguishing between these two possible scenarios. This method comprises performing two rounds of consecutive in vitro association steps of a target component within an analyte with a compound immobilized onto a solid support at a high concentration (e.g., the highest concentration used or determined in a method according to the first aspect of the invention) and comparing the amount of target component bound in the second round of these steps to the amount of target component bound in a parallel in vitro association with only one association step (FIG. 1b-i).

According to this method, again cell lysates from three cultures of the same cells which differ, however, in their metabolic isotope labelling are used, which lysates are again processed as separate aliquots of the same analyte. A first aliquot is contacted with the solid support with the compound of interest (here: V16742) immobilized at a high concentration. After allowing in vitro association, the supernatant is separated from the solid support and re-contacted with solid support material of the kind as mentioned above with the compound immobilized at a high concentration. The method also includes contacting a second, differently labelled aliquot with the above-mentioned kind of solid support material with the compound immobilized at a high concentration. A negative control, with a third, yet differently labeled aliquot contacted with the solid support which is, however, devoid of the above compound immobilized to it is run in parallel. The proteins from the first and the third aliquot bound to the solid support, and the proteins of the second aliquot bound to the solid support in the re-contacting step are combined, analyzed by LC-MS/MS and the relative abundance of interacting proteins is quantified by determining the intensity ratios of the isotope labelled peptide ions derived from the three parallel incubations (FIG. 1b).

In contrast to weakly interacting target components of the analyte, target components with a higher affinity for the immobilised compound, e.g., an inhibitor compound, are mostly depleted in the first contacting step to which the second aliquot is subjected.

By quantitative comparison with the differentially labelled target components retained from the supernatant in the second round of affinity purification with the same solid support having a compound immobilized onto it, e.g., inhibitor beads, the percentage of target component binding at the highest inhibitor compound concentration can now be calculated (examples for 10% and 75% of binding given in FIG. 1b-ii and FIG. 1b-iii, respectively). The enrichment factor for each target specifically bound to the V16742 affinity resin can be calculated according to the formula $E_n=(1-r_n)\times 100$ where, $r_n$ represents the ratio of the binding observed for the $n^{th}$ target in round 2 versus round 1 of the IVA2 setting with V16742 affinity resin and $E_n$ is the percent enrichment factor for the $n^{th}$ target.

In addition, the use of solid support having no compound bound to it, i.e., a control, provides a means to identify those target components of the analyte, which do not specifically interact with the immobilized compound (FIG. 1b-iv).

In order to allow the determination of binding affinities by the methods of the invention according to IVA2, the compound immobilized onto the solid support should be present during the contacting steps in molar excess compared to the target component.

In the methods according to IVA2, the amount of target component bound to the solid support is reflected, e.g., by the signal intensities determined in step (d), measured, e.g., by MS. Decreasing amounts of target component bound to the compound in steps (a) and (c) are reflected by decreasing signal intensities. The degree of decrease is indicative for the binding affinity of the target component to the compound bound to the solid support. If there is only a small difference (decrease) in the amounts bound in steps (a) and (c), this indicates low affinity binding, while a large difference (decrease) indicates that the target component binds with medium or high affinity to the compound bound to the solid support. If the amounts of target component bound to the compound in steps (a), (b) and (c) are equal, this is indicative of background or unspecific binding.

For rather accurate determination of Kd values, the concentration of the immobilized inhibitor is preferably in an at least two-fold molar excess over the concentration of its target component(s) in the analyte. However, even under conditions in which the concentration of immobilized ligand is limiting, the assay will still rank the target components according to their affinities for the immobilized ligand. Therefore, a molar excess of ligand is desirable and an optional requirement, but not essential.

An additional control experiment can be performed to confirm that the immobilized compound, is not limiting in the IVA methods of the invention. As shown in FIG. 1c-i, differentially labeled (e.g., SILAC encoded) cell lysates (e.g., from HeLa cells), preferably of the same volume, containing different amounts of cellular protein can be incubated with beads of the kind used according to IVA1 or IVA2, e.g., the beads containing the lowest concentration of immobilized ligand. If the ratio of signal intensities derived from ligand-interacting target proteins corresponds to the ratio of the initial protein concentrations, it can be concluded that the immobilized ligand concentration has been present in molar excess over its target proteins in the binding assay.

In a third aspect of the invention, also referred to herein as IVA (In Vitro Association) competitor method, the binding affinity of a competitor compound of interest may be determined for any target component in an analyte in respect of which the binding affinity (e.g., in terms of a $K_d$ value) of an immobilized compound (e.g., an immobilized inhibitor) has been, or will be, determined via concentration dependent competition. The binding affinity of the immobilized compound may, for instance, be determined by any of the methods of the invention according to IVA1 and/or IVA2. An advantage of this method is that the competitor compound does not have to be immobilized in this method.

The incubation time in the contacting steps according to any of the methods of the invention (i.e., either methods according to IVA1 or IVA2, or the IVA competitor methods) should preferably be long enough to reach binding equilibria for target-inhibitor interactions. The inventors have experimentally verified that this is typically the case after an incubation time of 2.5 h. However, binding equilibria may also be reached within shorter incubation times. The concentrations of buffer, salts, and other components such as chelating agents such as EDTA and EGTA or additional co-factor can in principle be varied over a large concentration range. Moreover, the contacting steps may be done at different temperatures. Preferred temperatures are selected from about 4° C., about 15° C., room temperature, about 25° C., about 37° C., and about 42° C., with about 4° C., room temperature, and about 37° C. being particularly preferred.

The contacting steps according to any of the methods of the invention are preferably performed under physiological or essentially physiological conditions. This allows to mimic the situation in vivo as closely as possible. The possibility to work under physiological or essentially physiological conditions is one of the advantages of the methods of the present invention, in contrast to other methods according to the state of the art that easily result in false positive results. The contacting is preferably performed using a suitable buffer and, optionally, a cofactor, such as calcium, magnesium, potassium, NAD+/NADH, cGMP, NADP+/NADPH, ATP, ADP, cAMP, and the like. Cofactors can significantly improve the formation of both complexes and proteomes and at the same time the interaction of the proteome and/or the complexes with the potentially interacting compound. As used herein the term "physiological conditions" refers to temperature, pH, ionic strength, viscosity, and similar biochemical parameters which are compatible with a viable organism, and/or which typically exist intracellularly in a viable cultured cell, such as a yeast cell, or a higher eukaryotic cell, such as a mammalian cell.

For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cations (e.g., Mg++, Ca++); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particularly suitable conditions may be readily selected by the skilled practitioner according to conventional methods. For general guidance, the following buffered aqueous solutions may be used: 10-1200 mM NaCl, 5-50 mM Tris/HCl, pH 5-8, with optional addition of divalent cation(s) and/or metal chelators and/or non-ionic detergents and/or membrane fractions and/or anti-foam agents and/or scintillants.

"Essentially physiological conditions" are intended to refer, e.g., to a pH of from 6.5 to 7.5, preferably from 7.0 to 7.5, and/or a buffer concentration of from 10 to 50 mM, preferably from 25 to 50 mM, and/or a concentration of monovalent salts (e.g., Na or K) of from 120 to 170 mM, preferably 150 mM. Divalent salts (e.g., Mg or Ca) may further be present at a concentration of from 1 to 5 mM, preferably 1 to 2 mM, wherein more preferably the buffer is selected from the group consisting of Tris-HCl or HEPES.

The contacting steps according to any of the methods of the invention may, however, also advantageously be performed in the presence of higher salt concentrations (e.g., up to 1.2 M) to reduce non-specific binding of background proteins, or at lower temperature (e.g., 4° C.) to ensure protein stability and prevent protein aggregation.

As mentioned above, the methods of the invention may include a step of eluting the analyte from the solid support with or without a compound bound to it. Preferably, the target to components of the present invention are eluted from the solid support prior to being combined into a sample, based on which the detection step is performed.

Suitable elution methods are principally known in the art and depend on the nature of the interaction. Principally, changes of ionic strength, the pH value, the temperature or incubation with detergents are suitable to dissociate the target component of the analyte from the immobilized compound or the solid support (in case of unspecific interaction). The application of an elution buffer can dissociate binding partners by extremes of pH value (high or low pH; e.g., lowering pH by using 0.1 M citrate, pH 2-3), change of ionic strength (e.g., high salt concentration using NaI, KI, $MgCl_2$, or KCl), polarity reducing agents which disrupt hydrophobic interactions (e.g., dioxane or ethylene glycol), or denaturing agents (chaotropic salts or detergents such as Sodium-docedyl-sulfate (SDS); for a review, see Subramanian A., 2002, Immunoaffinity chromatography. Mol. Biotechnol. 20(1), 41-47).

With these rather non-specific methods most or all bound target components of the analyte will be released and may then be analysed, e.g., by mass spectrometry (or alternatively by any other suitable detection methods, see below).

If the support material is contained within a column the released material can be collected as column flowthrough. In case the support material is mixed with the analyte (so called batch procedure) an additional separation step such as gentle centrifugation may be useful or even necessary and the released material is collected as supernatant. Alternatively, magnetic beads can be used as solid support so that the beads can be eliminated from the sample by using a magnetic device.

The skilled person will appreciate that between the individual steps of the methods of the invention, washing steps may be necessary. Such washing is part of the knowledge of the person skilled in the art. The washing serves to remove non-bound components of the analyte from the solid support. Non-specific (e.g., simple ionic) binding interactions can be minimized by adding low levels of detergent or by moderate adjustments of the salt concentrations in the wash buffer.

Identification and quantification of the eluted target components is based on the spatially resolved signal location and signal magnitude. Many different device technologies that can spatially resolve a signal magnitude or rate of signal appearance can be used for detection of target component binding.

These methods can be employed in any of the methods of this invention, and include, but are not limited to, detection of fluorescence from labelled target components, fluorescent intercalators, fluorescent groove binders, molecular beacons, radioisotopes, surface potentials, coloured products, enzyme labelled targets, antibody labelled targets, and gold particle labelled targets.

Preferably, the eluted target components are preferably detected using radioactivity detection methods, fluorescence detection methods, luminescence detection methods, dye detection methods, enzymatic detection methods and mass spectrometry.

In a preferred embodiment, the eluted target components are detected, i.e., characterized and quantified, by mass spectrometry.

The identification of proteins with mass spectrometric analysis (mass spectrometry) is known in the art (Shevchenko et al., 1996, Analytical Chemistry 68: 850-858; Mann et al., 2001, Analysis of proteins and proteomes by mass spectrometry, Annual Review of Biochemistry 70, 437-473) and is further illustrated in the example section.

The target components in the analyte are advantageously labelled with a detectable label. As mentioned above, in a preferred embodiment of the methods of the invention the detectable label is different in each aliquot of the analyte.

The established SILAC (stable isotope labelling with amino acids in cell culture) procedure for quantitative protein analysis by mass spectrometry may be used in this regard. For example, three populations of cells can be SILAC encoded using three distinct combinations of isotope labelled arginine and lysine ($Arg^0/Lys^0$, $Arg^6/Lys^4$, $Arg^{10}/Lys8$). However, the methods or steps of the present invention can also be combined with any other strategy for protein quantification by mass spectrometry.

Other detectable labels may, however, also be employed in the methods of the invention. For example, suitable detectable labels are selected from the group of radiolabels, such as $^{13}C$, $^{32}P$, $^{35}S$, $^{3}H$, $^{129}I$, $^{99m}Tc$, $^{111}In$, and the like, dye labels, labels that can be detected with antibodies, enzyme labels, and labels having a detectable mass. Examples for the use of mass spectroscopy in proteome analysis are described in Ho Y, et al. (without labels) ("Systematic identification of protein complexes in Saccharomyces cerevisiae by mass spectrometry" Nature 2002, Jan. 10;415(6868):180-3.); Gu S, et al. ("Precise peptide sequencing and protein quantification in the human proteome through in vivo lysine-specific mass tagging". J. Am. Soc. Mass Spectrom. 2003, Jan.; 14(1):1-7) and Williams C and Addona TA ("The integration of SPR biosensors with mass spectrometry: possible applications for proteome analysis." Trends Biotechnol. 2000 Feb.; 18(2):45-8).

The label of the target component may also be selected from phosphorescent markers, fluorescent markers, chemiluminescent markers, phosphatases, avidin, streptavidin, biotin, TAP-method markers, and peroxidases. In addition to TAG, other markers are Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin. The uses of these tags are extensively described in the literature (for example, in Terpe K., Appl. Microbiol. Biotechnol. 2003 Jan.; 60(5):523-33).

As indicated earlier herein, the methods of the invention may be performed in whole or at least in part in a high throughput manner.

The methods of the present invention allow the determination of $K_d$ values for all identified target components in the concentration range covered by different compound concentrations (densities) of the immobilized compound. For targets components with very high affinity, $K_d$ values can be estimated to be lower than those corresponding to the lowest immobilised compound concentration, whereas for rather weakly interacting targets with less than 50% binding at the highest compound concentration, it can be concluded that the $K_d$ values are above a certain threshold. In addition to retrieving quantitative information about target protein sensitivities to the immobilized compound, the background binders can be easily distinguished from specifically retained protein targets.

Figure 2:
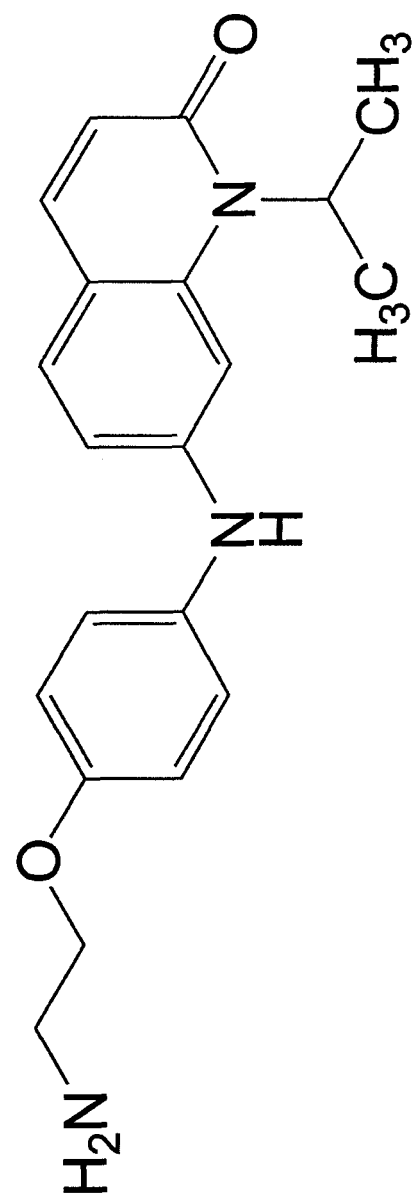
FIG. 2: Specific cellular targets of inhibitor V16742 identified by the quantitative chemical MS approach.
(a) Chemical structure of compound V16742, which was coupled via the primary amino group to epoxy-activated sepharose.
(b) The cellular targets of V16742 identified by quantitative MS are arranged from high to low affinity targets on a scale of Kd value. The representative LTQ-Orbitrap FT-MS scans corresponding to IVA1 and IVA2 settings for one target from each class (high, moderate and low affinity) are shown. The monoisotopic peaks used for quantitation are marked with the differently shaded arrows in accordance with scheme presented in FIG. 1.
(c) Confirmation of results from mass spectrometry analysis. In vitro association of total lysates from HeLa cells with either control matrix or V16742 matrix as per IVA1 (dose-dependent binding) or IVA2 settings (enrichment in second round of IVA) depicted in FIG. 1. The bound proteins eluted from the matrix were immunoblotted with specific antibodies for JNK2 (High affinity target), RIPK2 (Moderate affinity target), ERK2 (Low affinity target), and ROCK2 (Very low affinity target not significantly enriched in IVA2).
(d) Specificity profile of inhibitor V16742. The kinase dendrogram is adapted from Cell Signalling Technology, Inc. TK, nonreceptor tyrosine kinases; RTK, receptor tyrosine kinases; TKL, tyrosine kinase-like kinases; CK, casein kinase family; PKA, protein kinase A family; CAMK, calcium/calmodulin dependent kinases; CDK, cyclin dependent kinases; MAPK, mitogen-activated protein kinases; CLK, CDK-like kinases. The kinase targets of V16742 with high, moderate or low binding affinities are represented by circles of different sizes as indicated in the Figure.

The present invention resolves the major shortcomings of previous chemical proteomic procedures based on immobilized inhibitor affinity purifications. Using HeLa cell extract, the described quantitative chemical analysis of immobilized V16742 resulted in $K_d$ determination for 131 cellular targets including 96 protein kinases identified and quantified by mass spectrometry (FIG. 2b and Table 1). The distribution of identified kinase targets on the kinome tree suggests V16742 to be a rather unselective inhibitor (FIG. 2d). Non-kinase targets can also be identified by the method of the invention. The methods of the invention can be adapted for any type of affinity ligand, which can be immobilized onto a solid support.

Figure 2C:
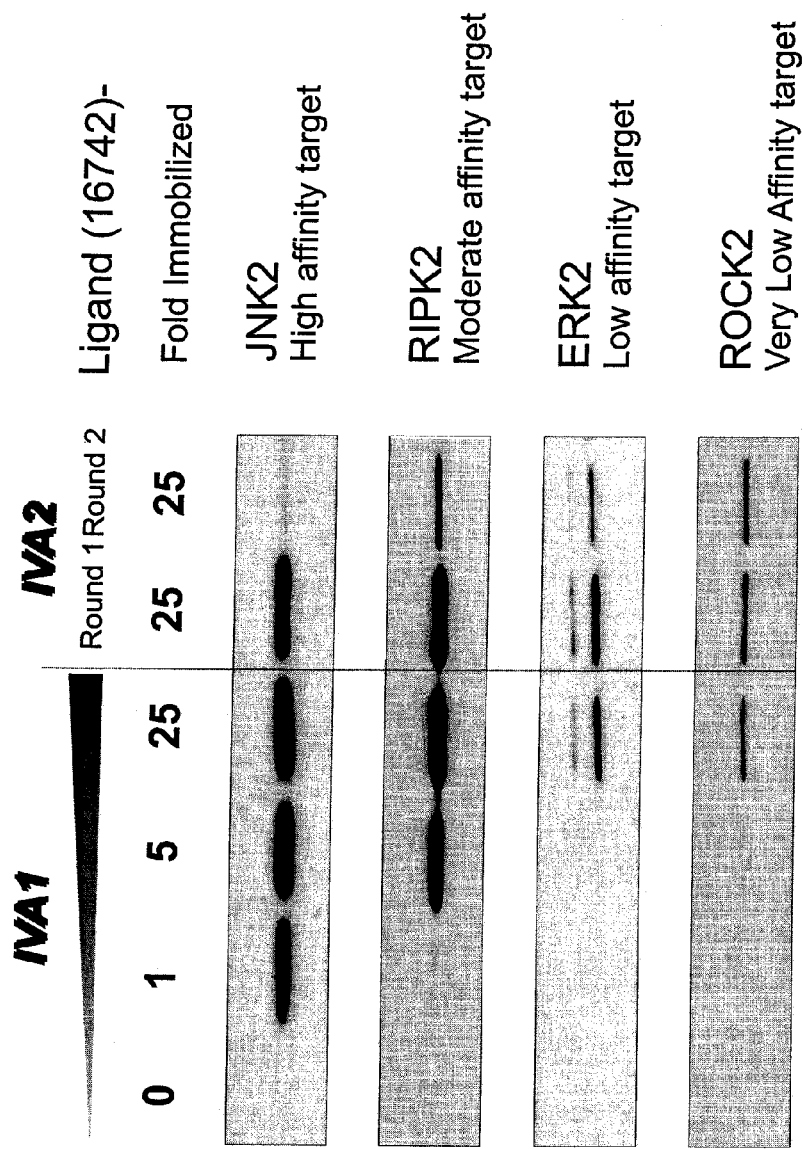

To confirm the mass spectrometry results, total lysates from HeLa cells were subjected to IVA1 and IVA2 with either control beads or V16742 beads. The proteins retained on the beads were immunoblotted with specific antibodies for JNK2, RIPK2, ERK2 and ROCK2, the targets with affinities ranging from high to very low as identified/predicted by mass spectrometry. The kinases specifically interacted with the V16742 matrix (FIG. 2c) with patterns in consent with those predicted by the experimental design (FIG. 1) as well as the quantitative data obtained by the mass spectrometry (Table 1).

Figure 3:
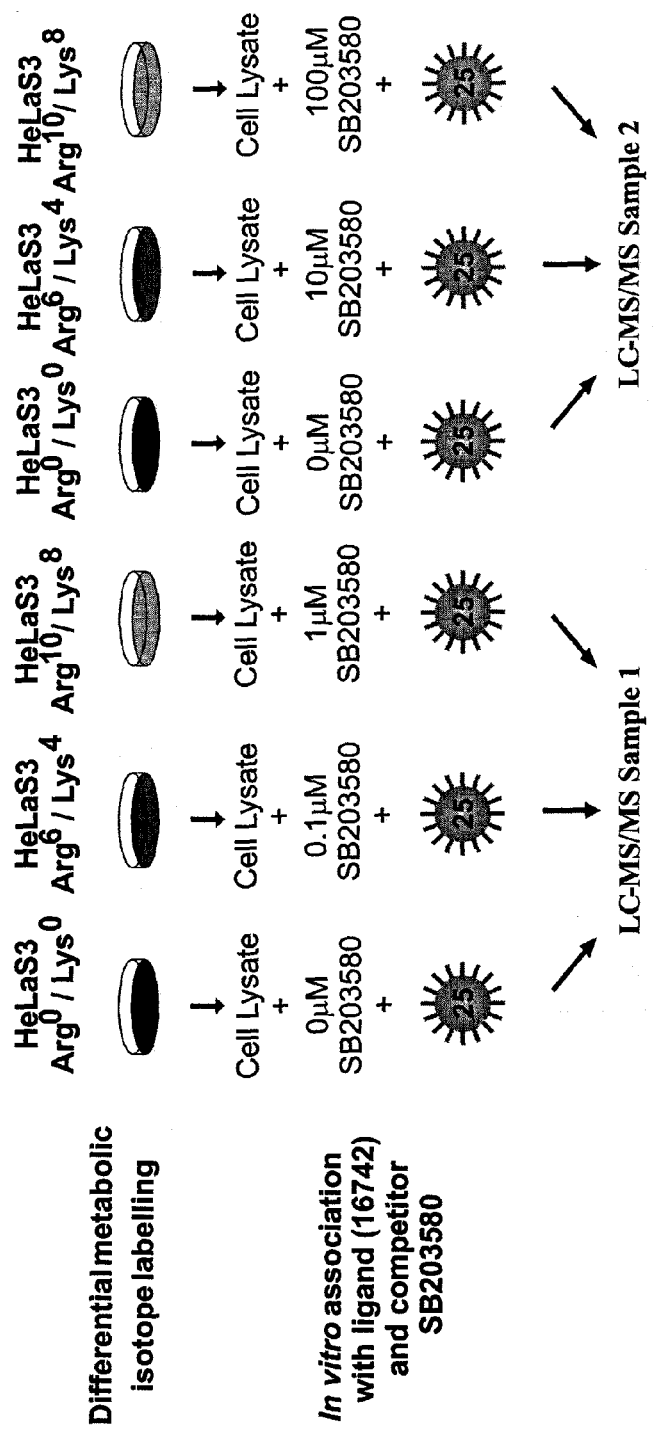
FIG. 3: $IC_{50}$ determination for an inhibitor of interest (SB203580) with respect to competition for binding to an immobilized inhibitor (V16742).
(a) Schematic representation of the competitive binding approach for selectivity analysis: Experimental design for quantitative MS of dose-dependent prevention of binding of SB203580 target to the immobilized small molecule inhibitor V16742.
(b) MS spectra of a representative peptide derived from the topmost SB203580 target protein, RIPK2, are shown which is retained with moderate affinity by V16742 resin.
(c) Immunoblot analysis of competitor selectivity profile. IVA reactions of HeLa cell lysates with immobilised V16742 beads were performed in the presence of increasing SB203580 concentrations. The bound proteins eluted from the matrix were immunoblotted with indicated antibodies against the SB203580 targets to confirm the mass spectrometry results.

The information of the target $K_d$ values for an immobilized inhibitor further allows to set up a quantitative chemical proteomic platform for rapid selectivity analysis of free test compounds against those targets, which are retained by the immobilized inhibitor. To establish this screening approach, increasing concentrations of the kinase inhibitor SB203580 were added to in vitro associations with differentially SLAG-labeled cell lysates and the rather unselective inhibitor V16742 immobilized at the highest density (FIG. 3a). Different concentrations (100 nM, 1 µM, 10 µM, 100 µM) of SB203580 were tested for their ability to compete with the interaction between the entire panel of kinase/non-kinase targets and immobilized V16742.

Figure 3B:
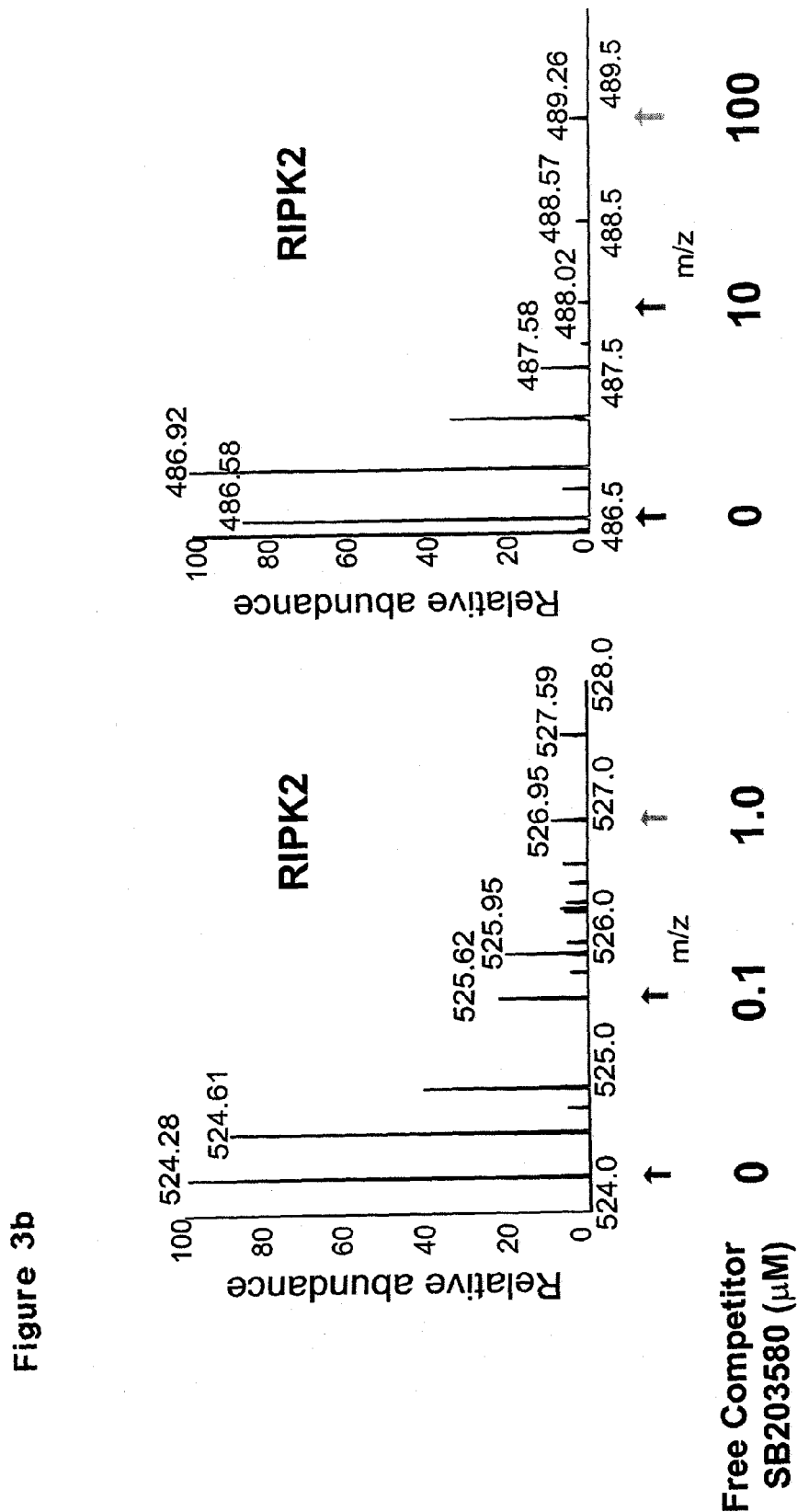

The dose-dependent prevention of binding of SB203580 target proteins to the immobilized inhibitor was measured by quantitative MS and could be used to determine target-specific $IC_{50}$ concentrations for SB203580, at which the free compound inhibited the binding to immobilized V16742 by 50%. The representative spectrums for the RIPK2, the target most strongly competed by SB203580 for its interaction with immobilized V16742, are shown in FIG. 3b. Subsequently, using the classical Cheng-Prusoff equation, the $IC_{50}$ values for SB203580 and the previously determined $K_d$ values for immobilized V16742 could be used to determine the $K_d$ values for SB203580 targets represented on the V16742 affinity resin (Table 2).

Figure 3C:
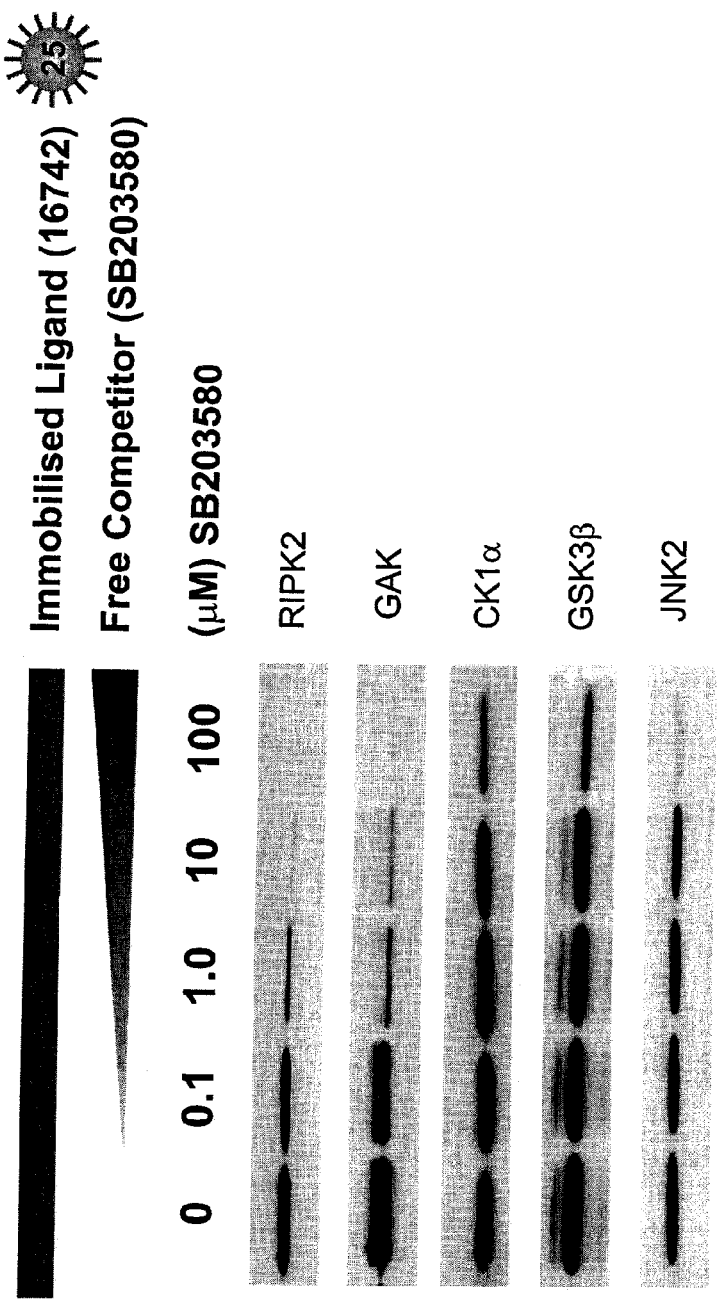

Once again, the mass spectrometry results were confirmed by immunoblotting. IVA reactions in the presence of increasing concentrations of SB203580 were probed with specific antibodies for RIPK2, GAK, CK1α, GSK3β and JNK2 the SB203580 targets identified/predicted by mass spectrometry. The interaction between kinases and immobilized V16742 was specifically competed by SB203580 in a dose dependent manner (FIG. 3c) validating the quantitative mass spectrometry results (Table 2) thereby adding to the proof-of-concept.

Thus, once the $K_d$ values for target protein binding to an unselective (or a combination of unselective) kinase inhibitor(s) have been determined for the proteins in a biological extract by the chemical proteomic strategy described above, this information can be used to set up a selectivity panel, in which all retained proteins can be rapidly tested for their sensitivities to compounds-of-interests (which do not have to be immobilized themselves).

Figure 6A:
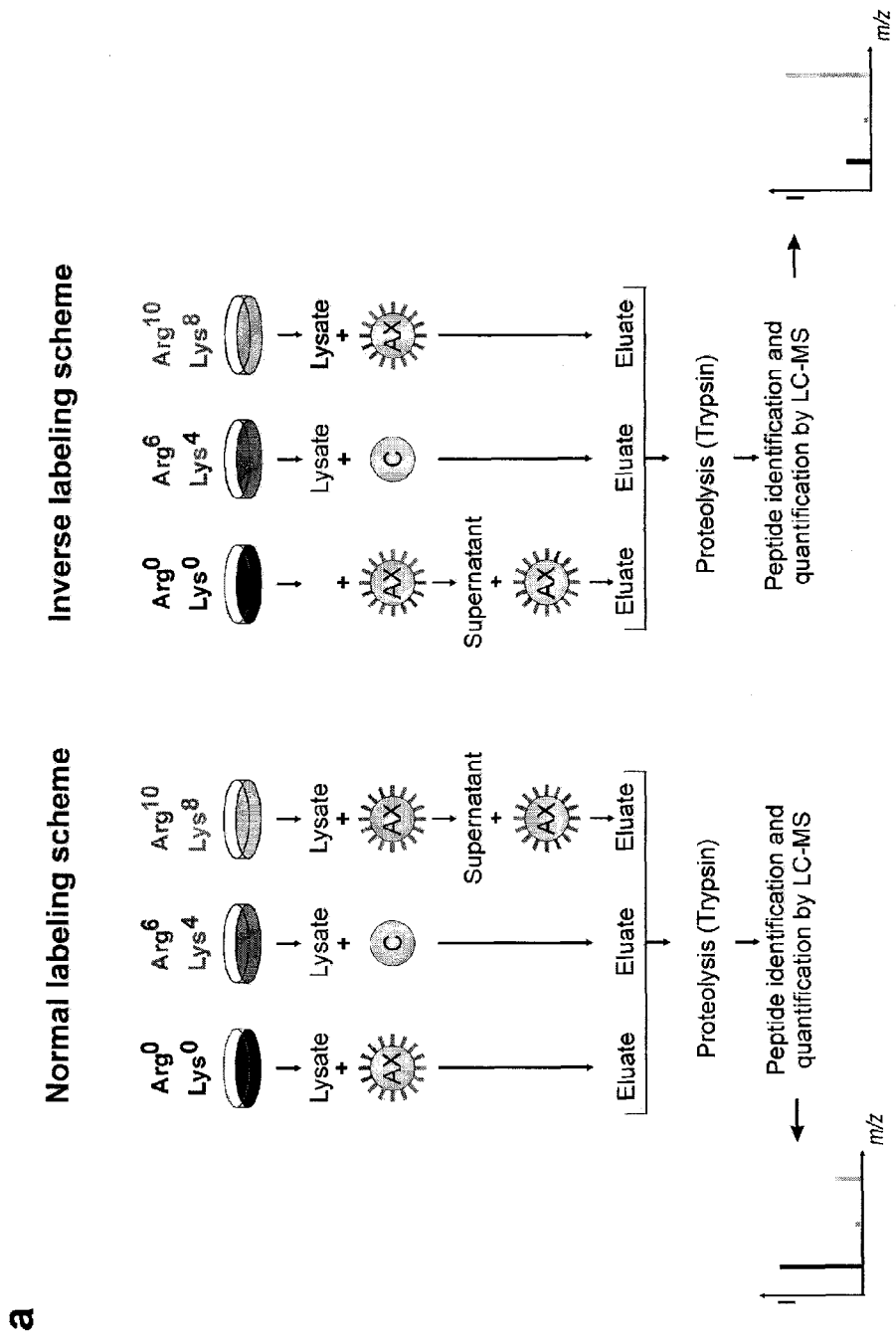

The clinical kinase inhibitor gefitinib and its immobilized derivative AX14596 were employed to further devise the chemical proteomics concept of the present invention that integrates unbiased, proteome-wide target identification and quality-controlled target affinity measurements. Differentially SILAC-encoded cell lysates were either incubated with the inhibitor beads displaying immobilized AX14596 or control resin devoid of ligand. In parallel, the supernatant from the first binding step was subjected to a second incubation with the AX14596 resin (FIG. 4). The resulting three elution fractions were combined, resolved by gel electrophoresis, proteolytically digested and the relative abundance of the retained proteins quantified. Proteins showing considerable binding to the control resin were identified as non-specific interactors and therefore not considered further. The ratio r for the relative amount of protein retained in the second versus the first round of binding to AX14596 beads equals the fraction of a target that was not sequestered by immobilized inhibitor, whereas 1-r indicates the proportion of target that actually bound to the affinity resin (FIG. 4a, FIGS. 6a and 6b). These target-specific ratios were similar in "label switch" experiments (FIGS. 6a and 6c). The binding equilibrium was determined in parallel control SILAC experiments as well as the excess of the immobilized compound over its cellular targets, the excess preferably being a molar excess (FIG. 7 and FIG. 8).

Using the spectrophotometrically determined concentration of the immobilized compound (e.g., AX14596), dissociation constants ($K_i$ values) can be calculated to provide a quantitative measure of the respective target affinities for the immobilized compound (FIG. 4, Tables 3-5).

To check for potentially altered target affinities due to modification and/or immobilization of the parent compound, the effect of increasing compound concentrations on target binding to the modified and/or immobilized compound (for example, the effect of increasing gefitinib concentrations on target binding to AX14596 beads; see FIG. 4) can be monitored, e.g., in competition experiments, preferably in SILAC-based competition experiments. In the example of the experiments depicted in FIG. 4, pre-incubation of lysate with either "free" gefitinib or AX14596 beads prior to addition of the competing reagent gave similar results, showing equilibrium binding under the assay conditions (FIG. 9). The gefitinib concentration required for half maximal inhibition of target binding to AX14596 beads, $IC_{50}$(Gef.), together with the previously determined concentration of its immobilized derivative as well as the target $K_i$ values for its immobilized derivative was used to calculate of the target-specific dissociation constants $K_i$(Gef.) for "free" gefitinib according to the Cheng-Prusoff equation (FIG. 4 and Table 4). These dissociation constants were in good correlation with $K_i$ values determined in in vitro kinase assays using recombinant enzymes (Table 3). These results confirm that the quantitative chemical proteomics strategy of the invention is a suitable method to enable the direct quantitative profiling of compounds, e.g., small molecule kinase inhibitors, against various analysts, e.g., biological extracts.

Moreover, the identification of the NADH diphosphatase NUDT12 and bleomycin hydrolase as potential cellular gefitinib targets indicates that quantification is not restricted to protein kinases (Abdelraheim, S. R., Spiller, D. G. & McLennan, A. G. Mammalian NADH diphosphatases of the Nudix family: cloning and characterization of the human peroxisomal NUDT12 protein. Biochem J 374, 329-335 (2003); Ramotar, D. & Wang, H. Protective mechanisms against the antitumor agent bleomycin: lessons from *Saccharomyces cerevisiae*. Current Genetics 43, 213-224 (2003)).

Figure 5A:
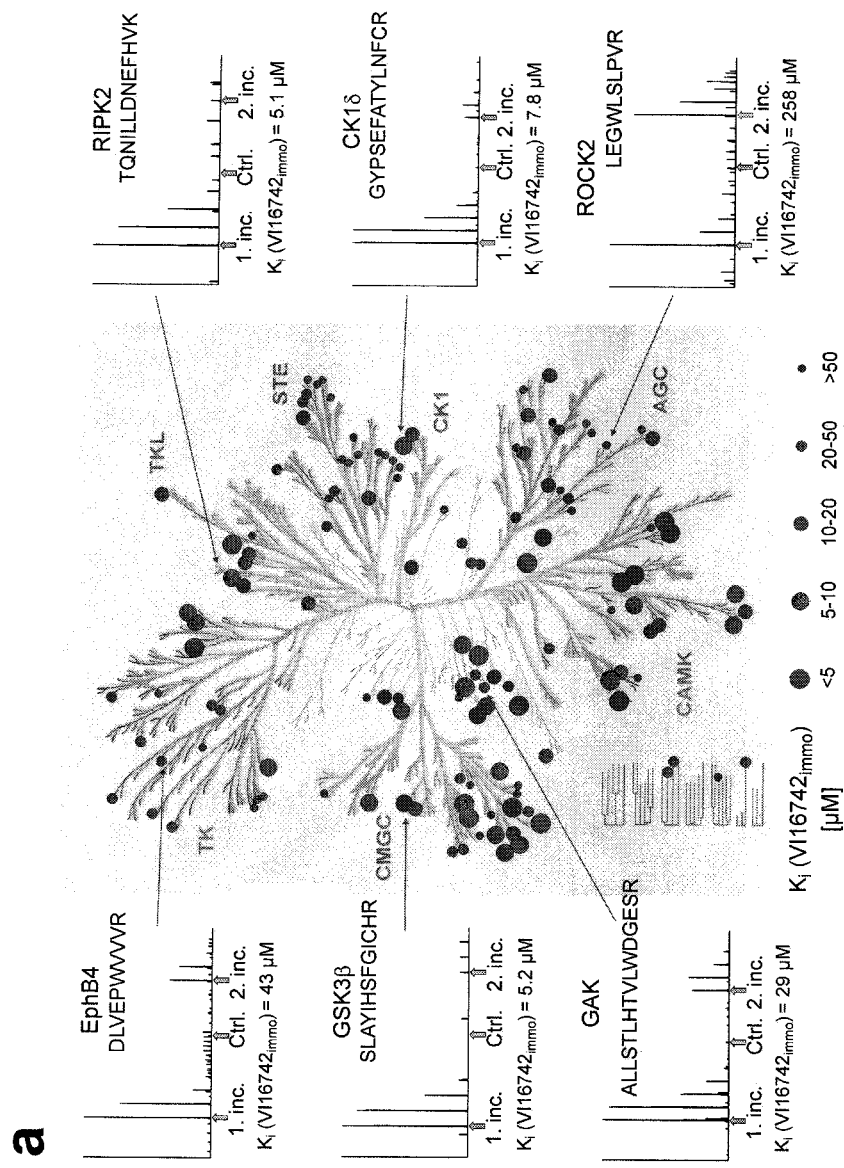

In an alternative implementation of the chemical proteomic approach according to the invention, the broadly-selective pyrido[2,3-d]pyrimidine-based kinase inhibitor VI16742 has been used for affinity capture (FIG. 10a). Using the same quantitative strategy as described above, $K_i$ values for immobilized VI16742 could be determined for about 130 protein kinases and about 25 other nucleotide-binding enzymes (FIG. 5a and Tables 7 to 8). As shown by gene ontology analysis, the corresponding molecular functions were highly over-represented in proteins specifically retained by the inhibitor resin (FIG. 10b).

The VI16742-interacting proteins composed a screening panel for quantitative inhibitor profiling against a large number of nucleotide-binding proteins derived from their native cellular environment. The VI16742 resin with only one immobilized capture molecule allowed for quantitative assessment of an almost similar number of protein kinases in a cellular extract as a previously described resin mixture of seven distinct ligands (Bantscheff, M. et al. *Nat. Biotechnol.* 25, 1035-1044 (2007).

Figure 5B:
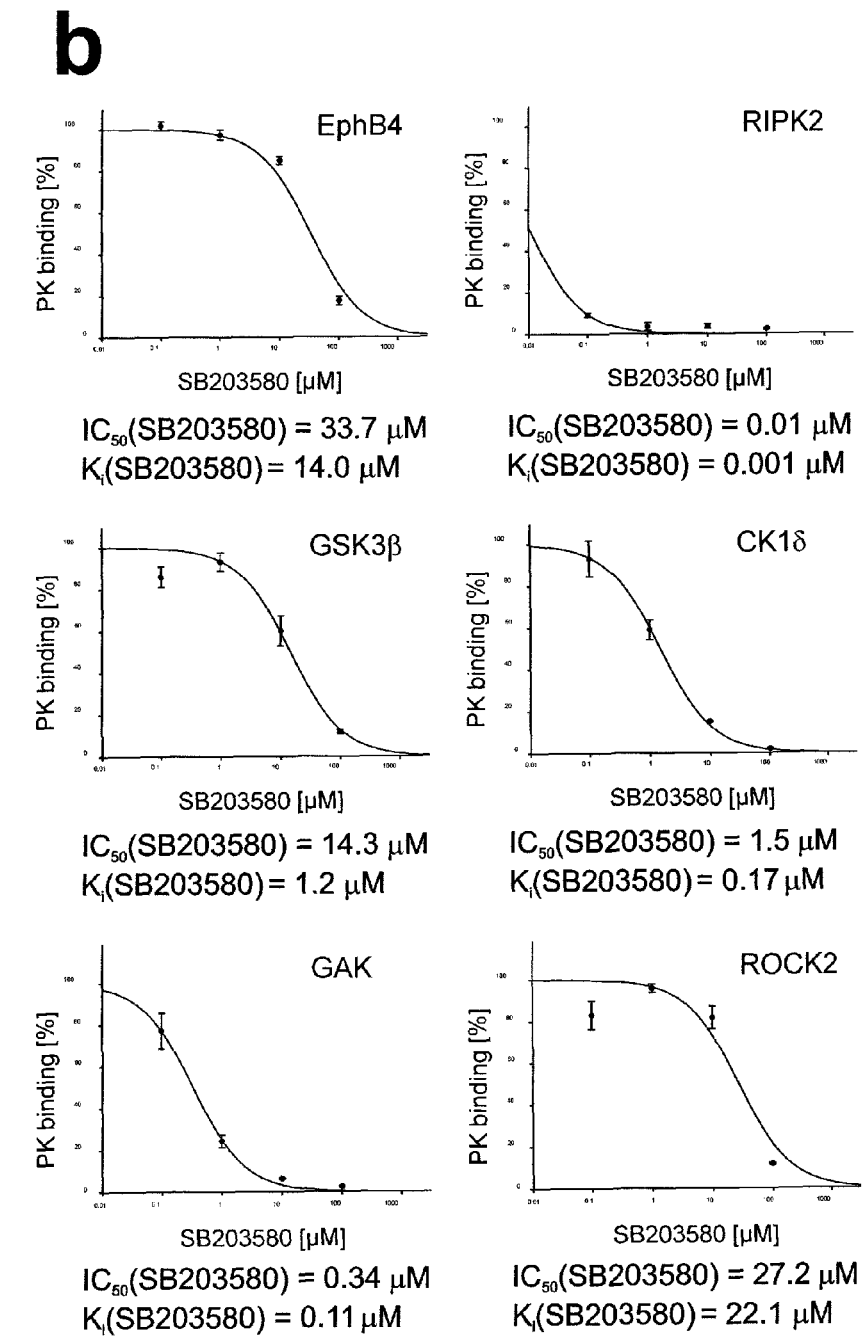

Competition of a compound of interest for target component binding in an analyte, e.g., of the kinase inhibitor SB203580, may be assessed quantitatively by, e.g., SILAC experiments, in a concentration-dependent manner (FIG. 5b). The resulting $IC_{50}$ values in conjunction with the quantitative data for immobilized VI16742 permitted determining dissociation constants for SB203580, as shown for RIPK2, GAK, GSK3β, and others kinase targets (FIG. 5b, Table 8). The $K_i$ values determined for SB203580 and gefitinib by the proteomic approach of the invention corresponded well with data from recombinant kinase assays, indicating a significant improvement on the accuracy of cellular target affinity measurements (Table 6 and FIG. 11).

The method of the invention is, however, not conceptually restricted to kinase inhibitor analysis, but may be applied, e.g, to any other class of small molecules.

Using the chemical proteomics technology according to the methods of the present invention, lead molecules, their molecular targets, mechanisms of action, selectivity and efficacy can be assessed at the same time, thus dramatically improving the drug discovery process and decreasing the attrition rate of compounds in clinical development pipelines.

The use of drug-like compounds immobilized onto a solid support as affinity probes to identify and to quantify the binding of proteins directly from cell lysates or tissue samples offers the advantage of identifying proteins that are inherently druggable. Thus, application of this technology to search for new members of a target family results not only in the identification of new target members, but also in the identification of highly selective high-affinity compounds for that target.

Another aspect of the invention involves the use of the methods disclosed herein as a general drug discovery tool. This chemical proteomics approach facilitates the understanding of functional protein targets and provides tools for dissecting complex cellular processes.

Another aspect of the invention is the use of the methods described and claimed herein for the identification of novel indications for existing, approved drugs. For purposes of illustration consider a drug which is a kinase inhibitor. Given the large number of kinases expected to exist, it is highly likely that this compound inhibits other opportunistic kinase targets involved in pathologies of broader impact. Therefore, it is reasonable to predict that the market potential of this compound could be greatly increased.

Another aspect of the invention is the use use of the methods described and claimed herein in defining the mechanism of action of an early drug candidate. In the scenario where a drug candidate exhibits an interesting biological effect, but for which the general molecular mechanism is unknown, the technology can be used to allow rational optimization of activity. For example, if a company has a small molecule lead or a class of molecules that exhibit an interesting biological effect and efficacy in a given disease model, but the exact mechanism of action is not understood, identification of effect-related targets will serve to facilitate their development into drugs. If structure-activity relationship data is available, regions of the molecule can be identified that can be modified without abolishing biological activity. Immobilizing this drug candidate allows proteomics analysis to identify the target(s) of the compound. Information of this sort is of tremendous value in the optimization process, especially when the target of interest is amenable to structure-based drug design.

Another aspect of the invention is the use of the methods described and claimed herein for ADME/Tox-profiling. The technology disclosed herein can be used to generate toxicity profiles and evaluate the ADME properties of drug candidates before they are introduced into the clinic. The pharmacokinetic properties of a drug candidate can be assessed by exposing the compound or compound class to a battery/panel of ADME/Tox relevant proteomes (i.e., serum binding proteins for use in, for example, assessing bio-availability of a potential drug), which provides important information useful in lead prioritization and lead optimization stages. Given several possible lead classes to take onto lead optimization, a quick assessment of the properties of each class helps the chemist select which class to focus on. The class most likely to have good ADME properties is most likely to generate a drug candidate that has the desired properties for drug development. Equally, knowledge of the secondary and tertiary targets for such compounds will reduce the occurrence of potentially toxic side effects, thus increasing the success rate in clinical development. In general, this technique can be used as a filter to prioritize which compounds to take into more rigorous and expensive pharmacokinetics and toxicology studies.

Thus, the methods for proteome-wide quantification of small molecule binding to cellular target proteins described and claimed herein can be applied to solving fundamental problems and providing services to the pharmaceutical industry.

All publications as cited herein are incorporated herein by reference in their entirety.

The invention is further illustrated by the following figures and examples, which are not to be considered as being limiting for the scope of protection conferred by the claims of the present application.

EXAMPLE 1

Compound Synthesis and Covalent Coupling

The kinase inhibitor V16742 was synthesised on the basis of described synthetic routes (Moloney, G. P. et al. A novel series of 2,5-substituted tryptamine derivatives as vascular 5HT1B/1D receptor antagonists. *J Med Chem* 40, 2347-62 (1997). Barvian, M. et al. Pyrido[2,3-d]pyrimidin-7-one inhibitors of cyclin-dependent kinases. *J Med Chem* 43, 4606-16 (2000)). AX14596 and gefitinib were synthesized as described previously (Brehmer, D. et al. Cellular targets of gefitinib. *Cancer Res* 65, 379-382 (2005)). V16742 was coupled to epoxy-activated Sepharose beads at three different concentrations and the relative concentration of covalently immobilized inhibitor on the distinct resins was determined by spectrophotometry (here 1-, 5- and 25-fold of the lowest concentration). Two volumes of AX14596 at a concentration of 2.5 mM were coupled to one volume of epoxy-activated Sepharose beads (GE Healthcare) as previously described (Wissing, J. et al. Proteomics analysis of protein kinases by target class-selective prefractionation and tandem mass spectrometry. Mol Cell Proteomics 6, 537-547 (2007)). The concentration of covalently immobilized inhibitor was determined spectrophotometrically by measuring the reduction of the inhibitor concentration in the soluble phase during the coupling reaction.

EXAMPLE 2

Cell Culture and In Vitro Association Experiments

For stable isotope labelling with amino acids in cell culture (SILAC), HeLa S3 cells were grown in Dulbecco's modified Eagle's medium (DMEM) containing 10% dialysed fetal bovine serum (Invitrogen) and either unlabelled L-arginine) ($Arg^0$) at 42 mg $I^{-1}$ and L-lysine ($Lys^0$) at 71 mg $I^{-1}$ or equimolar amounts of the isotopic variants L-arginine-U-$^{13}C_6$ ($Arg^6$) and L-lysine-$^2H_4$ ($Lys^4$) or L-arginine-U-$^{13}C_6$—$^{14}N_4$ ($Arg^{10}$) and L-lysine-$^{13}C_6$—$^{15}N_2$ ($Lys^8$) (from Cambridge Isotope Laboratories).

Using the three populations of SILAC-labelled cells and the three different inhibitor resins, two parallel experiments termed as IVA1 (In Vitro Association, Setting 1) and IVA2 (In Vitro Association, Setting 2) were performed. For in vitro association with inhibitor affinity beads, differentially labeled HeLa cells were lysed in buffer containing 50 mM HEPES pH 7.5, 150 mM NaCl, 0.5% Triton X-100, 1 mM EDTA, 1 mM EGTA plus additives. After centrifugation, lysates were adjusted to 1 M NaCl prior to in vitro association of 3 mg of high salt lysate with either 30 µl of drained V16742 matrix or control matrix as per the scheme depicted in FIG. 1 for 2.5 h at 4° C. In IVA1, the resins with inhibitor immobilised at three different concentrations (with final concentrations being 52 µM, 8.74 µM and 1.87 µM in the reaction) were incubated with cell lysates of differentially labelled HeLa cells. In IVA2, SILAC encoded HeLa cells lysates were subjected to two parallel rounds of consecutive affinity purification at the highest ligand density where the supernatant left behind after the first IVA was used for the second round of IVA. An additional incubation of Hela cell lysate with control beads devoid of immobilized inhibitor was also performed to distinguish background binders. After three washing steps with lysis buffer (twice with lysis buffer containing 1M NaCl and once with lysis buffer), the beads were eluted with 30 µl of 1.5×LDS sample buffer at 70° C. for 10 mins to release the resin-bound material.

EXAMPLE 3

IVA Experiments in the Presence of Competitor SB203580

Lysates from differentially SLAG-labeled cells were pre-incubated with increasing concentrations of the kinase inhibitor SB203580 (0 nM, 100 nM, 1 µM, 10 µM, 100 µM) for 30 mins at 4° C. in the dark. These lysates were then subjected to in vitro associations the high density inhibitor (V16742) beads for 2.5 h at 4° C. The samples were then processed as described above.

EXAMPLE 3a

IVA Experiments Using Immobilized Gefitinib (=AX14596) in the Presence of Competitor Gefitinib, or Using Immobilized VI16742 in the Presence of Competitor SB203580

For competition experiments, SILAC-labeled cell lysates were treated with different concentrations of gefitinib (0 nM, 10 nM, 100 nM, 1 µM, 10 µM) or SB203580 (0 nM, 100 nM, 1 µM, 10 µM, 100 µM) for 30 min prior to the addition of AX14596 or VI16742 beads, respectively. Alternatively, lysates were incubated with the inhibitor beads for 30 min prior to addition of the free inhibitors. Subsequently, in vitro associations were performed for a further 2.5 h at 4° C. In all in vitro association experiments, three washing steps (two with lysis buffer containing 1M NaCl and one with lysis buffer) were performed prior to elution of resin-bound material with 30 µl of 1.5×LDS sample buffer at 70° C. for 10 min.

EXAMPLE 3b

IVA Experiments Using Immobilized Dasatinib in the Presence of Competitor Dasatinib The kinase inhibitor dasatinib was coupled to epoxy-activated Sepharose and K562 cells were SILAC-labeled as described in examples 1 and 2. Five dasatinib affinity resins with different concentrations of covalently immobilized inhibitor (here 1-, 2-, 4-, 8- and 16-fold of the lowest concentration) were subjected to IVA experiments as described in examples 2 and 3 in the presence of increasing concentrations of free dasatinib (0 nM, 3 nM, 10 nM, 30 nM, 100 nM, 1 µM, 10 µM). The mass spectrometric analysis was performed as described in examples 4, 6, 7 and 8. $IC_{50}$ values for the free dasatinib ($CC_{50}$) and the $K_d$ values for the immobilized dasatinib were used to determine $K_d$ values for the free dasatinib as described in example 9.

EXAMPLE 4

Sample Preparation for Mass Spectrometry

The affinity chromatography eluates were combined and resolved by electrophoresis on ready-made gels (NuPage 4-12% Bis-Tris, Invitrogen) and visualized by colloidal Coomassie staining (Shevchenko, A., et al., Nat. Protoc. 1, 2856-60 (2006)). The gels were then cut into 3 slices, followed by in-gel digestion with trypsin and peptide extraction with StageTips (Rappsilber, J. et al., Nat. Protoc. 2, 1896-906 (2007); Olsen, J. V. et al., Cell 127, 635-48 (2006)).

EXAMPLE 5

Immunoblot Analysis

Immunoblotting of affinity chromatography eluates from either IVA1 or IVA2 setting was performed with the following antibodies: Rabbit anti-casein kinase Iα, Rabbit anti-JNK2, Rabbit anti-ROCK-II (all from Cell Signaling Technology, Inc.), anti-GSK3β, anti-RIPK2, anti-GAK, anti-ERK2 (Santa Cruz)

IVA reactions of HeLa cell lysates with immobilised V16742 beads were performed in the presence of increasing SB203580 concentrations (0 nM, 100 nM, 1 µM, 10 µM, 100 µM). To validate the mass spectrometry results, the bound proteins eluted from the matrix were immunoblotted with specific antibodies against the SB203580 targets namely JNK2, RIPK2, to ERK2 and ROCK2.

EXAMPLE 6

Mass Spectrometric Analysis

All mass spectrometric (MS) analyses were performed with a nanoflow HPLC system (Agilent Technologies 1100, Waldbronn, Germany) connected to a hybrid LTQ-Orbitrap (Thermo Fisher Scientific, Bremen, Germany) mass spectrometer equipped with a nanoelectrospray ion source (Proxeon Biosystems, Odense, Denmark) essentially as described (Olsen, J. V. et al., Cell 127, 635-48 (2006)). Briefly, the tryptic peptide and phosphopeptide mixtures were separated in a 15 cm analytical column (75 µm inner diameter) in-house packed with 3 µm C18 beads (Reprosil-AQ Pur, Dr. Maisch) with a 2 hr gradient from 5% to 40% acetonitrile in 0.5% acetic acid. The effluent from the HPLC was directly electrosprayed into the mass spectrometer. The MS instrument was operated in data-dependent mode to automatically switch between full scan MS and MS/MS acquisition. Survey full scan MS spectra (from m/z 300-2000) were acquired in the orbitrap with resolution R=60,000 at m/z 400 (after accumulation to a 'target value' of 1,000,000 in the linear ion trap). The five most intense peptide ions with charge states ≥2 were sequentially isolated to a target value of 5,000 and fragmented in the linear ion trap by multi-stage activation (MSA or pseudo $MS^3$) (Olsen, J. V. et al., Cell 127, 635-48 (2006); Schroeder, M. J. et al., Anal. Chem. 76, 3590-8 (2004)). All fragment ion spectra were recorded in the LTQ part of the instrument. For all measurements with the orbitrap detector, a lock-mass ion from ambient air (m/z 429.08875) was used for internal calibration as described (Olsen, J. V. et al., Mol. Cell. Proteomics 4, 2010-21 (2005)). Typical mass spectrometric conditions were: spray voltage, 2.4 kV; no sheath and auxiliary gas flow; heated capillary temperature, 150° C.; normalised collision energy 35% for MSA in LTQ. The ion selection threshold was 500 counts for $MS^2$. An activation q=0.25 and activation time of 30 ms were used.

EXAMPLE 7

Peptide Identification and Quantitation

MS/MS peak lists were extracted from the raw MS files and searched by MASCOT against a concatenated target/decoy database (Elias et al., Nat. Methods 2, 667-75 (2005)) consisting of a combined forward and reversed version of the IPI human database v. 3.19. The initial mass tolerance in MS mode was set to 25 ppm and MS/MS mass tolerance was 0.5 Da. Cysteine carbamidomethylation was searched as a fixed modification, whereas N-acetyl protein, N-pyroglutamine, oxidized methionine, phosphorylation of serine, threonine and tyrosine and SILAC labels on arginine and lysine were searched as variable modification. The resulting MASCOT html-output file was linked to the raw MS files and loaded into the MSQuant software (http://msquant.sourceforge.net). To minimize the false-discovery rate (FDR), all peptide identifications were filtered by thresholds on mass error and MASCOT score. We accepted peptides based on the criteria that the number of forward hits in the database were at least 200-fold higher than the number of reversed database hits (incorrect peptide sequences), which gives an estimated FDR of less than 1% (p<0.01) (Elias et al., Nat. Methods 2, 667-75 (2005)). The final filtering criteria at which p<0.01 was mass error <5 ppm (all experiments), MASCOT score ≥16 (IVA 1 and IVA2; experiment 1) MASCOT score ≥18 (IVA1, experiment 2), MASCOT score ≥17 (IVA1, experiment 2) or MASCOT score ≥12 (Competition experiment 1 and 2). MSQuant calculated the ratio average over the peptide elution time and the assignments used for quantitation were visually displayed and validated. In particular, validation criteria included that the peptide should be identified in the correct SILAC form (heavy, middle or light) and contain the correct number of lysine and arginine residues specified by the mass difference observed in the full scan between the SILAC partners.

EXAMPLE 8

Data Analysis

A common IPI identifier template was assigned to peptides based on the MASCOT html-output file for the IVA2 setting in first experiment. The proteins hits identified based on unique peptides were filtered for mass error and MASCOT score. Eventually, the hits identified in both first and second IVA2 experiments were quantified for IVA2 setting of first experiment by MSQuant. We then filtered out background binders which showed more than 25% binding to the control beads in comparison with the binding observed at high density ligand beads. A next round of sorting was done to filter out protein hits that are less than 50% enriched in the IVA second round compared to IVA first round. This is because at enrichment below 50%, there could be significant errors in deducing kd values for the corresponding targets. For the targets that were specifically enriched in IVA2 of experiment one, the ratios depicting binding of target proteins at varying ligand (V16742) concentrations (IVA1 setting) were then obtained by MSQuant. The same set of targets was also quantified in IVA2 and IVA1 settings of an independent second experiment.

For the competition experiments with SB203580, the data analysis was essentially similar as for the IVA experiments and ratios obtained through MSQuant were represented according to the common IPI identifier template. We then selected target proteins which showed atleast 50% lesser binding at the highest competitor concentration of 100 µM compared to the control IVA reaction with high density ligand beads in the absence of SB203580. For these selected targets, the ratios depicting competition at 1 µM and 0.1 µM SB203580 were also obtained by MSQuant.

Raw data files resulting from all experiments with the inhibitor resin, e.g., AX14596, were collectively analyzed with the MaxQuant software (version 1.0.12.0), which performs peak list generation, SILAC-based quantitation, false discovery rate (FDR) determination, peptide to protein group assembly and data filtration as described (Graumann, J. et al. SILAC-labeling and proteome quantitation of mouse embryonic stem cells to a depth of 5111 proteins. Mol Cell Proteomics (2007); Cox, J. & Mann, M. Is proteomics the new genomics? Cell 130, 395-398 (2007)). Data were searched against a concatenated forward and reversed version of the human IPI database (version 3.37) supplemented with frequently detected contaminants using Mascot (Matrix Science, version 2.1.04). Cysteine carbamidomethylation was set as a fixed modification and N-acetyl protein and oxidized methionine were allowed as variable modifications. Spectra that were determined to result from heavy labeled peptides in the pre-search detection of SILAC partners by MaxQuant were searched with the fixed modifications $Lys^4$, $Lys^8$, $Arg^6$ and $Arg^{10}$, whereas MS/MS spectra for which no SILAC state could be assigned before database searching were searched with $Lys^4$, $Lys^8$, $Arg^6$ and $Arg^{10}$ as variable modifications. The mass tolerance was set to 5 ppm for monoisotopic precursor ions and to 0.5 Da for MS/MS peaks. The minimum peptide length was set to 6 amino acids and up to three missed cleavages and three isotopically labeled amino acids were permitted per peptide. The accepted false discovery rate (FDR) was 1% for the proteins and peptides. The cut-off for the posterior error probability (PEP) of peptides was set to 10%. Peptide PEPs were determined by generating Mascot score and peptide-length-dependent histograms for both the forward and the reverse hits and then deriving the probability of a false identification for a given top-scoring peptide using Bayes' theorem. The PEPs of peptides belonging to the same proteins were then multiplied. Each peptide sequence was considered only once with the lowest PEP determined in case of multiple sequencing of the same isotopic pattern or of peptide species with different SILAC, charge or modification states. Proteins were then sorted according to their products of their peptide PEPs and included until a FDR of 1% was reached according to the fraction of reverse proteins contained in the protein list. In addition to the FDR threshold applied for protein identification, proteins were only included when they were identified with at least two peptides (of which one was required to be unique for the protein) and quantified if at least on quantifiable SILAC pair was associated with them. Outliers were not removed as protein ratios were calculated as the median instead of the average of all peptide ratios. For peptides shared among different identified proteins, SILAC ratios were only considered for the ratio of the protein identified with the highest number of unique peptides. Protein ratios for the different in vitro association experiments were corrected for the initial SILAC pooling ratio, which was determined from the median of protein ratios in pooled SILAC-encoded cell extracts.

Quantified proteins were first sorted according to the averaged ratio of protein bound to control beads without inhibitor versus protein bound to inhibitor beads. Only proteins with a background ratio of less than 0.2 were considered further. Subsequently, proteins for which the ratios of binding in the second versus the first round of incubation with inhibitor beads were available as duplicates were taken with their averaged values for further data evaluation (in case this averaged value was less than one). Likely contaminants exhibiting an inverted ratio in the replicate experiments were excluded from further analysis. The ratio r of target protein binding in the second versus the first round of in vitro association was used to calculate the respective dissociation constants $K_i$ (Inhibitor$_{immo}$) for the immobilized inhibitor according to the equation:

$$K_i(\text{Inhibitor}_{immo}) = [\text{Inhibitor}_{immo}] \times r/(1-r)$$

[Inhibitor$_{immo}$] was the concentration of immobilized inhibitor in the final volume of the binding assay. Moreover, ratios of resin bound targets after 5 h versus 2.5 h and for binding from 1 mg compared to 3 mg of starting extracts were determined to evaluate to which extent equilibrium binding conditions were satisfied in the in vitro association experiments. In parallel, the pooling error-corrected ratios from the competition experiments using an inhibitor resin, e.g., AX14596, and different free inhibitor concentrations, e.g., gefitinib concentrations, were used to determine IC$_{50}$ values for half maximal inhibition of binding for targets, for which $K_d$ values for immobilized ligand was available. The corresponding ratios from duplicate experiments were averaged.

Using the equation for one site saturation with maximum binding in the absence of inhibitor set to 100%, target-specific IC$_{50}$ values were determined with the ligand binding module of SigmaPlot (version 10.0, Systat software, Inc.). Only target proteins were considered with ratios of 0.6 or less at the highest concentration of free inhibitor compared to the control incubation. Subsequently, target $K_i$ values for free inhibitors were calculated according to the Cheng-Prusoff equation:

$$K_i(\text{Inhibitor}_{free}) = K_i(\text{Inhibitor}_{immo})/([\text{Inhibitor}_{immo}]+K_i(\text{Inhibitor}_{immo})) \times IC_{50}(\text{Inhibitor}_{free})$$

EXAMPLE 9

Determination of Binding Constants

The ratios obtained from IVA1 and IVA2 experiments were converted to percent binding at different ligand densities. $K_d$ values were determined by using SIGMA PLOT software, Ligand Binding module using equation for one site saturation with maximum binding set to 100%. $K_d$ value for individual targets calculated from two independent experiments generally were within twofold.

The dose-dependent prevention of binding of SB203580 target proteins to the immobilized inhibitor measured by quantitative MS could be represented as dose-response curves. The data was fitted to one-site competition equation using SIGMAPlot to determine target-specific IC$_{50}$ for SB203580. Subsequently, the IC$_{50}$ values for SB203580 and the previously determined $K_d$ values for immobilized V16743 could be used to determine the $K_d$ values for SB203580 targets represented on the V16742 affinity resin, according to the formula:

$$K_{d(SB203580)} = (K_{d(V16742)}/(K_{d(V16742)} + [V16742]) \times IC_{50(SB203580)}$$

EXAMPLE 10

Kinase Assays

In vitro kinase assays of receptor-interacting protein kinase 2 (RIPK2), c-jun NH$_2$ terminal kinase 2α2 (JNK2α2), casein kinase 1δ (CK1δ), Ephrin receptor B4 (EphB4) (all from Upstate), casein kinase 1ε (CK1ε) (Invitrogen), glycogen synthase kinase 3β (GSK3β), breast tumor kinase (BRK), the Src family kinases Lyn and Yes, hepatocyte growth factor receptor (Met), (all from ProQinase) and cyclin G-associated kinase (GAK) (Godl, K. et al. An efficient proteomics method to identify the cellular targets of protein kinase inhibitors. *Proc Natl Acad SCi USA* 100, 15434-15439 (2003)) were performed in kinase buffer containing 60 mM HEPES-NaOH, pH 7.5, 3 mM MgCl$_2$, 3 mM MnCl$_2$, 3 μM sodium orthovanadate and 1.2 mM dithiothreitol. As substrates served 0.33 mg/ml myelin basic protein (Sigma Aldrich) for RIPK2 and BRK, 200 μmol/l CK1tide (Upstate) for CK1δ and CK1ε, 0.2 mg/ml histone mix (Roche) for GAK, 0.2 mg/ml poly (Glu$_4$Tyr) (Sigma) for EphB4, Lyn, Yes and Met, 80 μg/ml GST-c-jun (Hibi, M., Lin, A., Smeal, T., Minden, A. & Karin, M. Identification of an oncoprotein- and UV-responsive protein kinase that binds and potentiates the c-Jun activation domain. *Genes Dev* 7, 2135-2148 (1993)) for JNK2α2 and 50 μM GSK3β substrate (Calbiochem) for GSK3β. All kinases were assayed in a total volume of 25 μl in the presence of 0.1 μM ATP, 0.5 μCi [γ-$^{33}$P]ATP and different SB203580 or gefitinib concentrations. Upon a 30 min pre-incubation step on ice the kinase reactions were started by the addition of ATP and performed for 7 min at 30° C. Kinase reactions were linear over the incubation time. In case of GAK and RIPK2, the reaction was stopped by the addition of 3×SDS sample buffer. After gel electrophoresis, phosphorylated substrate proteins were quantified by phosphoimaging. For all other kinases the reactions were terminated by addition of 6 μl 3% phosphoric acid and phosphorylated substrates were bound to P30 glass fibre filters (Wallac, Turku, Finland) to measure $^{33}$P incorporation. For EGFR in vitro kinase assays, HeLa S3 cells were grown to confluence on 15-cm dishes in DMEM containing 10% fetal bovine serum (Invitrogen). Lysates were prepared with 750 μl lysis buffer and pre-cleared by centrifugation (Blencke, S., Ullrich, A. & Daub, H. Mutation of threonine 766 in the epidermal growth factor receptor reveals a hotspot for resistance formation against selective tyrosine kinase inhibitors. *J Biol Chem* 278, 15435-15440 (2003)). Aliquots of 350 µl of lysate were immunoprecipitated with mAb108.1 antibody and protein G-Sepharose beads for 3 h at 4° C. (Blencke, S., Ullrich, A. & Daub, H. Mutation of threonine 766 in the epidermal growth factor receptor reveals a hotspot for resistance formation against selective tyrosine kinase inhibitors. *J Biol Chem* 278, 15435-15440 (2003)). Beads were washed twice with 300 ml of lysis buffer without additives and twice with 200 µl of kinase buffer. Precipitated EGFRs were then pre-incubated on ice for 30 min in kinase buffer supplemented with 0.2 mg/ml poly (Glu$_4$Tyr) and different gefitinib concentrations. Kinase reactions were started by the addition of 0.1 µM ATP and 1 µCi [γ-$^{33}$P]ATP and performed for 10 min at 30° C. in a total volume of 50 µl prior to the addition of 12 µl 3% phosphoric acid and measuring $^{33}$P incorporation into filter-bound substrate. For all kinases, the IC$_{50}$ values were then determined using SigmaPlot (version 10.0, Systat software, Inc.). IC$_{50}$≅K$_i$ for the analyzed kinases, as the ATP concentration used in all assays (0.1 µM) was considerably lower than the K$_M$ values for ATP (Knight, Z. A. & Shokat, K. M. Features of selective kinase inhibitors. *Chem Biol* 12, 621-637 (2005)).

Those of ordinary skill in the art will appreciate that methods, procedures, devices, instrumentation, materials, and reagents other than those specifically described herein can readily be employed in the practice of this invention as broadly described herein without undue experimentation. All methods, procedures, devices, instrumentation, materials, and reagents that can be readily adapted to the practice of this invention or that are recognized in the art to be functional equivalents of the specific methods, procedures, devices, instrumentation, materials, and reagents disclosed herein are intended to be encompassed by this invention. All references cited herein are incorporated by reference herein to the extent that they are not inconsistent with the description herein.

TABLE 1

| | Kinase | | | EXPERIMENT 1 | | | | | EXPERIMENT 2 | | | | |
|---|---|---|---|---|---|---|---|---|---|---|---|---|---|
| | | | | Percent bound at various 16742 conc | | | | | Percent bound at various 16742 conc | | | | |
| Accession No. | Name | Description | | 52 μM | 8.74 μM | 1.87 μM | Kd (μM) | R2 | 52 μM | 8.74 μM | 1.87 μM | Kd (μM) | R2 | Kd Avg (μM) | Avg Dev |
| IP00298940.3 | AurA | Serine/threonine protein | | 95.30 | 105.34 | 82.56 | 0.33 | 0.60 | 95.21 | 87.69 | 85.71 | 0.38 | 0.00 | 0.36 | 0.02 |
| IP00219129.8 | | Ribosyldihydronicotinamide dehydrogenase | | 96.92 | 108.34 | 80.25 | 0.37 | 0.57 | 98.51 | 89.23 | 72.33 | 0.75 | 0.97 | 0.56 | 0.19 |
| IP00479760.3 | AAK1 | AP2 associated kinase 1 | | 87.47 | 86.28 | 70.74 | 0.87 | 0.16 | 91.12 | 78.23 | 71.67 | 0.95 | 0.00 | 0.91 | 0.04 |
| IP00397883.5 | | cDNA FLJ45252 fis, clone BRHIP2011199 | | 89.78 | 91.84 | 72.25 | 0.74 | 0.66 | 94.35 | 74.89 | 68.93 | 1.11 | 0.31 | 0.93 | 0.18 |
| IP00410344.2 | PLK4 | Serine/threonine protein kinase PLK4 | | 95.46 | NA | NA | NA | NA | 97.42 | 82.19 | 67.92 | 1.01 | 0.85 | 1.01 | 0.00 |
| IP00220305.1 | JNK1 | Isoform 3 of Mitogen activated protein kinase 8 | | 93.86 | 90.77 | 64.94 | 1.01 | 0.96 | 96.58 | 80.37 | 66.69 | 1.10 | 0.81 | 1.05 | 0.05 |
| IP00176642.3 | AurB | Serine/threonine protein kinase 12 | | 92.00 | 102.64 | 63.29 | 0.90 | 0.76 | 92.69 | 73.95 | 62.51 | 1.46 | 0.57 | 1.18 | 0.28 |
| IP00024673.2 | JNK2 | Isoform Alpha 2 of Mitogen activated protein kinase 9 | | 92.48 | 89.45 | 68.10 | 0.91 | 0.90 | 96.58 | 75.70 | 57.18 | 1.69 | 0.87 | 1.30 | 0.39 |
| IP00185037.8 | MARK1 | Isoform 1 of Serine/threonine protein kinase MARK1 | | 89.79 | 84.22 | 59.43 | 1.38 | 0.87 | 94.94 | 71.99 | 48.24 | 2.47 | 0.89 | 1.92 | 0.55 |
| IP00021331.1 | NEK2 | Isoform 1 of Serine/threonine protein kinase Nek2 | | 94.43 | NA | NA | NA | NA | 89.99 | 79.19 | 46.48 | 2.17 | 1.00 | 2.17 | 0.00 |
| IP00031681.1 | CDK2 | Cell division protein kinase 2 | | 94.46 | 87.48 | 54.27 | 1.52 | 0.99 | 98.42 | 64.96 | 40.79 | 3.45 | 0.95 | 2.48 | 0.96 |
| IP00337426.1 | BIKE | Isoform 1 of BMP 2 inducible protein kinase | | 86.15 | 85.21 | 57.66 | 1.46 | 0.76 | 95.27 | 61.22 | 46.08 | 3.59 | 0.47 | 2.52 | 1.07 |
| IP00015538.1 | PKD3 | Serine/threonine protein kinase D3 | | 92.65 | 96.15 | 34.10 | 2.30 | 0.83 | 82.50 | 78.27 | 36.09 | 2.92 | 0.99 | 2.61 | 0.31 |
| IP00301609.7 | NEK9 | Serine/threonine protein kinase Nek9 | | 95.39 | 83.95 | 39.97 | 2.41 | 0.97 | 96.03 | 79.67 | 34.98 | 2.91 | 0.98 | 2.66 | 0.25 |
| IP00329638.10 | ZAK | Isoform 1 of Mitogen activated protein kinase kinase kinase MLT | | 91.29 | 77.35 | 40.19 | 1.87 | 0.99 | 96.87 | 56.65 | 31.49 | 3.46 | 0.97 | 2.66 | 0.80 |
| IP00022865.1 | | Cyclin A2 | | 86.28 | 74.29 | 47.24 | 2.47 | 0.86 | 90.60 | 75.23 | 38.59 | 3.00 | 0.99 | 2.74 | 0.27 |
| IP00013004.1 | | Isoform 1 of Pyridoxal kinase | | 97.55 | 100.79 | 26.65 | 2.47 | 0.77 | 98.95 | 82.18 | 22.00 | 3.62 | 0.91 | 3.05 | 0.57 |
| IP00009334.4 | PKD2 | Serine/threonine protein kinase D2 | | 93.01 | 78.49 | 29.28 | 3.45 | 0.96 | 94.51 | 74.72 | 33.37 | 3.37 | 0.99 | 3.41 | 0.04 |
| IP00552413.2 | CDK9 | Isoform 2 of Cell division protein kinase 9 | | 87.51 | 86.50 | 38.10 | 2.50 | 0.90 | 86.23 | 67.51 | 28.73 | 4.60 | 0.98 | 3.55 | 1.05 |
| IP00306833.3 | MPSK1 | Serine/threonine kinase 16 | | 88.71 | 63.64 | 33.09 | 4.50 | 0.98 | 89.83 | 72.09 | 44.62 | 2.74 | 0.94 | 3.62 | 0.88 |
| IP00023530.6 | CDK5 | Cell division protein kinase 5 | | 81.61 | 66.45 | 42.58 | 3.48 | 0.70 | 94.33 | 66.43 | 33.94 | 3.97 | 0.99 | 3.73 | 0.24 |
| IP00549858.4 | PCTAIRE1 | Serine/threonine protein kinase PCTAIRE 1 | | 91.54 | 71.62 | 40.93 | 3.03 | 0.98 | 90.21 | 61.21 | 29.75 | 5.07 | 0.99 | 4.05 | 1.02 |
| IP00028071.3 | CLK2 | Isoform Long of Dual specificity protein kinase CLK2 | | 89.80 | 73.32 | 28.46 | 3.97 | 0.98 | 90.76 | 70.46 | 19.77 | 4.97 | 0.96 | 4.47 | 0.50 |
| IP00552691.1 | TNK1 | Isoform 2 of Non receptor tyrosine protein kinase TNK1 | | 90.97 | 80.33 | 27.25 | 3.52 | 0.94 | 94.15 | 62.99 | 21.96 | 5.47 | 0.99 | 4.49 | 0.98 |
| IP00291427.2 | | Isoform 1 of CDK5 and ABL1 enzyme substrate 1 | | 61.80 | NA | NA | NA | NA | 87.10 | 61.27 | 33.74 | 4.77 | 0.96 | 4.77 | 0.00 |
| IP00030247.1 | | Cyclin T1 | | 90.32 | 74.71 | 32.05 | 3.55 | 0.98 | 86.27 | 56.68 | 24.77 | 6.50 | 0.99 | 5.03 | 1.47 |
| IP00411818.3 | ULK3 | Hypothetical protein DKFZp434C131 | | 91.49 | 82.41 | 35.25 | 2.83 | 0.96 | 95.06 | 53.01 | 17.99 | 7.27 | 0.98 | 5.05 | 2.22 |
| IP00149341.1 | DRAK2 | Serine/threonine protein kinase 17B | | 95.52 | 65.33 | 27.46 | 4.63 | 0.99 | 91.85 | 64.37 | 18.72 | 5.72 | 0.98 | 5.18 | 0.55 |
| IP00172450.2 | CaMK2g | Isoform 4 of Calcium/calmodulin dependent protein kinase type II gamma chain | | 95.61 | 95.81 | 23.89 | 2.70 | 0.81 | 94.97 | 49.34 | 12.60 | 8.07 | 0.97 | 5.38 | 2.68 |
| IP00027983.1 | | Cylidine deaminase | | 98.60 | 80.09 | 8.93 | 4.71 | 0.85 | 95.56 | 68.24 | 6.93 | 6.17 | 0.90 | 5.44 | 0.73 |
| IP00165249.2 | PFTAIRE1 | Isoform 1 of Serine/threonine protein kinase PFTAIRE 1 | | 92.38 | 64.40 | 28.79 | 4.71 | 1.00 | 92.66 | 54.91 | 22.42 | 6.64 | 0.99 | 5.67 | 0.96 |
| IP00172636.3 | CaMK2d | calcium/calmodulin dependent protein kinase II delta isoform 1 | | 94.38 | NA | NA | NA | NA | 96.33 | 65.37 | 15.55 | 5.70 | 0.96 | 5.69 | 0.00 |
| IP00011102.2 | CK1d | Isoform 1 of Casein kinase I isoform delta | | 87.27 | 57.03 | 16.07 | 7.38 | 0.99 | 87.40 | 70.68 | 19.73 | 5.07 | 0.95 | 6.23 | 1.16 |
| IP00376955.5 | PCTAIRE2 | Serine/threonine protein kinase PCTAIRE 2 | | 89.09 | 68.61 | 20.04 | 5.21 | 0.97 | 90.08 | 51.43 | 19.00 | 7.84 | 1.00 | 6.52 | 1.32 |
| IP00020602.1 | CK2a2 | Casein kinase II subunit alpha' | | 87.51 | 65.47 | 14.94 | 6.17 | 0.96 | 88.57 | 53.05 | 12.82 | 8.39 | 0.99 | 7.28 | 1.11 |
| IP00029263.2 | FER | Proto oncogene tyrosine protein kinase FER | | 89.45 | 57.20 | 19.21 | 6.84 | 1.00 | 88.36 | 55.03 | 13.22 | 7.98 | 0.98 | 7.41 | 0.57 |
| IP00215786.2 | | 3',5' cyclic nucleotide phosphodiesterase 10A2 | | 94.45 | 65.16 | 25.44 | 4.87 | 0.99 | 95.68 | 39.08 | 12.07 | 10.71 | 0.94 | 7.79 | 2.92 |
| IP00646659.2 | DRAK1 | Serine/threonine protein kinase 17A | | 82.87 | 53.90 | 20.24 | 7.85 | 0.99 | 82.86 | 53.45 | 21.83 | 7.74 | 0.99 | 7.79 | 0.06 |
| IP00289357.4 | ULK1 | Serine/threonine protein kinase ULK1 | | 78.74 | 55.00 | 18.70 | 8.22 | 0.96 | 88.04 | NA | NA | NA | NA | 8.22 | 0.00 |
| IP00746301.1 | | 116 kDa protein | | 86.88 | 39.05 | 27.97 | 9.85 | 0.89 | 85.94 | 51.85 | 24.79 | 7.40 | 0.98 | 8.62 | 1.22 |
| IP00064457.2 | CDKL5 | poly (ADP-ribose) polymerase family, member 10 | | 78.09 | 58.98 | 16.51 | 7.73 | 0.94 | 75.69 | 51.52 | 13.82 | 10.16 | 0.95 | 8.95 | 1.22 |

TABLE 1-continued

| Accession No. | Kinase Name | Description | EXPERIMENT 1 Percent bound at various 16742 conc | | | | | EXPERIMENT 2 Percent bound at various 16742 conc | | | | | Kd Avg (μM) | Avg Dev |
|---|---|---|---|---|---|---|---|---|---|---|---|---|---|---|
| | | | 52 μM | 8.74 μM | 1.87 μM | Kd (μM) | R2 | 52 μM | 8.74 μM | 1.87 μM | Kd (μM) | R2 | | |
| IP10010865.1 | CK2b | Casein kinase II beta chain; | 83.37 | 42.67 | 9.52 | 12.01 | 0.99 | 85.19 | 64.17 | 13.32 | 6.66 | 0.95 | 9.34 | 2.68 |
| IP10220506.1 | MARK3 | Isoform 3 of MAP/microtubule affinity regulating kinase 3 | 85.06 | 55.59 | 25.27 | 6.71 | 0.99 | 86.79 | 36.77 | 11.59 | 12.81 | 0.98 | 9.76 | 3.05 |
| IP10028570.2 | GSK3B | Isoform 1 of Glycogen synthase kinase 3 beta | 91.30 | 51.81 | 12.33 | 8.44 | 0.98 | 88.20 | 41.97 | 8.04 | 11.58 | 0.98 | 10.01 | 1.57 |
| IP10029361.3.2 | TBK1 | Serine/threonine protein kinase TBK1 | 93.66 | 57.84 | 10.70 | 7.36 | 0.96 | 89.79 | 35.10 | 4.18 | 13.68 | 0.95 | 10.52 | 3.16 |
| IP10011633.3 | JAK1 | Tyrosine protein kinase JAK1 | 90.34 | 75.89 | 16.10 | 4.76 | 0.91 | 78.69 | 30.74 | 8.59 | 17.38 | 0.99 | 11.07 | 6.31 |
| IP10216433.2 | LIMK1 | Isoform 2 of LIM domain kinase 1 | 85.65 | 44.91 | 14.59 | 10.35 | 1.00 | 84.74 | 39.93 | 12.62 | 12.13 | 0.99 | 11.24 | 0.89 |
| IP10021917.1 | RIPK2 | Isoform 1 of Receptor interacting serine/threonine protein kinase 2 | 91.89 | 42.39 | 3.74 | 11.44 | 0.95 | 90.30 | 38.79 | 5.20 | 12.44 | 0.96 | 11.94 | 0.50 |
| IP10027729.1 | CK1e | Casein kinase I isoform epsilon | 79.64 | 34.02 | 6.91 | 16.10 | 0.99 | 88.21 | 37.16 | 7.41 | 12.98 | 0.97 | 14.54 | 1.56 |
| IP10006471.3 | MELK | Maternal embryonic leucine zipper kinase | 83.76 | 37.74 | 6.96 | 13.78 | 0.98 | 92.09 | 25.25 | 8.41 | 15.57 | 0.91 | 14.68 | 0.90 |
| IP10012443.1 | | Isoform Long of Acidic fibroblast growth factor intracellular binding protein | 66.36 | 35.39 | 14.25 | 19.19 | 0.93 | 79.33 | 45.38 | 15.03 | 11.15 | 0.99 | 15.17 | 4.02 |
| IP10465142.2 | | Hypothetical protein | 64.07 | 38.13 | 16.29 | 18.41 | 0.84 | 80.85 | 38.28 | 17.40 | 12.72 | 0.99 | 15.56 | 2.85 |
| IP10745793.1 | | G2/mitotic specific cyclin B1 | 70.32 | 33.18 | 14.34 | 18.49 | 0.98 | 77.64 | 38.93 | 10.64 | 14.29 | 1.00 | 16.39 | 2.10 |
| IP10420065.2 | | putative acyl CoA dehydrogenase | 94.11 | 21.24 | 7.63 | 16.41 | 0.88 | 96.73 | NA | NA | NA | NA | 16.41 | 0.00 |
| IP10555838.1 | GSK3A | Glycogen synthase kinase 3 alpha | 84.48 | 35.37 | 7.34 | 14.32 | 0.96 | 78.29 | 29.09 | 4.30 | 18.83 | 0.98 | 16.58 | 2.26 |
| IP10152303.5 | MARK2 | Isoform 1 of Serine/threonine protein kinase MARK2 | 75.75 | 45.68 | 5.47 | 12.64 | 0.97 | 78.93 | 24.33 | 5.83 | 20.74 | 0.97 | 16.69 | 4.05 |
| IP10022353.4 | | Phosphatidylinositol 4 phosphate 5 kinase, type II, gamma | 79.18 | 48.71 | 8.85 | 11.11 | 0.96 | 70.31 | 25.42 | 4.70 | 24.03 | 0.99 | 17.57 | 6.46 |
| IP10158248.1 | TYK2 | Non receptor tyrosine protein kinase TYK2 | 90.48 | 34.27 | 10.28 | 13.00 | 0.99 | 81.07 | 16.35 | 4.80 | 22.85 | 0.92 | 17.93 | 4.92 |
| IP10448798.4 | MAP2K5 | mitogen activated protein kinase kinase 5 isoform A | 72.51 | 26.45 | 10.27 | 21.43 | 0.95 | 82.04 | 31.43 | 16.86 | 14.87 | 0.97 | 18.15 | 3.28 |
| IP10293652.1 | CK1a | casein kinase 1, alpha 1 isoform 1 | 60.94 | 31.78 | 6.51 | 20.77 | 0.91 | 83.66 | 34.46 | 5.11 | 16.85 | 0.98 | 18.81 | 1.96 |
| IP10293652.1 | IRAK1 | Isoform 1 of Interleukin 1 receptor associated kinase 1 | 86.24 | 19.01 | 6.84 | 19.54 | 0.98 | 92.34 | 17.85 | 5.21 | 18.25 | 0.87 | 18.90 | 0.64 |
| IP10225698.2 | LIMK2 | LIM domain kinase 2 isoform 1 | 77.17 | 26.61 | 7.76 | 19.75 | 0.94 | 81.10 | 25.37 | 9.42 | 18.54 | 0.97 | 19.14 | 0.60 |
| IP10220642.6 | | 14 3 3 protein gamma | 66.26 | 29.65 | 15.84 | 22.03 | 0.92 | 70.62 | 36.47 | 16.87 | 16.38 | 0.95 | 19.21 | 2.83 |
| IP10013890.1 | | 14 3 3 protein sigma | 64.66 | 26.55 | 16.70 | 24.62 | 0.94 | 75.16 | 39.83 | 13.01 | 14.23 | 0.99 | 19.43 | 5.19 |
| IP10219510.1 | KHS2 | Isoform 3 of Mitogen activated protein kinase kinase kinase 3 | 80.83 | 21.37 | 11.86 | 19.86 | | 73.60 | NA | NA | NA | NA | 19.86 | 0.00 |
| IP10013905.1 | | 5' AMP activated protein kinase subunit beta 2 | 75.10 | 35.62 | 28.74 | 13.18 | 0.76 | 66.35 | 22.25 | 3.76 | 28.36 | 1.00 | 20.77 | 7.59 |
| IP10151170.4 | TTK | TTK protein kinase | 78.07 | 25.50 | 6.43 | 20.06 | 0.98 | 74.84 | 24.47 | 5.99 | 21.97 | 0.98 | 21.02 | 0.95 |
| IP10465101.5 | NEK3 | cDNA FLJ16392 moderately similar to PU Mus musculus serine/threonine protein | 80.27 | 19.21 | 6.25 | 21.80 | 0.94 | 87.40 | NA | NA | NA | NA | 21.80 | 0.00 |
| IP10220409.2 | | 5' AMP activated protein kinase subunit beta 1 | 76.30 | 31.58 | 9.48 | 17.72 | 1.00 | 71.37 | 19.16 | 3.94 | 26.69 | 0.97 | 22.20 | 4.48 |
| IP10749256.1 | FAK | PTK2 protein tyrosine kinase 2 isoform b variant (Fragment) | 66.44 | 13.68 | 4.90 | 23.58 | 0.96 | 84.20 | 23.10 | 14.24 | 21.37 | 0.93 | 22.47 | 1.10 |
| IP10168907.1 | | Inositol polyphosphate multikinase | 76.48 | 25.73 | 5.87 | 20.70 | 0.98 | 79.14 | 15.02 | 5.03 | 24.25 | 0.92 | 22.48 | 1.78 |
| IP10000878.3 | TEC | Tyrosine protein kinase Tec | 68.89 | 24.83 | 5.66 | 24.99 | 1.00 | 79.09 | 24.01 | 6.19 | 20.31 | 0.97 | 22.65 | 2.34 |
| IP10015809.1 | | Probable O sialoglycoprotein endopeptidase | 83.80 | 14.76 | 8.48 | 21.82 | 0.89 | 82.06 | 10.99 | 5.68 | 24.48 | 0.88 | 23.15 | 1.33 |
| IP10307755.3 | AMPKa1 | 5' AMP activated protein kinase catalytic subunit alpha 2 | 73.97 | 24.30 | 6.68 | 20.25 | 0.99 | 69.44 | 20.73 | 4.41 | 27.00 | 0.99 | 23.63 | 3.37 |
| IP10012318.2 | MAP3K1 | PREDICTED: mitogen activated protein kinase kinase kinase 1 | 71.88 | 24.16 | 6.46 | 23.50 | 0.99 | 73.42 | 22.44 | 4.91 | 23.78 | 0.98 | 23.64 | 0.14 |
| IP10016613.2 | CK2a1 | CSNK2A1 protein | 74.51 | 27.35 | 3.69 | 21.19 | 0.99 | 69.82 | 21.81 | 1.98 | 26.62 | 0.98 | 23.90 | 2.71 |
| IP10413318.3 | | Highly similar to 5' AMP ACTIVATED PROTEIN KINASE, GAMMA 1 SUBUNIT | 72.68 | 28.05 | 5.77 | 21.36 | 1.00 | 67.52 | 23.62 | 5.08 | 26.58 | 1.00 | 23.97 | 2.61 |
| IP10000816.1 | | 14 3 3 protein epsilon | 68.65 | 28.18 | 17.01 | 21.29 | 0.94 | 64.48 | 24.78 | 11.54 | 26.80 | 0.98 | 24.05 | 2.75 |
| IP10479349.1 | | OTTHUMP00000017246 | 69.99 | 24.06 | 9.34 | 24.09 | 0.99 | 71.42 | NA | NA | NA | NA | 24.09 | 0.00 |
| IP10298949.1 | SGK | Cyclin G associated kinase | 69.07 | 29.77 | 8.35 | 21.85 | 1.00 | 63.94 | 27.34 | 6.15 | 26.72 | 0.99 | 24.28 | 2.43 |
| IP10021263.3 | GAK | 14 3 3 protein zeta/delta | 58.91 | 28.04 | 14.84 | 28.42 | 0.87 | 63.62 | 35.41 | 15.07 | 20.42 | 0.88 | 24.42 | 4.00 |

TABLE 1-continued

| | Kinase | | | EXPERIMENT 1 | | | | | EXPERIMENT 2 | | | | |
| --- | --- | --- | --- | --- | --- | --- | --- | --- | --- | --- | --- | --- | --- |
| | | | | Percent bound at various 16742 conc | | | | | Percent bound at various 16742 conc | | | | |
| Accession No. | Name | Description | 52 µM | 8.74 µM | 1.87 µM | Kd (µM) | R2 | 52 µM | 8.74 µM | 1.87 µM | Kd (µM) | R2 | Kd Avg (µM) | Avg Dev |
| IP100011416.2 | | Delta3,5 delta2,4 dienoyl CoA isomerase, mitochondrial precursor | 88.63 | 4.36 | 2.29 | 24.63 | 0.81 | 88.46 | 4.42 | 2.13 | 24.70 | 0.81 | 24.67 | 0.03 |
| IP100000977.1 | MLK3 | Mitogen activated protein kinase kinase kinase 11 | 77.37 | 14.34 | 5.23 | 25.41 | 0.92 | 67.93 | 25.48 | 8.25 | 24.75 | 1.00 | 25.08 | 0.33 |
| IP100022536.1 | MSK2 | Isoform 1 of Ribosomal protein S6 kinase alpha 4 | 80.88 | 18.88 | 5.99 | 21.72 | 0.94 | 74.79 | 11.51 | 2.67 | 28.55 | 0.92 | 25.13 | 3.41 |
| IP100217362.1 | | CGI 121 L1 isoform | 76.66 | NA | NA | NA | NA | 79.35 | 5.60 | 3.53 | 28.47 | 0.85 | 28.47 | 0.00 |
| IP100005142.1 | FGFR1 | Isoform 1 of Basic fibroblast growth factor receptor 1 precursor | 70.53 | 25.70 | 4.68 | 23.77 | 0.99 | 62.77 | 17.77 | 2.86 | 34.00 | 0.99 | 28.89 | 5.12 |
| IP100290305.3 | PRPK | TP53 regulating kinase | 77.06 | 7.74 | 3.26 | 28.86 | 0.88 | 74.11 | 6.07 | 2.66 | 31.61 | 0.88 | 30.23 | 1.37 |
| IP100301432.1 | | My019 protein | 77.51 | 7.38 | 2.52 | 28.87 | 0.88 | 73.73 | 4.94 | 4.71 | 32.11 | 0.87 | 30.49 | 1.62 |
| IP100026689.4 | CDC2 | Hypothetical protein DKFZp686L20222 | 71.74 | 13.98 | 2.49 | 29.29 | 0.94 | 71.71 | 8.94 | 1.46 | 32.02 | 0.91 | 30.66 | 1.37 |
| IP100029702.1 | PYK2 | Isoform 1 of Protein tyrosine kinase 2 beta | 66.90 | 18.59 | 4.05 | 29.96 | 0.99 | 65.35 | 16.97 | 4.26 | 32.03 | 0.98 | 30.99 | 1.04 |
| IP100001477.1 | DDR1 | | 64.85 | 23.82 | 3.72 | 28.57 | 1.00 | 65.72 | 10.81 | 5.18 | 35.11 | 0.95 | 31.84 | 3.27 |
| IP100005142.1 | | Isoform 1 of Basic fibroblast growth factor receptor 1 precursor | 73.70 | 6.55 | 0.33 | 32.00 | 0.88 | 61.49 | NA | NA | NA | NA | 32.00 | 0.00 |
| IP100440727.1 | BRD4 | Isoform 1 of Bromodomain containing protein 4 | 68.49 | 15.74 | 4.14 | 30.34 | 0.97 | 66.40 | 12.63 | 3.00 | 33.88 | 0.96 | 32.11 | 1.77 |
| IP100002538.1 | PDK1 | Isoform 1 of 3 phosphoinositide dependent protein kinase 1 | 73.55 | 6.46 | 1.85 | 31.91 | 0.88 | 73.35 | 5.37 | 1.68 | 32.62 | 0.88 | 32.27 | 0.35 |
| IP100017305.2 | RSK3 | Ribosomal protein S6 kinase alpha 1 | 71.55 | 0.00 | 0.00 | 36.95 | 0.84 | 65.82 | 11.86 | 8.24 | 33.89 | 0.95 | 35.42 | 1.53 |
| IP100014266.1 | BRD3 | Isoform 1 of Bromodomain containing protein 3 | 65.30 | 14.08 | 4.34 | 33.73 | 0.97 | 63.27 | 9.07 | 5.18 | 38.62 | 0.94 | 36.17 | 2.44 |
| IP100413780.1 | PKN3 | Serine/threonine protein kinase N3 | 66.97 | 17.01 | 4.79 | 30.65 | 0.98 | 57.74 | 13.05 | 4.03 | 42.27 | 0.99 | 36.46 | 5.81 |
| IP100221275.4 | EphB2 | Isoform 1 of Ephrin type B receptor 2 precursor | 62.69 | 25.17 | 4.07 | 29.34 | 0.99 | 54.74 | 15.31 | 2.86 | 44.27 | 1.00 | 36.81 | 7.46 |
| IP100013981.3 | YES | Proto oncogene tyrosine protein kinase Yes | 70.05 | 5.40 | 1.41 | 35.12 | 0.89 | 65.58 | 5.90 | 3.61 | 38.55 | 0.91 | 36.83 | 1.72 |
| IP100074267.1 | Erk2 | Mitogen activated protein kinase 1 | 49.33 | 23.19 | 6.16 | 45.23 | 0.93 | 66.42 | 8.58 | 2.43 | 35.89 | 0.93 | 40.56 | 4.67 |
| IP100289342.7 | MAST2 | microtubule associated serine/threonine kinase 2 | 63.78 | 9.80 | 3.18 | 37.83 | 0.95 | 58.06 | 10.45 | 4.53 | 43.85 | 0.97 | 40.84 | 3.01 |
| IP100216470.1 | MAST3 | Isoform 1 of Phosphatidylinositol 4 phosphate 5 kinase type 2 beta | 58.23 | 17.93 | 4.91 | 37.98 | 1.00 | 55.61 | 11.02 | 2.91 | 46.35 | 0.98 | 42.17 | 4.18 |
| IP100294881.1 | | Isoform A of Ketohexokinase | 60.80 | 65.73 | 2.62 | 45.99 | 0.89 | 65.56 | 4.09 | 2.80 | 39.56 | 0.89 | 42.77 | 3.22 |
| IP100470811.3 | SNRK | Isoform 1 of SNF related serine/threonine protein kinase | 55.13 | 58.22 | 5.63 | 41.36 | 0.97 | 58.09 | 8.91 | 2.86 | 44.66 | 0.96 | 43.01 | 1.65 |
| IP100011488.3 | MST1 | Serine/threonine protein kinase 4 | 66.66 | 6.04 | 4.63 | 37.11 | 0.90 | 57.75 | 2.89 | 1.84 | 49.39 | 0.91 | 43.25 | 6.14 |
| IP100014068.1 | PAK4 | Isoform 1 of Serine/threonine protein kinase PAK4 | 58.35 | 12.12 | 2.84 | 42.17 | 0.98 | 57.23 | 10.45 | 2.51 | 44.73 | 0.97 | 43.45 | 1.28 |
| IP100289342.1 | EphB4 | Ephrin type B receptor 4 precursor | 61.05 | 18.14 | 3.95 | 35.16 | 1.00 | 50.80 | 12.85 | 2.71 | 52.10 | 1.00 | 43.63 | 8.47 |
| IP100009688.1 | | Phosphatidylinositol 4 phosphate 5 kinase type 2 alpha | 62.04 | 16.91 | 4.38 | 34.92 | 0.99 | 49.22 | 15.42 | 3.81 | 52.38 | 0.99 | 43.65 | 8.73 |
| IP100291215.4 | | B aggressive lymphoma 28 | 57.30 | 15.01 | 2.90 | 41.43 | 0.99 | 50.54 | 11.10 | 2.48 | 53.98 | 0.99 | 47.70 | 6.27 |
| IP100296992.6 | AXL | AXL receptor tyrosine kinase isoform 1 | 60.74 | 8.51 | 3.58 | 41.69 | 0.95 | 50.79 | 6.87 | 2.59 | 56.92 | 0.96 | 49.31 | 7.62 |
| IP100020454.1 | | Deoxycytidine kinase | 52.00 | 3.09 | 0.41 | 58.30 | 0.92 | 64.81 | 3.24 | 1.56 | 41.00 | 0.89 | 49.65 | 8.65 |
| IP100000685.1 | CDK7 | Cell division protein kinase 7 | 53.96 | 22.04 | 5.76 | 39.85 | 0.98 | 45.57 | 13.18 | 2.34 | 61.48 | 1.00 | 50.67 | 10.82 |
| IP100017083.4 | CaMKK1 | Isoform 1 of Calcium/calmodulin dependent protein kinase kinase 1 | 63.34 | 10.67 | 2.08 | 37.92 | 0.95 | 47.32 | 6.65 | 1.46 | 63.90 | 0.97 | 50.91 | 12.99 |
| IP100306406.3 | RIOK2 | Serine/threonine protein kinase RIO2 | 58.06 | 11.61 | 4.37 | 42.57 | 0.98 | 48.34 | 7.91 | 1.55 | 60.79 | 0.98 | 51.68 | 9.11 |
| IP100134067.4 | BUB1 | Mitotic checkpoint serine/threonine protein kinase BUB1 | 50.46 | 11.95 | 2.46 | 53.44 | 0.99 | 47.87 | NA | NA | NA | NA | 53.44 | 0.00 |
| IP100074258.3 | MASTL | Isoform 1 of Microtubule associated serine/threonine protein kinase like | 51.63 | 9.59 | 0.55 | 53.79 | 0.98 | 62.29 | NA | NA | NA | NA | 53.79 | 0.00 |
| IP100053803.3 | MAP3K2 | Mitogen activated protein kinase kinase kinase 2 | 49.07 | 14.72 | 4.06 | 53.15 | 1.00 | 48.40 | 14.47 | 3.52 | 54.66 | 1.00 | 53.91 | 0.75 |
| IP100017726.1 | | hydroxyacyl Coenzyme A dehydrogenase, type II isoform 1 | 62.08 | 4.37 | 4.41 | 42.68 | 0.90 | 41.03 | 10.79 | 8.75 | 72.75 | 0.94 | 57.72 | 15.03 |
| IP100221267.1 | EphA2 | Ephrin type A receptor 2 precursor | 54.66 | 13.88 | 3.91 | 45.35 | 1.00 | 43.73 | 7.66 | 2.12 | 70.80 | 0.99 | 58.08 | 12.72 |
| IP100474269.1 | PITSLRE | 92 kDa protein | 49.06 | 12.03 | 1.13 | 56.07 | 0.99 | 46.71 | 4.78 | 2.00 | 66.72 | 0.96 | 61.40 | 5.33 |
| IP100337659.1 | TLK2 | Isoform 2 of Serine/threonine protein kinase tousled like 2 | 58.72 | 3.89 | 2.49 | 47.33 | 0.91 | 41.78 | 3.73 | 1.24 | 79.97 | 0.96 | 63.65 | 16.32 |
| IP100018195.1 | Erk1 | Mitogen activated protein kinase 3 | 52.52 | 2.41 | 1.06 | 57.80 | 0.92 | 45.83 | 2.38 | 0.91 | 71.10 | 0.93 | 64.45 | 6.65 |

TABLE 1-continued

| Kinase | | | | EXPERIMENT 1 | | | | | EXPERIMENT 2 | | | | |
|---|---|---|---|---|---|---|---|---|---|---|---|---|---|
| | | | | Percent bound at various 16742 conc | | | | | Percent bound at various 16742 conc | | | Kd Avg | Avg |
| Accession No. | Name | Description | 52 μM | 8.74 μM | 1.87 μM | Kd (μM) | R2 | 52 μM | 8.74 μM | 1.87 μM | Kd (μM) | R2 | (μM) | Dev |
| IPI00018873.1 | | Isoform 1 of Nicotinamide phosphoribosyltransferase | 54.03 | 2.70 | 2.80 | 54.76 | 0.91 | 41.68 | 3.40 | 2.28 | 80.33 | 0.95 | 67.54 | 12.78 |
| IPI00339361.5 | TLK1 | Isoform 1 of Serine/threonine protein kinase tousled like 1 | 49.12 | 2.39 | 1.34 | 63.98 | 0.92 | 31.56 | 1.97 | 0.76 | 120.90 | 0.96 | 92.44 | 28.46 |
| IPI00219250.1 | DYRK1A | Isoform 1 of Dual specificity tyrosine phosphorylation regulated kinase 1A | 52.16 | 14.82 | 5.75 | 47.78 | 1.00 | 28.11 | 3.76 | 1.08 | 137.32 | 0.99 | 92.55 | 44.77 |
| IPI00174469.1 | | Sepiapterin reductase | 51.84 | 2.59 | 2.16 | 58.59 | 0.92 | 30.43 | 1.52 | 1.04 | 127.45 | 0.95 | 93.02 | 34.43 |
| IPI00006372.3 | | Testis expressed sequence 264 protein precursor | 51.05 | 2.55 | 2.22 | 60.01 | 0.92 | 24.69 | 1.91 | 2.11 | 165.29 | 0.97 | 112.65 | 52.64 |
| IPI00221141.2 | p38a | Isoform CSBP1 of Mitogen activated protein kinase 14 | 49.78 | 6.72 | 4.98 | 58.33 | 0.96 | 24.52 | 1.43 | 3.02 | 167.25 | 0.95 | 112.79 | 54.46 |
| IPI00012891.1 | PHKg2 | Phosphorylase b kinase gamma catalytic chain, testis/liver isoform | 59.42 | NA | NA | NA | NA | 27.11 | 2.29 | 1.94 | 146.21 | 0.97 | 146.21 | 0.00 |
| IPI00479216.1 | MAP3K5 | Mitogen activated protein kinase kinase kinase 5 variant | 56.90 | 10.05 | 7.42 | 44.47 | 0.96 | 17.64 | 1.00 | 1.27 | 251.55 | 0.97 | 148.01 | 103.54 |
| IPI00418221.2 | MAP3K6 | mitogen activated protein kinase kinase kinase 6 | 51.68 | 3.57 | 4.37 | 57.65 | 0.93 | 13.37 | 3.94 | 2.67 | 325.95 | 0.91 | 191.80 | 134.15 |

Footnotes:
NA implies that the protein hit could not be identified in either IVA1 or IVA2 setting of that experiment and therefore no values were assigned
$R^2$ value is a measure of goodness of curve fit while fitting data to deduce the Kd values
Kd average is the average of Kd values obtained from two experiment or the single Kd value if obtained from only one of the experiments

TABLE 2

| IPI number | Kinase name | Description | PERCENT BOUND IN PRESENCE OF SB203580 | | | | $K_i$ ($\mu M$) | $R^2$ | $K_d$ ($\mu M$) | $EC_{50}$ |
| | | | 0.1 $\mu M$ | 1 $\mu M$ | 10 $\mu M$ | 100 $\mu M$ | | | | |
|---|---|---|---|---|---|---|---|---|---|---|
| IPI00021917.1 | RIPK2 | Isoform 1 of Receptor interacting serine/threonine protein kinase 2 | 37.17 | 8.75 | 1.83 | 1.74 | 0.01 | 0.98 | 11.94 | 0.06 |
| IPI00234463.4 | CK1d | Isoform 1 of Casein kinase 1 isoform delta | 107.15 | 28.21 | 7.11 | 0.00 | 0.08 | 0.92 | 6.23 | 0.63 |
| IPI00298949.1 | GAK | Cyclin G associated kinase | 107.77 | 34.13 | 6.62 | 2.61 | 0.26 | 0.94 | 24.28 | 0.74 |
| IPI00027729.1 | CK1e | Casein kinase 1 isoform epsilon | 116.64 | 44.73 | 22.07 | 3.06 | 0.30 | 0.89 | 14.54 | 1.26 |
| IPI00024673.2 | JNK2 | Isoform Alpha 2 of Mitogen activated protein kinase 9 | 90.73 | 94.06 | 47.75 | 12.38 | 0.27 | 0.98 | 1.30 | 9.85 |
| IPI00448798.4 | CK1a | casein kinase 1, alpha 1 isoform 1 | 141.81 | 85.08 | 44.18 | 6.68 | 2.33 | 0.81 | 18.81 | 8.03 |
| IPI00216190.1 | GSK3B | Isoform 1 of Glycogen synthase kinase 3 beta | 105.84 | 115.61 | 51.89 | 14.41 | 2.52 | 0.91 | 10.01 | 14.16 |
| IPI00292228.1 | GSK3A | Glycogen synthase kinase 3 alpha | 107.81 | 85.69 | 65.85 | 17.05 | 4.89 | 0.97 | 16.58 | 18.50 |
| IPI00440727.1 | BRD4 | Isoform 1 of Bromodomain containing protein 4 | 183.06 | 104.28 | 97.08 | 19.20 | 18.54 | 0.45 | 32.00 | 45.27 |
| IPI00021267.1 | EphA2 | Ephrin type A receptor 2 precursor | 136.43 | 75.38 | 80.09 | 18.42 | 15.77 | 0.73 | 58.08 | 28.30 |
| IPI00011633.3 | JAK1 | Tyrosine protein kinase JAK1 | 203.68 | 100.46 | 138.51 | 38.23 | 21.64 | 0.09 | 11.07 | 111.80 |
| IPI00289342.1 | EphB4 | Ephrin type B receptor 4 precursor | 151.62 | 102.64 | 87.82 | 26.17 | 22.06 | 0.65 | 43.63 | 45.39 |
| IPI00219421.3 | EphB2 | Isoform 1 of Ephrin type B receptor 2 precursor | 130.30 | 104.75 | 87.28 | 31.36 | 22.95 | 0.81 | 36.46 | 52.00 |
| IPI00013981.3 | YES | Proto oncogene tyrosine protein kinase Yes | 123.32 | 110.31 | 107.16 | 42.55 | 42.35 | 0.75 | 36.81 | 95.44 |
| IPI00014266.1 | BRD3 | Isoform 1 of Bromodomain containing protein 3 | 93.71 | 85.85 | 50.02 | 12.67 | 4.24 | 0.98 | 35.42 | 9.76 |
| IPI00216470.1 | 0 | Isoform 1 of Phosphatidylinositol-4-phosphate 5-kinase type-2 beta | 117.97 | 93.15 | 97.49 | 48.90 | 49.28 | 0.84 | 42.17 | 103.20 |
| IPI00018195.1 | Erk1 | Mitogen activated protein kinase 3 | 110.13 | 93.40 | 86.38 | 48.19 | 51.14 | 0.93 | 64.45 | 87.76 |
| IPI00017469.1 | 0 | Sepiapterin reductase | 109.59 | 62.47 | 95.01 | 32.00 | 36.50 | 0.59 | 93.02 | 54.61 |

TABLE 3

Quantitative proteomic analysis of cellular gefitinib targets

| $PK^a$ | r (% BOUND)$^b$ | $K_i$ (AX14596)$^c$ [$\mu M$] | $IC_{50}$ (GEF.)$^c$ [$\mu M$] | $K_i$ (GEF.)$^c$ [$\mu M$] | $IC_{50,ka}$ (GEF.)$^d$ [$\mu M$] |
|---|---|---|---|---|---|
| RIPK2 | 0.06 (94%) | 6.2 | 3.8 | 0.22 | 0.046 |
| EGFR | 0.31 (69%) | 44 | 0.51 | 0.16 | 0.005 |
| BRK | 0.31 (69%) | 45 | 2.8 | 0.86 | 0.28 |
| GAK | 0.45 (55%) | 82 | 0.10 | 0.046 | 0.035 |
| JNK2 | 0.52 (48%) | 110 | 2.1 | 1.1 | 6.0 |
| LYN | 0.66 (34%) | 195 | 3.2 | 2.1 | 0.41 |
| EphB4 | 0.71 (29%) | 242 | 1.4 | 0.96 | 0.42 |
| MET | 0.73 (27%) | 267 | 1.7 | 1.2 | 5.5 |
| YES | 0.87 (13%) | 658 | 9.4 | 8.1 | 1.3 |

TABLE 4

| EXPT | DESCRIPTION | IMMOBILIZED INHIBITOR [$\mu M$] | LABELS | RATIOS |
|---|---|---|---|---|
| 1 | $K_f$ DETERMINATION AX14596 - RECIPROCAL LABELING SCHEME | 100.1 | L: 2ND ELUATE FROM AX14596 BEADS<br>M: ELUATE FROM CONTROL BEADS<br>H: 1ST ELUATE FROM AX14596 BEADS | $R_1$(2. INC/1. INC) = L/H NORMALIZED 1<br>$R_1$(CONTROL/1. INC) = M/H NORMALIZED 1 |
| 2 | $K_f$ DETERMINATION AX14596 - NORMAL LABELING SCHEME | 100.1 | L: 1ST ELUATE FROM AX14596 BEADS<br>M: ELUATE FROM CONTROL BEADS<br>H: 2ND ELUATE FROM AX14596 BEADS | $R_2$(2. INC/1. INC) = H/L NORMALIZED 2<br>$R_2$(CONTROL/1. INC) = M/L NORMALIZED 2 |
| 3 | $K_f$ DETERMINATION AX14596 - LIGAND CONCENTRATION CONTROL | 100.1 | L: INCUBATION OF 3 MG PROTEIN WITH AX14596 BEADS<br>H: INCUBATION OF 1 MG PROTEIN WITH AX14596 BEADS | R(3 MG/1 MG LYSATE) = L/H NORMALIZED 3 |
| 4 | $K_f$ DETERMINATION AX14596 - INCUBATION TIME CONTROL | 100.1 | L: 5 H INCUBATION TIME<br>H: 2.5 H INCUBATION TIME | R(5 H/2.5 H INC. TIME) = L/H NORMALIZED 4 |
| 5 | $IC_{50}$ DETERMINATION GEFITINIB - | 100.1 | L: COMPETITION WITH 0 nM AX14596 | $R_1$(10 nM/0 nM GEF.) = M/L NORMALIZED 5 |

TABLE 4-continued

| EXPT | DESCRIPTION | IMMOBILIZED INHIBITOR [μM] | LABELS | RATIOS |
|---|---|---|---|---|
| | 0, 0.01, 0.1 μM - EXPERIMENT 1 | | M: COMPETITION WITH 10 nM AX14596<br>H: COMPETITION WITH 100 nM AX14596 | $R_1$(100 nM/0 nM GEF.) = H/L NORMALIZED 5 |
| 6 | $IC_{50}$ DETERMINATION GEFITINIB -<br>0, 1, 10 μM - EXPERIMENT 1 | 100.1 | L: COMPETITION WITH 0 nM AX14596<br>M: COMPETITION WITH 1000 nM AX14596<br>H: COMPETITION WITH 10000 nM AX14596 | $R_1$(1000 nM/0 nM GEF.) = M/L NORMALIZED 6<br>$R_1$(10000 nM/0 nM GEF.) = H/L NORMALIZED 6 |
| 7 | $IC_{50}$ DETERMINATION GEFITINIB -<br>0, 0.01, 0.1 μM - EXPERIMENT 2 | 100.1 | L: COMPETITION WITH 0 nM AX14596<br>M: COMPETITION WITH 10 nM AX14596<br>H: COMPETITION WITH 100 nM AX14596 | $R_2$(10 nM/0 nM GEF.) = M/L NORMALIZED 7<br>$R_2$(100 nM/0 nM GEF.) = H/L NORMALIZED 7 |
| 8 | $IC_{50}$ DETERMINATION GEFITINIB -<br>0, 1, 10 μM- EXPERIMENT 2 | 100.1 | L: COMPETITION WITH 0 nM AX14596<br>M: COMPETITION WITH 1000 nM AX14596<br>H: COMPETITION WITH 10000 nM AX14596 | $R_2$(1000 nM/0 nM GEF.) = M/L NORMALIZED 8<br>$R_2$(10000 nM/0 nM GEF.) = H/L NORMALIZED 8 |

TABLE 5

| Leading Protein | PK | GENE | $r_{AVERAGE}$ (2. inc/1. inc) | $K_i$ (AX14596) [uM] | $r_{AVERAGE}$ (control/1. inc) | r (3 mg/1 mg lysate) | r (5 h/2.5 h inc. time) | $r_{AVERAGE}$ (10 nM/0 nM Gef.) | $r_{AVERAGE}$ (100 nM/0 nM Gef.) | $r_{AVERAGE}$ (1000 nM/0 nM Gef.) | $r_{AVERAGE}$ (10000 nM/0 nM Gef.) | $IC_{50}$ (Gef.) [nM] | $K_i$ (Gef) [nM] | $IC_{50}$–$K_i$ [nM], kinase assay (Gef) |
|---|---|---|---|---|---|---|---|---|---|---|---|---|---|---|
| IPI00021917 | RIPK2 | RIPK2 | 0.06 | 6.19 | 0.02 | 2.68 | 0.90 | 0.74 | 1.03 | 0.74 | 0.31 | 3757 | 218.91 | 46.12 |
| IPI00027778 | | NUDT12 | 0.14 | 16.14 | 0.04 | 2.24 | 0.91 | 1.04 | 0.93 | 0.92 | 0.09 | 3221 | 447.35 | |
| IPI00018873 | | NAMPT | 0.29 | 41.20 | 0.04 | 7.48 | 0.39 | 0.71 | 0.74 | 0.73 | 0.92 | | | |
| IPI00018274 | EGFR | EGFR | 0.31 | 44.48 | 0.03 | 2.65 | 0.90 | 0.70 | 0.88 | 0.33 | 0.06 | 512.3 | 157.61 | 5.58 |
| IPI00015927 | BRK | PTK6 | 0.31 | 45.43 | 0.02 | 2.56 | 0.96 | 0.86 | 0.96 | 0.75 | 0.20 | 2760 | 861.60 | 279.50 |
| IPI00873294 | | BLMH | 0.35 | 53.58 | 0.08 | 11.91 | 1.31 | 0.82 | 0.53 | 0.43 | 0.11 | 223.4 | 77.89 | |
| IPI00298949 | GAK | GAK | 0.45 | 82.05 | 0.04 | 2.59 | 1.05 | 0.80 | 0.53 | 0.13 | 0.02 | 101.2 | 45.59 | 35.24 |
| IPI00028081 | CaMK2d | CAMK2D | 0.47 | 87.22 | 0.07 | 2.54 | 1.13 | 0.89 | 1.11 | 0.91 | 0.93 | | | |
| IPI00016572 | | SNRPG | 0.47 | 87.62 | 0.16 | 2.54 | | 0.65 | 1.09 | 0.72 | 0.89 | | | |
| IPI00646849 | CaMK2g | CAMK2G | 0.48 | 93.37 | 0.04 | 2.45 | 1.17 | 0.95 | 1.08 | 1.01 | 0.92 | | | |
| IPI00029266 | | SNRPE | 0.51 | 105.76 | 0.07 | 2.57 | 1.88 | 0.70 | 1.11 | 0.74 | 0.93 | | | |
| IPI00418639 | | ACAD10 | 0.52 | 107.62 | 0.08 | 8.45 | 0.48 | 1.17 | 0.86 | 1.07 | 0.24 | | | |
| IPI00024673 | JNK2 | MAPK9 | 0.52 | 109.65 | 0.03 | 2.58 | 0.95 | 0.86 | 0.94 | 0.68 | 0.18 | 5531 | 2865.59 | 5964.67 |
| IPI00221141 | p38a | MAPK14 | 0.63 | 167.83 | 0.03 | 2.87 | | 0.88 | 0.97 | 0.97 | 0.64 | 2130 | 1113.49 | |
| IPI00304648 | SgK085 | MYLK3 | 0.65 | 185.78 | 0.00 | 2.56 | 0.97 | 0.97 | 1.01 | 0.98 | 0.53 | | | |
| IPI00872474 | LYN | LYN | 0.66 | 195.32 | 0.07 | 2.14 | 0.98 | 0.85 | 1.00 | 0.69 | 0.31 | 11960 | 7772.27 | 406.85 |
| IPI00029219 | ALK2 | ACVR1 | 0.67 | 201.86 | 0.15 | 2.57 | 1.17 | 0.76 | 1.25 | 0.77 | 0.85 | 3237 | 2140.18 | |
| IPI00021275 | EphB2 | EPHB2 | 0.68 | 213.19 | 0.04 | 3.41 | 1.06 | 0.88 | 0.90 | 0.85 | 0.33 | 4980 | 3388.83 | |
| IPI00289342 | EphB4 | EPHB4 | 0.71 | 241.53 | 0.05 | 2.65 | 0.96 | 0.79 | 0.89 | 0.58 | 0.14 | 1351 | 955.15 | 424.30 |
| IPI00029273 | MET | MET | 0.73 | 266.54 | 0.06 | 2.30 | 1.12 | 0.74 | 1.00 | 0.57 | 0.23 | 1661 | 1207.51 | 5462.33 |
| IPI00002857 | p38a | MAPK14 | 0.77 | 331.74 | 0.06 | 2.74 | 1.15 | 0.88 | 1.04 | 0.92 | 0.64 | | | |
| IPI00008557 | | IGF2BP1 | 0.79 | 367.24 | 0.19 | | | | | | | | | |
| IPI00009334 | PKD2 | PRKD2 | 0.79 | 385.13 | 0.08 | 2.53 | 0.96 | 0.85 | 0.97 | 0.84 | 0.38 | 5883 | 4669.36 | |
| IPI00027983 | | CDA | 0.80 | 402.28 | 0.09 | 3.09 | | 0.90 | 1.03 | 0.96 | 0.77 | | | |
| IPI00018981 | YES | YES1 | 0.87 | 658.37 | 0.05 | 2.03 | 0.98 | 0.94 | 1.15 | 0.86 | 0.49 | 9385 | 8146.40 | 1343.30 |
| IPI00304048 | MNK1 | MKNK1 | 0.90 | 921.63 | 0.04 | 2.94 | 1.05 | 0.76 | 1.00 | 0.73 | 0.37 | 4429 | 3995.09 | |
| IPI00015538 | PKD3 | PRKD3 | 0.94 | 1508.12 | 0.08 | 2.49 | 1.05 | 0.98 | 1.05 | 0.98 | 0.41 | 8213 | 7701.80 | |
| IPI00017469 | | SPR | 0.95 | 1858.55 | 0.02 | 2.91 | 2.43 | 1.04 | 1.10 | 1.01 | 0.77 | | | |
| IPI00479315 | | RPL7A | 0.95 | 2103.58 | 0.17 | 5.23 | | 0.92 | 0.88 | 0.59 | 0.79 | | | |
| IPI00472171 | | RPL7 | 0.96 | 2313.35 | 0.19 | 1.82 | | 0.84 | 1.08 | 0.86 | 0.98 | | | |
| IPI00398135 | | RPL27A | 0.97 | 2929.01 | 0.06 | 1.75 | 1.12 | 0.87 | 1.05 | 0.81 | 1.03 | | | |
| IPI00027729 | CK1e | CSNK1E | 0.98 | 4082.93 | 0.09 | 2.87 | 1.23 | 0.80 | 1.00 | 0.84 | 0.59 | 13050 | 12737.71 | |

TABLE 6

| PK | INHIBITOR | $K_i$ - CHEMICAL PROTEOMICS | $K_i$ ($IC_{50}$ - CHEMICAL PROTEOMICS) | $K_i$ - KINASE ASSAY | $Log_{10}$ ($K_i$ - KINASE ASSAY) | $K_i$ (ka)/ $K_i$ (cp) | $Log_{10}$ [$K_i$ (ka)/ $K_i$ (cp)] |
|---|---|---|---|---|---|---|---|
| JNK2 | SB203580 | 918.88 | 2.96 | 727.55 | 2.86 | 1.26 | 0.10 |
| RIPK2 | SB203580 | 0.83 | −0.08 | 2.16 | 0.33 | 0.38 | −0.42 |
| GSK3B | SB203580 | 1161.76 | 3.07 | 3117.00 | 3.49 | 0.37 | −0.43 |
| CK1d | SB203580 | 174.52 | 2.24 | 150.90 | 2.18 | 1.16 | 0.06 |
| CK1e | SB203580 | 648.90 | 2.81 | 415.05 | 2.62 | 1.56 | 0.19 |
| GAK | SB203580 | 109.20 | 2.04 | 35.24 | 1.55 | 3.10 | 0.49 |
| YES | SB203580 | 21566.34 | 4.33 | 4379.00 | 3.64 | 4.92 | 0.69 |
| EphB4 | SB203580 | 13955.00 | 4.14 | 37714.50 | 4.58 | 0.37 | −0.43 |
| RIPK2 | Gefitinib | 218.91 | 2.34 | 46.12 | 1.66 | 4.75 | 0.68 |
| EGFR | Gefitinib | 157.61 | 2.20 | 5.58 | 0.75 | 28.26 | 1.45 |
| BRK | Gefitinib | 861.60 | 2.94 | 279.50 | 2.45 | 3.08 | 0.49 |
| GAK | Gefitinib | 45.59 | 1.66 | 35.24 | 1.55 | 1.29 | 0.11 |
| JNK2 | Gefitinib | 1113.49 | 3.05 | 5964.67 | 3.78 | 0.19 | −0.73 |
| LYN | Gefitinib | 2140.18 | 3.33 | 406.85 | 2.61 | 5.26 | 0.72 |
| EphB4 | Gefitinib | 955.15 | 2.98 | 424.30 | 2.63 | 2.25 | 0.35 |
| MET | Gefitinib | 1207.51 | 3.08 | 5462.33 | 3.74 | 0.22 | −0.66 |
| YES | Gefitinib | 8146.40 | 3.91 | 1343.30 | 3.13 | 6.06 | 0.78 |

TABLE 7

| EXPT | DESCRIPTION | IMMOB INHIBITOR [μM] | LABELS | RATIOS |
|---|---|---|---|---|
| 1 | $K_i$ DETERMINATION VI16742 - RECIPROCAL LABELING SCHEME | 52 | L: 2nd ELUATE FROM VI16742 BEADS<br>M: ELUATE FROM CONTROL BEADS<br>H: 1st ELUATE FROM VI16742 BEADS | $r_1$(2. INC/1. INC) = L/H NORMALIZED 1<br>$r_1$(CONTROL/1. INC) = M/H NORMALIZED 1 |
| 2 | $K_i$ DETERMINATION VI16742 - NORMAL LABELING SCHEME | 52 | L: 1st ELUATE FROM VI16742 BEADS<br>M: ELUATE FROM CONTROL BEADS<br>H: 2nd ELUATE FROM VI16742 BEADS | $r_2$(2. INC/1. INC) = H/L NORMALIZED 2<br>$r_2$(CONTROL/1. INC) = M/L NORMALIZED 2 |
| 3 | $K_i$ DETERMINATION VI16742 - LIGAND CONCENTRATION CONTROL | 59 | L: INCUBATION OF 3 mG PROTEIN WITH VI16742 BEADS<br>H: INCUBATION OF 1 mG PROTEIN WITH VI16742 BEADS | r(3 mG/1 mG LYSATE) = L/H NORMALIZED 3 |
| 4 | $K_i$ DETERMINATION VI16742 - INCUBATION TIME CONTROL | 59 | L: 5 h INCUBATION TIME<br>H: 2.5 h INCUBATION TIME | r(5 h/2.5 h INC. TIME) = L/H NORMALIZED 4 |
| 5 | $IC_{50}$ DETERMINATION SB203580 - 0, 0.1, 1 μM - EXPERIMENT 1 | 59 | L: COMPETITION WITH 0 nM SB203580<br>M: COMPETITION WITH 100 nM SB203580<br>H: COMPETITION WITH 1000 nM SB203580 | $r_1$(100 nM/0 nM SB) = M/L NORMALIZED 5<br>$r_1$(1000 nM/0 nM SB) = H/L NORMALIZED 5 |
| 6 | $IC_{50}$ DETERMINATION SB203580 - 0, 10, 100 μM - EXPERIMENT 1 | 59 | L: COMPETITION WITH 0 nM SB203580<br>M: COMPETITION WITH 10000 nM SB203580<br>H: COMPETITION WITH 100000 nM SB203580 | $r_1$(10000 nM/0 nM SB) = M/L NORMALIZED 6<br>$r_1$(100000 nM/0 nM SB) = H/L NORMALIZED 6 |
| 7 | $IC_{50}$ DETERMINATION SB203580 - 0, 0.1, 1 μM - EXPERIMENT 2 | 59 | L: COMPETITION WITH 0 nM SB203580<br>M: COMPETITION WITH 100 nM SB203580<br>H: COMPETITION WITH 1000 nM SB203580 | $r_2$(100 nM/0 nM SB) = M/L NORMALIZED 7<br>$r_2$(1000 nM/0 nM SB) = H/L NORMALIZED 7 |
| 8 | $IC_{50}$ DETERMINATION SB203580 - 0, 10, 100 μM - EXPERIMENT 2 | 59 | L: COMPETITION WITH 0 nM SB203580<br>M: COMPETITION WITH 10000 nM SB203580<br>H: COMPETITION WITH 100000 nM SB203580 | $r_2$(10000 nM/0 nM SB) = M/L NORMALIZED 8<br>$r_2$(100000 nM/0 nM SB) = H/L NORMALIZED 8 |

TABLE 8

| LEADING PROTEIN | PK | GENE NAME | r$_{AVERAGE}$ (2 INC/ 1 INC) | K$_i$ (VI16742) [μM] | r$_{AVERAGE}$ (CTRL/ 1 INC) | r (3 MG/ 1 MG LYSATE) | r (5 h/ 2.5 h INC. TIME) | r$_{AVERAGE}$ (100 nM/ 0 nM SB) | r$_{AVERAGE}$ (1000 nM/ 0 nM SB) | r$_{AVERAGE}$ (10000 nM/ 0 nM SB) | r$_{AVERAGE}$ (100000 nM/ 0 nM SB) | IC$_{50,AVERAGE}$ (SB203580) [nM] | K$_{i,AVERAGE}$ [nM] (SB203580) | IC$_{50}$~K$_i$ [nM], KINASE ASSAY (SB203580) |
|---|---|---|---|---|---|---|---|---|---|---|---|---|---|---|
| IPI00172450 | CaMK2g | CAMK2G | 0.03 | 1.60 | 0.06 | 2.90 | 0.88 | 0.93 | 1.02 | 0.93 | 0.95 | | | |
| IPI00828081 | CaMK2d | CAMK2D | 0.04 | 1.90 | 0.02 | | 0.82 | 0.92 | 1.10 | 0.96 | 1.01 | | | |
| IPI00301609 | NEK9 | NEK9 | 0.04 | 2.30 | 0.02 | 2.91 | 0.92 | 0.94 | 1.07 | 0.91 | 0.98 | | | |
| IPI00215786 | | PDE10A | 0.05 | 2.58 | 0.03 | | 0.98 | 0.74 | 0.97 | 0.75 | 0.91 | | | |
| IPI00220305 | JNK1 | MAPK8 | 0.05 | 3.01 | 0.04 | 3.21 | 0.94 | 0.91 | 1.00 | 0.82 | 0.51 | 93140 | 4505.40 | |
| IPI00298940 | AurA | AURKA | 0.06 | 3.23 | 0.03 | 3.71 | 1.16 | 0.84 | 0.93 | 0.82 | 0.85 | | | |
| IPI00024673 | JNK2 | MAPK9 | 0.06 | 3.43 | 0.05 | 3.19 | 0.91 | 0.87 | 0.92 | 0.64 | 0.13 | 16760 | 918.88 | 727.55 |
| IPI00411818 | ULK3 | ULK3 | 0.06 | 3.48 | 0.03 | 1.52 | 0.95 | 0.95 | 1.02 | 0.97 | 0.95 | | | |
| IPI00420065 | | ACAD11 | 0.06 | 3.50 | 0.05 | 3.26 | 1.01 | 1.01 | 0.99 | 1.01 | 0.93 | | | |
| IPI00009334 | PKD2 | PRKD2 | 0.06 | 3.56 | 0.02 | 3.08 | 1.11 | 0.90 | 0.99 | 0.85 | 0.35 | 54930 | 3117.67 | |
| IPI00304648 | caMLCK | MYLK3 | 0.07 | 3.66 | 0.01 | | 0.91 | 1.02 | 1.00 | 1.03 | 0.56 | 140700 | 8200.91 | |
| IPI00293613 | CDK2 | CDK2 | 0.07 | 3.69 | 0.04 | 2.93 | 0.97 | 1.00 | 1.08 | 0.95 | 0.96 | | | |
| IPI00031681 | TBK1 | TBK1 | 0.07 | 3.74 | 0.03 | 3.37 | 1.00 | 0.98 | 1.11 | 0.98 | 1.03 | | | |
| IPI00023530 | CDK5 | CDK5 | 0.07 | 3.75 | 0.03 | 2.92 | 0.96 | 0.83 | 1.01 | 0.80 | 0.95 | | | |
| IPI00014934 | DRAK2 | STK17B | 0.07 | 3.75 | 0.01 | 4.20 | 0.79 | 0.96 | 1.05 | 0.75 | 0.81 | | | |
| IPI00552691 | TNK1 | TNK1 | 0.07 | 3.81 | 0.02 | 3.16 | 1.01 | 1.05 | 0.98 | 0.96 | 0.74 | | | |
| IPI00015538 | PKD3 | PRKD3 | 0.07 | 4.01 | 0.05 | 2.91 | 1.02 | 1.00 | 1.03 | 0.97 | 0.46 | 93530 | 5933.54 | |
| IPI00029643 | ZAK | MLTK | 0.07 | 4.07 | 0.09 | 3.74 | 0.99 | 0.77 | 1.14 | 0.81 | 0.79 | | | |
| IPI00219129 | | NQO2 | 0.07 | 4.13 | 0.14 | 2.68 | 0.91 | 0.88 | 1.02 | 0.84 | 0.92 | | | |
| IPI00031004 | | PDXK | 0.08 | 4.65 | 0.08 | 2.97 | 0.96 | 0.89 | 1.06 | 0.86 | 0.96 | | | |
| IPI00021917 | RIPK2 | RIPK2 | 0.09 | 5.06 | 0.02 | 3.62 | 1.04 | 0.09 | 0.03 | 0.04 | 0.02 | 10.5 | 0.83 | 2.16 |
| IPI00216190 | GSK3B | GSK3B | 0.09 | 5.21 | 0.02 | 3.57 | 0.97 | 0.86 | 0.93 | 0.60 | 0.12 | 14340 | 1161.76 | |
| IPI00784013 | JAK1 | JAK1 | 0.09 | 5.35 | 0.04 | 3.65 | 0.98 | 0.89 | 0.90 | 0.78 | 0.36 | 47640 | 3952.36 | |
| IPI00022353 | TYK2 | TYK2 | 0.10 | 5.77 | 0.06 | 4.59 | 0.73 | 0.93 | 0.99 | 0.89 | 0.34 | 56630 | 5036.01 | 3117 |
| IPI00549858 | PCTAIRE1 | PCTK1 | 0.10 | 5.99 | 0.02 | 2.88 | 0.89 | 0.81 | 1.07 | 0.82 | 0.99 | | | |
| IPI00030313 | | CCNT2 | 0.11 | 6.11 | 0.10 | | | 0.96 | 1.05 | 0.85 | 0.93 | | | |
| IPI00029263 | FER | FER | 0.11 | 6.26 | 0.05 | 2.83 | 0.98 | 0.95 | 1.01 | 0.92 | 0.84 | | | |
| IPI00028071 | CLK2 | CLK2 | 0.11 | 6.31 | 0.01 | | 0.96 | 0.93 | 1.06 | 1.04 | 0.95 | | | |
| IPI00329638 | ZAK | MLTK | 0.11 | 6.34 | 0.04 | 3.14 | 0.93 | 0.90 | 1.08 | 0.88 | 0.80 | | | |
| IPI00165249 | PFTAIRE1 | PFTK1 | 0.11 | 6.52 | 0.01 | 2.59 | | 0.89 | 0.81 | 0.90 | 0.85 | | | |
| IPI00020602 | CK2a2 | CSNK2A2 | 0.11 | 6.59 | 0.04 | 2.69 | 0.91 | 1.01 | 1.04 | 0.94 | 0.93 | | | |
| IPI00376955 | PCTAIRE2 | PCTK2 | 0.12 | 6.79 | 0.02 | 2.61 | 0.97 | 0.85 | 0.89 | 0.84 | 0.99 | | | |
| IPI00011416 | | ECH1 | 0.12 | 7.17 | 0.07 | 3.14 | 0.96 | 0.88 | 1.04 | 0.90 | 0.84 | | | |
| IPI00479760 | AAK1 | AAK1 | 0.12 | 7.18 | 0.03 | 3.58 | 1.13 | 0.88 | 1.00 | 0.86 | 0.92 | | | |
| IPI00306833 | MPSK1 | STK16 | 0.13 | 7.45 | 0.11 | 2.40 | 0.86 | 0.95 | 0.99 | 0.94 | 0.88 | | | |
| IPI00185037 | MARK1 | MARK1 | 0.13 | 7.45 | 0.07 | | 0.95 | 0.93 | 1.03 | 0.87 | 0.90 | | | |
| IPI00552413 | CDK9 | CDK9 | 0.13 | 7.48 | 0.02 | 2.77 | 1.00 | 1.01 | 0.98 | 1.03 | 0.92 | | | |
| IPI00220508 | MARK3 | MARK3 | 0.13 | 7.71 | 0.04 | 3.38 | 1.04 | 0.92 | 0.99 | 0.91 | 0.90 | | | |
| IPI00234463 | CK1d | CSNK1D | 0.13 | 7.74 | 0.02 | 3.10 | 1.01 | 0.94 | 0.59 | 0.15 | 0.02 | 1508 | 174.52 | 150.9 |
| IPI00397883 | | | 0.13 | 7.92 | 0.03 | 3.51 | 1.01 | 0.80 | 0.85 | 0.76 | 0.86 | | | |
| IPI00008255 | | AZI2 | 0.14 | 8.57 | 0.12 | 2.83 | 1.01 | 0.99 | 1.07 | 0.90 | 0.94 | | | |
| IPI00176642 | AurB | AURKB | 0.14 | 8.59 | 0.02 | 3.77 | 1.20 | 0.99 | 1.05 | 1.04 | 0.84 | | | |
| IPI00006471 | MELK | MELK | 0.14 | 8.73 | 0.05 | | 0.93 | 0.89 | 0.97 | 0.90 | 0.80 | | | |
| IPI00030247 | | CCNT1 | 0.15 | 9.22 | 0.08 | 2.91 | 1.00 | 1.03 | 1.06 | 0.98 | 0.98 | | | |
| IPI00037426 | BIKE | BMP2K | 0.16 | 9.92 | 0.04 | 2.88 | 0.95 | 0.88 | 1.00 | 0.84 | 0.91 | | | |

TABLE 8-continued

| LEADING PROTEIN | PK | GENE NAME | r$_{AVERAGE}$ (2 INC/ 1 INC) | K$_i$ (VI16742) [µM] | r$_{AVERAGE}$ (CTRL/ 1 INC) | r (3 MG/ 1 MG LYSATE) | r (5 h/ 2.5 h INC. TIME) | r$_{AVERAGE}$ (100 nM SB) | r$_{AVERAGE}$ (1000 nM SB) | r$_{AVERAGE}$ (10000 nM SB) | r$_{AVERAGE}$ (100000 nM SB) | IC$_{50\,AVERAGE}$ (SB203580) [nM] | K$_{i\,AVERAGE}$ [nM] (SB203580) | IC$_{50}$-K$_i$ [nM], KINASE ASSAY (SB203580) |
|---|---|---|---|---|---|---|---|---|---|---|---|---|---|---|
| IPI00639841 |  | PECI | 0.17 | 10.36 | 0.03 | 3.20 | 0.86 | 0.85 | 1.03 | 0.89 | 0.84 | | | |
| IPI00022872 | LIMK2 | LIMK2 | 0.17 | 10.85 | 0.04 |  | 1.08 | 0.88 | 1.14 | 0.88 | 1.04 | | | |
| IPI00293652 | IRAK1 | IRAK1 | 0.17 | 10.90 | 0.06 |  |  |  |  | 1.23 | 1.37 | | | |
| IPI00640088 |  | CSNK2B | 0.17 | 10.90 | 0.06 | 2.81 |  | 0.91 | 1.00 | 0.90 | 0.91 | | | |
| IPI00291702 | LIMK1 | LIMK1 | 0.17 | 10.96 | 0.06 |  | 0.93 | 0.86 | 1.55 | 0.99 | 0.93 | | | |
| IPI00646659 | DRAK1 | STK17A | 0.18 | 11.75 | 0.03 |  | 1.45 | 0.98 | 0.89 | 0.93 | 0.78 | | | |
| IPI00022865 |  | CCNA2 | 0.18 | 11.80 | 0.07 | 3.48 |  | 0.87 | 0.95 | 0.87 | 0.87 | | | |
| IPI00414292 | PCTAIRE3 | PCTK3 | 0.19 | 12.47 | 0.05 |  | 1.10 | 0.76 | 0.81 | 0.60 | 0.85 | | | |
| IPI00292228 | GSK3A | GSK3A | 0.19 | 12.54 | 0.01 | 2.82 | 1.07 | 0.96 | 1.02 | 0.83 | 0.24 | 37870 | 6626.13 | |
| IPI00787268 |  |  | 0.20 | 12.68 | 0.08 | 3.20 | 1.27 | 0.92 | 1.07 | 0.78 | 0.93 | | | |
| IPI00027983 |  | CDA | 0.20 | 12.70 | 0.06 |  | 1.02 | 0.98 | 0.89 | 0.98 | 0.84 | | | |
| IPI00289357 | ULK1 | ULK1 | 0.20 | 13.00 | 0.10 | 2.68 | 0.91 | 0.85 | 0.88 | 0.85 | 0.86 | | | |
| IPI00792479 |  |  | 0.20 | 13.23 | 0.04 | 3.10 | 1.19 | 0.91 | 1.00 | 0.92 | 0.94 | | | |
| IPI00022536 | MSK2 | RPS6KA4 | 0.21 | 14.01 | 0.03 | 2.83 | 1.01 | 0.87 | 0.75 | 0.93 | 0.70 | | | |
| IPI00015809 |  | OSGEP | 0.21 | 14.04 | 0.08 | 7.41 | 0.99 | 0.84 | 1.36 | 0.91 | 1.20 | | | |
| IPI00027729 | CK1e | CSNK1E | 0.21 | 14.18 | 0.03 | 3.31 |  | 1.03 | 0.77 | 0.25 | 0.03 | 3356 | 648.90 | 415.05 |
| IPI00465101 | NEK3 | NEK3 | 0.22 | 14.35 | 0.05 |  | 0.99 | 0.93 | 0.92 | 0.91 | 0.86 | | | |
| IPI00152303 |  | PIP4K2C | 0.23 | 15.26 | 0.04 | 3.21 | 0.88 | 0.89 | 1.04 | 0.91 | 0.87 | | | |
| IPI00465346 | SgK496 | RIPK5 | 0.23 | 15.78 | 0.05 |  |  | 0.85 | 1.06 | 0.97 | 0.85 | | | |
| IPI00005858 | LATS1 | LATS1 | 0.24 | 16.57 | 0.09 |  |  |  |  |  |  | | | |
| IPI00217024 | KHS2 | MAP4K3 | 0.24 | 16.61 | 0.04 | 3.24 | 1.76 | 1.07 | 1.17 | 1.07 | 0.76 | | | |
| IPI00555838 | MARK2 | MARK2 | 0.25 | 17.00 | 0.04 | 2.90 | 1.03 | 0.93 | 0.94 | 0.96 | 0.92 | | | |
| IPI00640957 | MRCKa | CDC42BPA | 0.25 | 17.25 | 0.07 |  |  |  |  |  |  | | | |
| IPI00183860 | MAP2K5 | MAP2K5 | 0.25 | 17.62 | 0.03 |  | 0.90 | 0.91 | 0.99 | 0.87 | 0.65 | | | |
| IPI00655852 | SGK3 | SGK3 | 0.25 | 17.65 | 0.03 |  |  |  |  |  |  | | | |
| IPI00410287 | AMPKa1 | PRKAA1 | 0.26 | 17.80 | 0.03 | 2.67 | 0.93 | 0.93 | 1.02 | 0.99 | 0.99 | | | |
| IPI00307755 | AMPKa2 | PRKAA2 | 0.26 | 17.84 | 0.02 | 0.21 | 0.86 | 0.89 | 1.10 | 0.97 | 1.04 | | | |
| IPI00413318 |  | PRKAG1 | 0.26 | 17.93 | 0.03 | 2.61 | 0.93 | 0.96 | 1.08 | 0.99 | 1.01 | | | |
| IPI00013905 |  | PRKAB2 | 0.26 | 18.11 | 0.10 | 2.85 | 1.02 |  |  | 1.21 | 0.92 | | | |
| IPI00151170 | TTK | TTK | 0.26 | 18.42 | 0.03 | 4.35 | 1.21 | 0.80 | 0.97 | 0.83 | 0.82 | | | |
| IPI00220409 |  | PRKAB1 | 0.26 | 18.47 | 0.04 | 2.82 | 0.93 | 0.78 | 1.01 | 0.81 | 0.96 | | | |
| IPI00168907 |  | IPMK | 0.26 | 18.59 | 0.07 |  |  | 0.96 | 0.87 | 0.91 | 0.89 | | | |
| IPI00301432 |  | TP53RK | 0.27 | 18.95 | 0.05 | 2.41 | 1.04 | 0.91 | 1.07 | 0.95 | 0.97 | | | |
| IPI00290305 | PRPK |  | 0.27 | 19.05 | 0.04 | 2.63 | 1.05 | 0.84 | 0.98 | 0.85 | 0.91 | | | |
| IPI00000977 | MLK3 | MAP3K11 | 0.27 | 19.08 | 0.08 |  |  | 0.57 | 0.87 | 1.04 | 0.80 | | | |
| IPI00017305 | RSK3 | RPS6KA1 | 0.27 | 19.24 | 0.02 | 2.91 | 1.01 | 0.91 | 0.95 | 0.86 | 0.48 | 88220 | 21653.19 | |
| IPI00790374 |  | CSNK1A1 | 0.27 | 19.51 | 0.03 | 2.78 | 0.94 | 1.06 | 0.85 | 0.44 | 0.04 | 7254 | 1799.34 | |
| IPI00220373 |  | IDE | 0.29 | 20.74 | 0.12 |  |  |  |  |  |  | | | |
| IPI00413961 | FAK | PTK2 | 0.29 | 21.04 | 0.04 | 2.67 | 1.06 | 0.96 | 1.03 | 0.94 | 0.94 | | | |
| IPI00016613 | CK2a1 | CSNK2A1 | 0.29 | 21.69 | 0.03 | 2.79 | 0.93 | 0.93 | 1.01 | 0.93 | 0.89 | | | |
| IPI00855985 | MAP3K1 | MAP3K1 | 0.30 | 21.95 | 0.05 | 3.92 | 1.45 | 1.00 | 0.90 | 1.02 | 0.86 | | | |
| IPI00005142 | FGFR1 | FGFR1 | 0.31 | 23.18 | 0.05 |  |  | 0.64 | 0.66 | 0.82 | 0.32 | 41100 | 11570.71 | |
| IPI00003479 | Erk2 | MAPK1 | 0.31 | 23.70 | 0.05 | 2.58 | 1.00 | 1.00 | 1.04 | 0.95 | 0.86 | | | |
| IPI00479349 | SGK | SGK | 0.31 | 24.63 | 0.03 | 2.08 | 0.97 | 0.75 | 1.00 | 0.77 | 0.95 | | | |
| IPI00396662 | NEK6/NEK7 | NEK6 | 0.32 | 25.68 | 0.04 |  |  |  |  |  |  | | | |
| IPI00872391 | PYK2 |  | 0.33 |  | 0.03 | 4.29 | 1.40 | 0.64 | 0.74 | 0.63 | 0.64 | | | |
| IPI00029488 |  | KHK | 0.33 | 25.71 | 0.05 |  |  |  |  |  |  | | | |

TABLE 8-continued

| LEADING PROTEIN | PK | GENE NAME | $r_{AVERAGE}$ (2 INC/ 1 INC) | $K_i$ (VI16742) [µM] | $r_{AVERAGE}$ (CTRL/ 1 INC) | r (3 MG/ 1 MG LYSATE) | r (5 h/ 2.5 h INC. TIME) | $r_{AVERAGE}$ (100 nM 0 nM SB) | $r_{AVERAGE}$ (1000 nM 0 nM SB) | $r_{AVERAGE}$ (10000 nM 0 nM SB) | $r_{AVERAGE}$ (100000 nM/ 0 nM SB) | $IC_{50\ AVERAGE}$ (SB203580) [nM] | $K_{i\ AVERAGE}$ [nM] (SB203580) | $IC_{50}$-$K_i$ [nM], KINASE ASSAY (SB203580) |
|---|---|---|---|---|---|---|---|---|---|---|---|---|---|---|
| IPI00029702 | PYK2 | PTK2B | 0.34 | 26.66 | 0.04 | 3.26 | 1.12 | 1.06 | 1.00 | 1.08 | 0.73 | | | |
| IPI00735354 | | | 0.35 | 27.48 | 0.02 | | | | | | | | | |
| IPI00012443 | | FIBP | 0.35 | 27.94 | 0.05 | 3.00 | 0.98 | 0.97 | 1.02 | 0.84 | 0.96 | | | |
| IPI00026689 | CDC2 | CDC2 | 0.35 | 27.99 | 0.05 | 2.92 | 1.09 | 1.02 | 1.09 | 1.04 | 1.07 | | | |
| IPI00002538 | PDK1 | PDPK1 | 0.35 | 28.08 | 0.03 | | 1.06 | 0.85 | 0.99 | 0.96 | 0.95 | | | |
| IPI00000816 | | YWHAE | 0.35 | 28.17 | 0.11 | 4.07 | 1.15 | 0.91 | 1.04 | 1.12 | 0.95 | | | |
| IPI00298949 | GAK | GAK | 0.35 | 28.55 | 0.04 | 2.88 | 1.05 | 0.77 | 0.24 | 0.06 | 0.87 | 335.4 | 109.20 | 35.24 |
| IPI00216319 | | YWHAH | 0.36 | 28.86 | 0.09 | 4.09 | | 1.16 | 0.94 | | 0.02 | | | |
| IPI00011488 | MST1 | STK4 | 0.36 | 28.88 | 0.05 | | 1.06 | 0.89 | 0.95 | 0.91 | 0.63 | | | |
| IPI00409761 | | CHKA | 0.36 | 29.16 | 0.03 | | | | | | | | | |
| IPI00014266 | BRD3 | BRD3 | 0.36 | 29.36 | 0.04 | 3.42 | 1.27 | 1.25 | 1.03 | 1.26 | 0.25 | 72820 | 24154.87 | |
| IPI00783895 | | KIAA0528 | 0.36 | 29.87 | 0.10 | 3.48 | 1.14 | 0.96 | 0.97 | 0.93 | 0.84 | | | |
| IPI00413780 | PKN3 | PKN3 | 0.37 | 30.94 | 0.06 | | 1.48 | 0.34 | 0.07 | 0.02 | 0.01 | 51.4 | 17.65 | |
| IPI00216318 | | YWHAB | 0.38 | 31.30 | 0.20 | 4.05 | 1.24 | 0.83 | 1.11 | 1.21 | 0.86 | | | |
| IPI00745793 | | CCNB1 | 0.38 | 31.75 | 0.03 | 3.15 | 1.58 | 0.93 | 1.07 | 0.82 | 0.94 | | | |
| IPI00013890 | | SFN | 0.39 | 33.23 | 0.16 | | 1.30 | 0.78 | 1.09 | 1.10 | 0.95 | | | |
| IPI00013981 | YES | YES1 | 0.40 | 34.23 | 0.03 | 3.49 | 1.03 | 1.03 | 0.94 | 0.92 | 0.34 | 58830 | 21566.34 | 4379 |
| IPI00009688 | | PIP4K2A | 0.41 | 35.21 | 0.02 | 4.24 | 1.12 | 0.97 | 1.17 | 1.12 | 0.79 | | | |
| IPI00021263 | | YWHAZ | 0.41 | 36.26 | 0.13 | | | 0.96 | 0.78 | 1.11 | 0.91 | | | |
| IPI00028932 | MAST3 | MAST3 | 0.42 | 38.26 | 0.07 | | 1.15 | 0.76 | 0.96 | 0.96 | 0.74 | | | |
| IPI00377659 | TLK2 | TLK2 | 0.43 | 38.91 | 0.05 | 2.55 | 1.15 | 0.88 | 0.96 | 0.84 | | | | |
| IPI00216470 | | PIP4K2B | 0.43 | 39.25 | 0.04 | 3.37 | 0.98 | 0.99 | 1.06 | 0.95 | 0.77 | | | |
| IPI00018873 | | NAMPT | 0.44 | 40.59 | 0.06 | | | | | | | | | |
| IPI00657861 | DDR1 | DDR1 | 0.44 | 40.77 | 0.07 | | 1.57 | 0.98 | 0.62 | 0.22 | 0.05 | 1972 | 804.64 | |
| IPI00657696 | CaMKK1 | CAMKK1 | 0.44 | 41.19 | 0.04 | 3.40 | 0.94 | 0.81 | 0.95 | 0.99 | 1.08 | | | |
| IPI00021275 | EphB2 | EPHB2 | 0.44 | 41.46 | 0.10 | 2.78 | 0.97 | 0.83 | 0.84 | 0.70 | 0.25 | 24800 | 10220.41 | |
| IPI00289342 | EphB4 | EPHB4 | 0.45 | 41.91 | 0.06 | | | 1.02 | 0.97 | 0.85 | 0.18 | 33650 | 13955.00 | 37714.5 |
| IPI00004363 | STLK3 | STK39 | 0.45 | 42.16 | 0.08 | 2.14 | 1.17 | 0.88 | 0.87 | 0.96 | 0.73 | | | |
| IPI00513803 | MAP3K2 | MAP3K2 | 0.45 | 42.16 | 0.12 | 2.79 | 1.10 | 0.97 | 0.99 | 0.99 | 0.84 | | | |
| IPI00291215 | | PARP14 | 0.45 | 42.53 | 0.04 | 2.69 | 1.08 | 1.02 | 1.11 | 1.03 | 0.92 | | | |
| IPI00018195 | Erk1 | MAPK3 | 0.45 | 42.90 | 0.05 | 3.79 | 0.96 | 1.30 | 1.07 | 1.36 | 0.37 | 105500 | 45286.04 | |
| IPI00440727 | BRD4 | BRD4 | 0.46 | 44.49 | 0.03 | 2.67 | 1.61 | 0.88 | 0.89 | 1.06 | 0.45 | 97000 | 42111.05 | |
| IPI00872474 | LYN | LYN | 0.47 | 45.38 | 0.08 | 2.61 | 0.88 | 1.07 | 0.97 | 1.03 | 0.88 | | | |
| IPI00000685 | CDK7 | CDK7 | 0.47 | 46.17 | 0.08 | 3.63 | 1.16 | 0.98 | 1.06 | 1.03 | 0.86 | | | |
| IPI00014068 | PAK4 | PAK4 | 0.47 | 46.26 | 0.02 | | | 0.82 | 1.13 | 1.01 | 0.71 | | | |
| IPI00411984 | MST2 | STK3 | 0.47 | 46.61 | 0.04 | | | 0.93 | 0.98 | 0.90 | 0.85 | | | |
| IPI00306406 | RIOK2 | RIOK2 | 0.48 | 48.32 | 0.05 | 2.94 | 0.99 | 0.98 | 0.91 | 0.81 | 0.98 | | | |
| IPI00335559 | TLK1 | TLK1 | 0.49 | 49.30 | 0.08 | | | 0.91 | | | | | | |
| IPI00332692 | PIM2 | PIM2 | 0.49 | 49.39 | 0.09 | | | 0.74 | | | | | | |
| IPI00796519 | | TEX264 | 0.50 | 52.86 | 0.07 | | | 0.44 | 1.22 | 0.83 | 0.90 | 31460 | 15018.40 | |
| IPI00221267 | EphA2 | EPHA2 | 0.51 | 54.03 | 0.11 | 2.42 | 1.03 | 0.86 | 1.04 | 0.78 | 0.20 | | | |
| IPI00017726 | | HSD17B10 | 0.51 | 54.48 | 0.08 | | | 0.49 | 0.89 | | | | | |
| IPI00222150 | | PIP5K1A | 0.52 | 55.77 | 0.06 | | 1.41 | 0.93 | 1.01 | 0.90 | 0.62 | | | |
| IPI00031076 | | CCNC | 0.52 | 57.00 | 0.06 | 2.35 | 1.18 | 0.87 | 1.00 | 0.81 | 0.80 | | | |
| IPI00020454 | | DCK | 0.53 | 57.77 | 0.05 | 2.33 | 1.05 | 0.63 | 0.91 | 0.61 | 0.85 | | | |
| IPI00029009 | | PIP5K1C | 0.54 | 60.39 | 0.19 | | | 0.74 | 0.97 | | | | | |
| IPI00470811 | SNRK | SNRK | 0.54 | 60.69 | 0.05 | | | | | | | | | |

TABLE 8-continued

| LEADING PROTEIN | PK | GENE NAME | r_AVERAGE (2 INC/ 1 INC) | K_i (VI16742) [µM] | r_AVERAGE (CTRL/ 1 INC) | r (3 MG/ 1 MG LYSATE) | r (5 h/ 2.5 h INC. TIME) | r_AVERAGE (100 nM SB) | r_AVERAGE (1000 nM SB) | r_AVERAGE (10000 nM SB) | r_AVERAGE (100000 nM SB) | IC_50_AVERAGE (SB203580) [nM] | K_i_AVERAGE [nM] (SB203580) | IC_50~K_i [nM], KINASE ASSAY (SB203580) |
|---|---|---|---|---|---|---|---|---|---|---|---|---|---|---|
| IPI00020898 | RSK2 | RPS6KA3 | 0.54 | 62.17 | 0.03 | 2.35 | 0.97 | 0.97 | 1.03 | 0.93 | 0.81 | | | |
| IPI00329488 | ARG | ABL2 | 0.55 | 64.46 | 0.09 | 2.82 | 1.30 | 0.81 | 0.86 | 0.76 | 0.46 | 67460 | 35180.12 | |
| IPI00873141 | IRE1 | | 0.56 | 66.65 | 0.06 | | | | | | | | | |
| IPI00215999 | PITSLRE | CDC2L1 | 0.57 | 68.38 | 0.05 | 2.94 | | 0.77 | 0.86 | 1.10 | 0.60 | | | |
| IPI00298558 | | PDCD10 | 0.57 | 69.80 | 0.04 | 3.34 | 1.55 | 0.86 | 1.18 | 1.25 | 0.90 | | | |
| IPI00017469 | | SPR | 0.58 | 70.80 | 0.06 | 2.73 | 1.87 | 0.99 | 1.21 | 0.70 | 0.47 | 6161.0 | 33956.99 | |
| IPI00221171 | ABL | ABL1 | 0.58 | 72.63 | 0.06 | 3.23 | | 0.76 | 0.87 | 0.89 | 0.56 | 129600 | 71728.33 | |
| IPI00292827 | MST4 | MST4 | 0.59 | 73.31 | 0.13 | | | 0.91 | 1.46 | | | | | |
| IPI00003031 | | ISOC2 | 0.59 | 75.14 | 0.10 | | | | | | | | | |
| IPI00604647 | HGK/ZC1 | MAP4K4 | 0.59 | 75.73 | 0.05 | | | 1.10 | 1.08 | 0.54 | 0.24 | 16630 | 9337.35 | |
| IPI00027251 | NDR1 | STK38 | 0.60 | 78.33 | 0.01 | | | 0.89 | 1.01 | 1.06 | 0.83 | | | |
| IPI00013212 | CSK | CSK | 0.60 | 79.47 | 0.02 | | 1.51 | 0.93 | 1.10 | 1.01 | 0.76 | | | |
| IPI00219250 | DYRK1A | DYRK1A | 0.62 | 83.84 | 0.08 | | | 0.75 | 1.42 | 1.07 | 1.16 | | | |
| IPI00456970 | CHED | CDC2L5 | 0.62 | 84.63 | 0.05 | 5.31 | 1.42 | 0.95 | 1.00 | 1.07 | 1.07 | | | |
| IPI00872754 | MST3 | STK24 | 0.63 | 89.84 | 0.06 | | 1.41 | 1.06 | 1.65 | | | | | |
| IPI00868781 | CRK7 | CRKRS | 0.64 | 90.68 | 0.07 | 3.21 | 1.04 | 0.93 | 1.00 | | | | | |
| IPI00031410 | FRAP | FRAP1 | 0.64 | 91.64 | 0.10 | | | 0.67 | 2.19 | 1.02 | 1.01 | | | |
| IPI00221141 | p38a | MAPK14 | 0.64 | 92.82 | 0.05 | | 2.16 | | | | | | | |
| IPI00290279 | | ADK | 0.64 | 94.23 | 0.05 | | 1.63 | 0.94 | 1.31 | 1.05 | 0.56 | 146600 | 90064.19 | |
| IPI00177965 | | NT5DC1 | 0.65 | 94.76 | 0.07 | | | 0.93 | 1.15 | 1.16 | 0.46 | 114500 | 70496.23 | |
| IPI00294528 | MET | MET | 0.65 | 94.80 | 0.08 | | | | | | | | | |
| IPI00021305 | | CCNH | 0.65 | 96.92 | 0.05 | | | 0.73 | 0.94 | 1.02 | 0.92 | | | |
| IPI00174390 | | 2-PDE | 0.66 | 100.10 | 0.03 | | | 0.84 | 1.19 | | | | | |
| IPI00002449 | | PDE4D | 0.66 | 102.20 | 0.05 | 2.48 | 1.09 | 0.93 | 0.89 | 0.85 | 0.19 | 33530 | 21237.74 | |
| IPI00002580 | | PIK3C2A | 0.67 | 104.01 | 0.18 | | | | | | | | | |
| IPI00514275 | TNIK/ZC2 | TNIK | 0.67 | 107.87 | 0.19 | | 1.27 | 0.90 | 0.91 | 0.69 | 0.27 | 26770 | 17289.25 | |
| IPI00074258 | MASTL | MASTL | 0.68 | 109.31 | 0.09 | | | | | | | | | |
| IPI00002804 | PKN2 | PKN2 | 0.69 | 114.53 | 0.03 | 2.87 | 1.35 | 0.94 | 1.00 | 0.98 | 0.83 | | | |
| IPI00410485 | TAO3 | TAOK3 | 0.69 | 116.38 | 0.09 | 2.95 | | 0.77 | 1.08 | 0.88 | | | | |
| IPI00099986 | | FN3KRP | 0.69 | 116.78 | 0.07 | 2.02 | 0.95 | 0.87 | 0.93 | 0.90 | 0.85 | | | |
| IPI00029728 | | ERCC2 | 0.69 | 117.61 | 0.17 | | | | | | | | | |
| IPI00023529 | CDK6 | CDK6 | 0.70 | 118.79 | 0.10 | | 0.75 | | | | | | | |
| IPI00783214 | | CCNK | 0.70 | 119.73 | 0.12 | | 1.27 | 0.94 | 0.90 | 0.96 | 0.88 | | | |
| IPI00006025 | | SART3 | 0.71 | 126.21 | 0.05 | 3.84 | 0.90 | 0.92 | 0.88 | 0.66 | | | | |
| IPI00789335 | MAP2K4 | MAP2K4 | 0.71 | 127.45 | 0.06 | 2.07 | | | | 0.73 | 0.79 | | | |
| IPI00220766 | | GLO1 | 0.72 | 133.18 | 0.07 | | 1.39 | 0.67 | 0.82 | 0.99 | 0.85 | | | |
| IPI00788612 | | LIMS1 | 0.73 | 143.22 | 0.04 | | | | | | | | | |
| IPI00218858 | MAP2K3 | MAP2K3 | 0.74 | 149.96 | 0.05 | 3.39 | 1.60 | | | | | | | |
| IPI00018963 | | PARVA | 0.75 | 155.43 | 0.06 | | 1.04 | 0.90 | 0.92 | 0.89 | 0.74 | | | |
| IPI00012197 | | XTP3TPA | 0.75 | 159.12 | 0.08 | | | 1.14 | 1.17 | 1.11 | 1.04 | | | |
| IPI00783305 | BUB1 | BUB1 | 0.76 | 161.39 | 0.05 | 3.59 | 1.98 | 0.75 | 0.69 | 0.37 | 0.08 | 3708 | 2713.51 | |
| IPI00021290 | | ACLY | 0.76 | 161.61 | 0.06 | 2.64 | 1.02 | 0.75 | 1.07 | 1.07 | 1.03 | | | |
| IPI00002232 | TAO1 | TAOK1 | 0.76 | 162.43 | 0.06 | | | 0.88 | 1.00 | 1.00 | 0.65 | | | |
| IPI00304742 | LOK | STK10 | 0.76 | 163.64 | 0.07 | | | 0.84 | 1.13 | 0.77 | | | | |
| IPI00033388 | DAPK2 | DAPK2 | 0.77 | 171.44 | 0.11 | | 1.47 | | | | | | | |
| IPI00013219 | ILK | ILK | 0.77 | 171.70 | 0.03 | | 2.03 | 0.85 | 0.84 | 0.88 | 0.87 | | | |
| IPI00003783 | MAP2K2 | MAP2K2 | 0.77 | 177.14 | 0.03 | | | 0.77 | 0.83 | 0.75 | 0.37 | 44100 | 33060.62 | |

TABLE 8-continued

| LEADING PROTEIN | PK | GENE NAME | r$_{AVERAGE}$ (2 INC/ 1 INC) | K$_i$ (VI16742) [µM] | r$_{AVERAGE}$ (CTRL/ 1 INC) | r (3 MG/ 1 MG LYSATE) | r (5 h/ 2.5 h INC. TIME) | r$_{AVERAGE}$ (100 nM/ 0 nM SB) | r$_{AVERAGE}$ (1000 nM/ 0 nM SB) | r$_{AVERAGE}$ (10000 nM/ 0 nM SB) | r$_{AVERAGE}$ (100000 nM/ 0 nM SB) | IC$_{50,AVERAGE}$ (SB203580) [nM] | K$_{i,AVERAGE}$ [nM] (SB203580) | IC$_{50}$~K$_i$ [nM], KINASE ASSAY (SB203580) |
|---|---|---|---|---|---|---|---|---|---|---|---|---|---|---|
| IPI00003814 | MAP2K6 | MAP2K6 | 0.77 | 178.30 | 0.05 | 2.41 | 1.36 | 0.83 | 0.91 | 0.87 | 0.84 | | | |
| IPI00219604 | MAP2K1 | MAP2K1 | 0.78 | 179.85 | 0.07 | | 1.68 | 0.84 | 0.90 | 0.94 | 0.49 | 96960 | 72963.18 | |
| IPI00413108 | | RPSA | 0.78 | 184.56 | 0.11 | 3.92 | 2.26 | 0.89 | 1.37 | 1.27 | 1.09 | | | |
| IPI00024709 | IKKb | IKBKB | 0.79 | 200.75 | 0.06 | | | 0.65 | 0.55 | 1.07 | 0.74 | | | |
| IPI00010080 | OSR1 | OXSR1 | 0.80 | 206.63 | 0.05 | | | 0.83 | 1.02 | 0.99 | 1.05 | | | |
| IPI00375824 | | DPH5 | 0.80 | 211.15 | 0.03 | | 2.72 | | | | | | | |
| IPI00847168 | | RSU1 | 0.81 | 216.45 | 0.07 | | 1.34 | 0.76 | 0.93 | 0.96 | 0.95 | | | |
| IPI00335101 | MSK1 | RPS6KA5 | 0.81 | 216.73 | 0.03 | | | | | | | | | |
| IPI00022827 | SLK | SLK | 0.81 | 216.99 | 0.05 | 3.22 | 1.87 | 0.69 | 1.08 | 0.72 | 0.34 | 40510 | 31832.71 | |
| IPI00328318 | | AGL | 0.81 | 217.79 | 0.08 | | | 0.92 | 0.80 | 1.07 | 0.74 | | | |
| IPI00218693 | | APRT | 0.81 | 222.93 | 0.05 | 1.04 | 1.40 | 1.11 | 0.87 | 0.89 | 0.77 | | | |
| IPI00300567 | | DCI | 0.82 | 236.25 | 0.04 | 3.25 | 1.68 | 0.88 | 1.12 | 1.36 | 1.10 | | | |
| IPI00066754 | | WDR68 | 0.83 | 249.46 | 0.17 | 2.58 | 1.31 | 0.83 | 0.78 | 0.86 | 0.75 | | | |
| IPI00307155 | ROCK2 | ROCK2 | 0.83 | 254.87 | 0.08 | 3.18 | 1.74 | 0.83 | 0.96 | 0.82 | 0.12 | 27210 | 22084.64 | |
| IPI00012891 | PHKg2 | PHKG2 | 0.85 | 295.80 | 0.10 | 2.14 | 1.33 | | | | | | | |
| IPI00477763 | MRCKb | CDC42BPB | 0.85 | 301.21 | 0.06 | 2.35 | 1.34 | 0.94 | 0.80 | 0.94 | 0.41 | 73260 | 61234.91 | |
| IPI00396630 | PKACa | PRKACA | 0.85 | 305.35 | 0.04 | 2.18 | 1.76 | 0.78 | 0.88 | 0.74 | 0.62 | | | |
| IPI00376119 | PKACb | PRKACB | 0.88 | 389.53 | 0.01 | | | 0.89 | 1.00 | | | | | |
| IPI00007811 | CDK4 | CDK4 | 0.91 | 511.13 | 0.07 | 1.77 | 1.03 | 0.61 | 0.85 | 0.80 | 0.75 | | | |

The invention claimed is:

1. A method for evaluating a binding affinity of a target component of an analyte to a compound, wherein the target component is a protein, wherein the compound is a kinase inhibitor, and wherein the analyte is selected from the group consisting of a proteome, a mixture of different proteomes, a cell extract or lysate, a tissue extract or lysate, a cell culture supernatant, a tissue culture supernatant or a body fluid, the method comprising
   (a) contacting a first aliquot of the analyte with a first solid support onto which the compound is immobilized in a defined concentration under conditions permitting the binding of the target component in the analyte to the immobilized compound, wherein the target component is labelled with a detectable label, and wherein the detectable label is different in each aliquot of the analyte;
   (b) contacting a second aliquot of the analyte with a solid support onto which the compound is immobilized as in step (a), wherein said solid support comprises the same solid support material as the solid support in step (a), and wherein the compound is immobilized in the same concentration as in step (a) under conditions permitting the binding of the target component to the compound, and subsequently separating a supernatant of the second aliquot of the analyte from said solid support;
   (c) contacting the supernatant separated from the solid support in step (b) with a solid support onto which the compound is immobilized as in step a), wherein said solid support comprises the same solid support material as the solid support in step a) and wherein the compound is immobilized in the same concentration as in step a) under conditions permitting the binding of the target component to the compound;
   (d) determining the amounts of the target component bound to the solid support in step (a) and the solid support in step (c);
   (e) comparing the amount of target component bound to the solid support in step (a) to the amount of target component bound to the solid support in step (c); and
   (f) determining the $K_d$ value of the binding of the target component to the immobilized compound based on the comparison in step (e).

2. The method of claim 1, further comprising contacting a third aliquot of said analyte with a solid support, wherein the solid support comprises the same solid support material as the solid support in step (a) but does not have said compound immobilized onto it, and determining the amount of target component bound to said solid support;
   wherein step (e) further comprises comparing the amounts of target component bound to the solid support in step (a) and the solid support in step (c) to the amount of target component bound to said solid support that does not have said compound immobilized onto it.

3. A method for evaluating a binding affinity of a target component of an analyte to a compound, wherein the target component is a protein, wherein the compound is a kinase inhibitor, and wherein the analyte is selected from the group consisting of a proteome, a mixture of different proteomes, a cell extract or lysate, a tissue extract or lysate, a cell culture supernatant, a tissue culture supernatant or a body fluid, the method comprising
   (a) contacting a first aliquot of the analyte with a first solid support onto which the compound is immobilized under conditions permitting the binding of the target component in the analyte to the immobilized compound, wherein the target component is labelled with a detectable label, and wherein the detectable label is different in each aliquot of the analyte;
   (b) contacting a second aliquot of the analyte with a second solid support, wherein the second solid support is the same as the first solid support except said compound is immobilized onto the second solid support at a higher concentration than on the first solid support of step (a) under conditions permitting the binding of the target component to the immobilized compound;
   (c) determining the amounts of target component bound to the first solid support in step (a) and the second solid support in step (b); and
   (d) comparing the amounts of target component bound to the first solid support in step (a) and the second solid support in step (b); and
   (e) determining the $K_d$ value of the binding of the target component to the compound based on the comparison in step (d).

4. The method of claim 3, wherein a ratio of the concentrations in which the compound is immobilized onto the solid support in steps (a) and (b) is selected from the ratios of about 1:2, about 1:3, about 1:4, about 1:5, about 1:6, about 1:7, about 1:8, about 1:9, or about 1:10.

5. The method of claim 3, further comprising contacting a third aliquot of said analyte with a third solid support, wherein the third solid support does not have said compound immobilized onto it, and determining the amount of target component bound to said third solid support;
   wherein step (d) further comprises comparing the amounts of target component bound to the first solid support in step (a) and the second solid support in step (b), to the amount of target component bound to said third solid support.

6. The method of claim 1, wherein said labelling is done by a stable isotope labelling with amino acids in cell culture (SILAC) procedure, and wherein said determination according to step (d) is done by quantitative protein analysis via mass spectrometry.

7. The method of claim 1, wherein the determining step (d) comprises combining said bound target components into one sample and detecting the amounts of differently labelled target components in said sample.

8. The method of claim 7, farther comprising a step of eluting the target components from the solid supports in steps (a) and (c) prior to being combined into said sample.

9. The method of claim 1, wherein the compound is present during said contacting steps in a molar excess compared to the target component.

10. The method of claim 1, wherein said contacting steps (a) and (b) are performed simultaneously.

11. The method according to claim 1, wherein the proteome is present in or derived from one single cell or cell culture, a mixture of cells, a tissue, an organ or an organism.

12. The method according to claim 1, wherein the solid support is selected from the group consisting of filters, glass slides, silicon surfaces, beads and a customized chemical microarray.

13. The method of claim 12, wherein said beads are sepharose beads, optionally epoxy-activated or NHS-activated, or agarose beads.

14. The method according to claim 1, wherein the immobilized compound is immobilized onto the solid support via adsorption, absorption, ionic bonding, covalent bonding, an amino-group or carboxy-group or hydroxy-group, (strept) avidin-biotin, or thiol-gold interactions.

15. The method according to claim 1, wherein said label is selected from the group consisting of radiolabels, dye labels, labels that can be detected with antibodies, enzyme labels, phosphorescent markers, fluorescent markers, chemiluminescent markers, phosphatases, avidin, streptavidin, biotin, TAP, peroxidases and labels having a detectable mass.

16. The method according to claim 1, wherein said contacting is performed essentially under physiological conditions.

17. The method according to claim 1, wherein said contacting is performed using a buffer and, optionally, a cofactor selected from NAD+/NADH, cGMP, NADP+/NADPH, ATP, ADP, or cAMP.

18. The method according to claim 1, wherein the determination according to step (d) comprises detecting the label by a method selected from radioactivity detection methods, fluorescence detection methods, luminescence detection methods, dye detection methods, enzymatic detection methods and mass spectrometry.

19. The method according to claim 1, wherein said method comprises simultaneously evaluating the binding of a multitude of target components of the analyte to the immobilized compound.

20. The method according to claim 1, wherein said method is performed in whole or at least in part in a high throughput manner.

21. The method of claim 3, further comprising a step of contacting a third aliquot of the analyte with a third solid support that is the same as the second solid support of step (b) except said compound is immobilized on the third solid support at a higher concentration than on the second solid support of step (b) under conditions permitting the binding of the target component to the compound; and wherein the determining step (c) further comprises determining the amount of target component bound to the third solid support; and wherein the comparing step (d) further comprises comparing the amount of target component bound to the third solid support.

22. The method of claim 21, wherein a ratio of the concentrations in which the compound is immobilized Onto the first, second and third solid support is selected from the ratios of about 1:2:4, about 1:3:9, about 1:4:16, about 1:5:25, about 1:6:36, about 1:7;49, about 1:8:64, about 1:9:81, or about 1:10:100.

23. The method of claim 1, wherein the compound is a small molecule.

24. The method of claim 3, wherein the compound is a small molecule.

25. The method of claim 3, wherein said labelling is done by a stable isotope labelling with amino acids in cell culture (SILAC) procedure, and wherein said determination according to step (c) is done by quantitative protein analysis via mass spectrometry.

26. The method of claim 3, wherein the determining step (c) comprises combining said bound target components into one sample and detecting the amounts of differently labelled target components in said sample.

27. The method of claim 26, further comprising a step of eluting the target components from the first and second solid supports prior to being combined into said sample.

28. The method of claim 3, wherein the compound is present during said contacting steps in a molar excess compared to the target component.

29. The method of claim 3, wherein said contacting steps (a) and (b) are performed simultaneously.

30. The method of claim 3, wherein the proteome is present in or derived from one single cell or cell culture, a mixture of cells, a tissue, an organ or an organism.

31. The method of claim 3, wherein the solid support is selected from the group consisting of filters, glass slides, silicon surfaces, beads and a customized chemical microarray.

32. The method of claim 31, wherein said beads are sepharose beads, optionally epoxy-activated or NHS-activated, or agarose beads.

33. The method of claim 3, wherein the immobilized compound is immobilized onto the solid support via adsorption, absorption, ionic bonding, covalent bonding, an amino-group or carboxy-group or hydroxy-group, (strept)avidin-biotin, or thiol-gold interactions.

34. The method of claim 3, wherein said label is selected from the group consisting of radiolabels, dye labels, labels that can be detected with antibodies, enzyme labels, phosphorescent markers, fluorescent markers, chemiluminescent markers, phosphatases, avidin, steptavidin, biotin, TAP, peroxidases and labels having a detectable mass.

35. The method of claim 3, wherein said contacting is performed essentially under physiological conditions.

36. The method of claim 3, wherein said contacting is performed using a buffer and, optionally, a cofactor selected from NAD+/NADH, cGMP, NADP+/NADPH, ATP, ADP, or cAMP, 37. The method of claim 3, wherein the determination according to step (c) comprises detecting the label by a method selected from radioactivity detection methods, fluorescence detection methods, luminescence detection methods, dye detection methods, enzymatic detection methods and mass spectrometry.

38. The method of claim 3, wherein said method comprises simultaneously evaluating the binding of a multitude of target components of the analyte to the immobilized compound.

39. The method of claim 3, wherein said method is performed in whole or at least in part in a high throughput manner.

* * * * *